United States Patent
Theodoridis et al.

(10) Patent No.: US 8,119,563 B2
(45) Date of Patent: Feb. 21, 2012

(54) N-SUBSTITUTED AZACYCLES

(75) Inventors: George Theodoridis, Princeton, NJ (US); David Rosen, Kendall Park, NJ (US); Shunxiang Zhang, Plainsboro, NJ (US); Walter H. Yeager, Yardley, PA (US); Robert N. Henrie, II, Pennington, NJ (US); Syed Z. Ahmed, Pennington, NJ (US); Hongbin Men, Edison, NJ (US); Stephen Donovan, Revere, PA (US)

(73) Assignee: FMC Corporation, Philadelphia, PA (US)

( * ) Notice: Subject to any disclaimer, the term of this patent is extended or adjusted under 35 U.S.C. 154(b) by 1047 days.

(21) Appl. No.: 10/595,298

(22) PCT Filed: Oct. 4, 2004

(86) PCT No.: PCT/US2004/032720
§ 371 (c)(1),
(2), (4) Date: Dec. 22, 2008

(87) PCT Pub. No.: WO2005/036961
PCT Pub. Date: Apr. 28, 2005

(65) Prior Publication Data
US 2009/0215821 A1    Aug. 27, 2009

Related U.S. Application Data

(60) Provisional application No. 60/510,568, filed on Oct. 10, 2003, provisional application No. 60/609,533, filed on Sep. 13, 2004.

(51) Int. Cl.
*A01N 43/22* (2006.01)
*C07D 211/06* (2006.01)

(52) U.S. Cl. ........ 504/130; 514/318; 514/327; 546/194; 546/216

(58) Field of Classification Search .................. 504/130; 514/318, 327; 546/194, 216
See application file for complete search history.

(56) References Cited

U.S. PATENT DOCUMENTS

| | | | |
|---|---|---|---|
| 3,056,795 A | 10/1962 | Archer et al. | |
| 4,178,377 A | 12/1979 | Rissi et al. | |
| 5,569,664 A * | 10/1996 | Silverman et al. | 514/317 |
| 5,639,763 A | 6/1997 | Silverman et al. | |
| 5,795,901 A | 8/1998 | Szczepanski | |
| 5,939,438 A | 8/1999 | Yeager et al. | |
| 6,017,931 A | 1/2000 | Silverman et al. | |
| 6,030,987 A | 2/2000 | Silverman et al. | |
| 6,184,234 B1 | 2/2001 | Silverman et al. | |
| 2003/0119806 A1 | 6/2003 | Lindell et al. | |

FOREIGN PATENT DOCUMENTS

| | | |
|---|---|---|
| JP | 2002/220372 A | 8/2002 |
| WO | WO 00/20409 A1 | 4/2000 |
| WO | WO 02/068392 A1 | 9/2002 |

OTHER PUBLICATIONS

Database CAPLUS, STN Accession No. 2003:221676, English language abstract for Guzi, T., et al., "Preparation of substituted 1-benzhydryl-4-[2-(4-piperidinyl)acetyl]-piperazines as 17-β-hydroxysteroid dehydrogenase type 3 inhibitors for the treatment of androgen dependent diseases," Patent No. WO 2003/022835, Schering Corporation, USA (Mar. 2003).
International Search Report for International Application No. PCT/US04/32720, United States Patent and Trademark Office, Alexandria, VA, mailed on Jul. 5, 2005.

* cited by examiner

*Primary Examiner* — Rebecca Anderson
*Assistant Examiner* — Samantha Shterengarts

(57) ABSTRACT

N-substituted azacycle derivative compounds represented by formula (I):

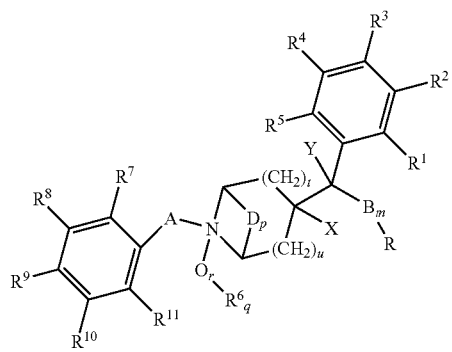

wherein m, q, r, t and u are independently selected from 0 or 1; and p is 0, 1, 2, or 3; and A, B, D, X, Y, R, $R^1$, $R^2$, $R^3$, $R^4$, $R^5$, $R^6$, $R^7$, $R^8$, $R^9$, $R^{10}$ and $R^{11}$ are fully described herein. The compounds being particularly useful in compositions comprising an insecticidally effective amount of at least one compound of formula I, and an insecticidally compatible carrier are also disclosed; along with methods of controlling insects comprising applying said compositions to a locus where insects are present or are expected to be present.

24 Claims, No Drawings

N-SUBSTITUTED AZACYCLES

This application claims the benefit of U.S. Provisional Application No. 60/510,568, filed Oct. 10, 2003 and U.S. Provisional Application No. 60/609,533, filed Sep. 13, 2004.

FIELD OF THE INVENTION

The present invention generally relates to novel compounds, processes and intermediates useful in preparing such compounds, compositions containing such compounds and the use of such compounds in controlling insects. In particular, it pertains to N-substituted azacycle derivatives, N-oxides, and agriculturally acceptable salts thereof, compositions of these insecticides, and methods for their use in controlling insects.

BACKGROUND OF THE INVENTION

A longstanding worldwide demand exists for new, effective, less costly, and safe means to control pests in agricultural crops, greenhouse crops, nursery crops, ornamentals, turfs, forestry, stored food and fiber products, structures, livestock, households, and public and animal health. Agricultural crop costs incurred by pests exceed billions of dollars annually in decreased crop yields, reduced crop quality and increased harvesting costs. Agricultural crops include wheat, corn, soybeans, potatoes, and cotton to name a few. Soil-bourne insects, such as termites and white grubs, cause millions of dollars of damage to structures, turfs and ornamentals. Household pests, such as flies, ants and cockroaches, carry disease and are undesirable in peoples' homes. In addition to these pests, many blood-feeding insects are vectors for pathogenic microorganisms that threaten human and animal health, or are annoying at the least. Insecticides are desired which can control these pests without damaging crops, turfs, ornamentals or structures, and which have no deleterious effects to mammals and other living organisms.

A number of patents disclose a variety of insecticidally active azacycle derivatives. For example, as set forth in U.S. Pat. No. 5,569,664, compounds of the following structure are reported to be insecticidally active:

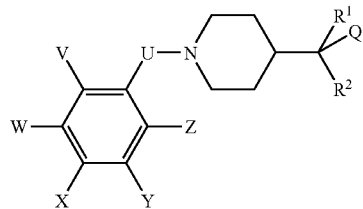

where U is selected from —$(CH_2)_n$— and ethylidine, where n is 1, 2, or 3; Q is selected from hydrogen, hydroxy, sulfhydryl, and fluorine; V is selected from hydrogen, halogen, alkyl, haloalkyl, alkoxy, alkylthio, alkylsulfinyl, alkylsilyloxy, dialkylamino, cyano, nitro, hydroxy, and phenyl; W is selected from hydrogen, halogen, alkyl, haloalkyl, alkoxy, nitro, amino, phenoxy, and phenylalkoxy; X is selected from hydrogen, hydroxy, halogen, alkyl, alkoxyalkyl, alkoxy, cycloalkylalkoxy, haloalkoxy, alkenyloxy, alkynyloxy, alkylsilyloxy, alkylthio, haloalkylthio, cyano, cyanoalkoxy, nitro, amino, monoalkylamino, dialkylamino, alkylaminoalkoxy, alkylcarbonylamino, alkoxycarbonylamino, alkylcarbonyl, alkoxycarbonyl, alkylaminocarbonyl, aminocarbonyloxy, phenyl, phenylalkoxy, ohenoxy, and phenoxyalkyl; Y and Z are independently selected from hydrogen and alkoxy; $R^1$ and $R^2$ are independently selected from phenyl substituted with halogen, alkyl, haloalkyl, haloalkoxy, alkoxyalkyl, hydroxy, arylthio, alkoxy, dialkylamino, dialkylaminosulfonyl, hydroxyalkylaminocarbonyl, alkylsulfonyloxy, and haloalkylsulfonyloxy; and the corresponding N-oxides and agriculturally acceptable salts.

As set forth in U.S. Pat. No. 5,639,763 compounds of the following structure are reported to be insecticidally active:

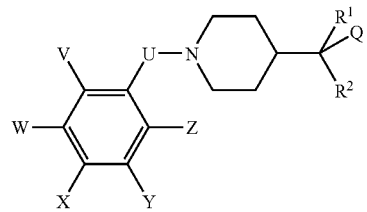

where U is selected from —$(CH_2)_n$— and ethylidine, where n is 1, 2, or 3; Q is selected from hydrogen, hydroxy, sulfhydryl, and fluorine; V is selected from hydrogen, halogen, alkyl, haloalkyl, alkoxy, alkylthio, alkylsulfinyl, alkylsilyloxy, dialkylamino, cyano, nitro, hydroxy, and phenyl; Y and Z are independently selected from hydrogen and alkoxy; W and X taken together is —$OCH_2CH_2O$—, —$CH_2C(CH_3)_2 O$—, —$OC(CH_3)_2O$—, or —$N$=$C(C_2H_5)O$—; $R^1$ and $R^2$ are independently selected from phenyl substituted with halogen, alkyl, haloalkyl, haloalkoxy, alkoxyalkyl, hydroxy, arylthio, alkoxy, dialkylamino, dialkylaminosulfonyl, hydroxyalkylaminocarbonyl, alkylsulfonyloxy, and haloalkylsulfonyloxy; and the corresponding N-oxides and agriculturally acceptable salts.

As set forth in U.S. Pat. No. 5,795,901 compounds of the following structure are reported to be insecticidally active:

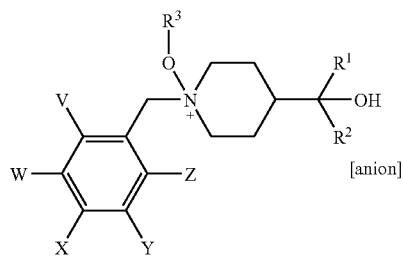

where V, W, Y, and Z are hydrogen; X is alkoxy, cycloalkoxy, alkoxycarbonyl, alkoxycarbonylamino, or a five- or six-membered heteroaryl or heteroaryloxy, each heteroaryl optionally substituted with halogen, cyano, alkyl, haloalkyl, alkoxy, haloalkoxy, alkoxyalkyl, or haloalkoxyalkyl; $R^1$ and $R^2$ are independently selected from haloalkyl, phenyl substituted with halogen, halothio, haloalkyl, or haloalkoxy; or a five- or six-membered heteroaryl substituted with halogen or alkyl; $R^3$ is alkyl, haloalkyl, hydroxyalkyl, alkoxyalkyl, dialkylaminoalkyl, alkylaminocarbonyloxyalkyl, alkylthioalkyl, alkylsulfonylalkyl, alkylcarbonyloxyalkyl, alkoxycarbonylalkyl, carboxyalkyl, carboxyarylalkyl, arylcarbonyl, sulfonato, or sulfonatoalkyl, and may bear a negative charge resulting in an inner salt, and a separate anion is chloride, bromide, iodide, or a phenyl, or alkyl sulfate or sulfonate.

As set forth in U.S. Pat. No. 5,939,438 compounds of the following structure are reported to be insecticidally active:

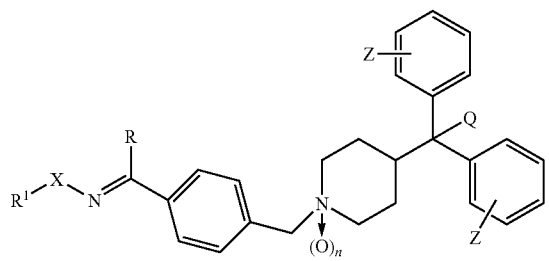

where R is hydrogen, halogen, alkyl, alkoxy, or dialkylamino; $R^1$ is hydrogen, alkyl, haloalkyl, alkoxyalkyl, alkylcarbonyl, or alkylaminocarbonyl; Q is fluoro or hydroxy; X is oxygen or $NR^2$; Z is halogen, haloalkyl, haloalkoxy, pentahalothio, haloalkylthio, haloalkylsulfinyl, haloalkylsulfonyl, or —$OCF_2O$— attached to two adjacent carbon atoms of the phenyl ring; n is 0 or 1; and, when X is $NR^2$, $R^2$ is hydrogen, alkyl, alkylcarbonyl, alkoxycarbonyl, or $R^1$ and $R^2$ taken together may be —$C_mH_{2m}$—, or —$C_2H_4OC_2H_4$—, where m is 3-9; and their agriculturally acceptable salts.

As set forth in U.S. Pat. No. 6,017,931 compounds of the following structure are reported to be insecticidally active:

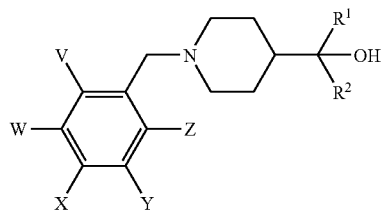

where V, W, and Z are hydrogen; X is selected from alkoxy, haloalkoxy, alkoxyalkyl, cycloalkylalkoxyl, halocycloalkylalkoxy, alkoxycarbonyl, haloalkoxycarbonyl, cycloalkylalkoxylcarbonyl, halocycloalkylalkoxylcarbonyl, alkoxyalkoxycarbonyl, alkoxycarbonylamino, haloalkoxycarbonylamino, cycloalkylalkoxycarbonylamino, halocycloalkylalkoxycarbonylamino, alkylaminocarbonyl, haloalkylaminocarbonyl, cyanoalkoxycarbonylamino, phenylcarbonylamino, and phenoxycarbonyl, each cycloalkyl moiety or phenyl ring optionally substituted with halogen; Y is selected from hydrogen or halogen; $R^1$ and $R^2$ are independently selected from phenyl or pyridyl, each substituted with haloalkyl, haloalkoxy, or alkylthio, and the corresponding N-oxides and agriculturally acceptable salts.

As set forth in U.S. Pat. No. 6,030,987 compounds of the following structure are reported to be insecticidally active:

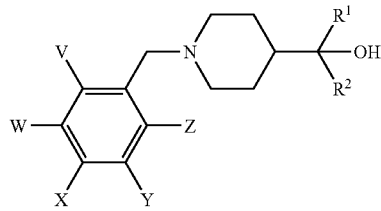

where V, W, Y and Z are hydrogen; X is a five- or six-membered heterocycle optionally substituted with halogen, alkyl, alkoxy, alkoxyalkyl, cyano, aminocarbonyl, haloalkyl, haloalkoxy, or haloalkoxyalkyl; and the heterocycle is optionally connected to the phenyl ring through a —O—, —S—, —$(CH_2)_p$—, —C(O)—, or —$O(CR^3R^4)_q$— linkage; $R^1$ and $R^2$ are independently selected from phenyl or pyridyl, each substituted with haloalkyl, or haloalkoxy; $R^3$ and $R^4$ are independently selected from hydrogen and methyl; n and p are independently 1, 2, or 3; and q is 1 or 2, and the corresponding N-oxides and agriculturally acceptable salts.

As set forth in U.S. Pat. No. 6,184,234 compounds of the following structure are reported to be insecticidally active:

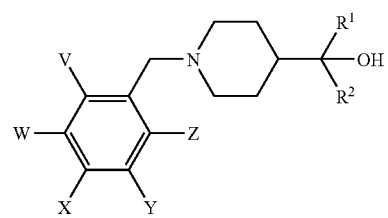

where V, W, Y and Z are hydrogen; X is a five- or six-membered heterocycle optionally substituted with bromine, chlorine, fluorine, alkyl, alkoxy, alkoxyalkyl, cyano, aminocarbonyl, haloalkyl, haloalkoxy, or haloalkoxyalkyl; and the heterocycle is optionally connected to the phenyl ring through a —O—, —S—, —$(CH_2)_p$—, —C(O)—, or —$O(CR^3R^4)_q$— linkage; $R^1$ and $R^2$ are independently selected from i) phenyl or pyridyl, each substituted with pentahalothio, haloalkylthio, haloalkylsulfinyl, or haloalkylsulfonyl; ii) phenyl substituted with —$OC(M)_2O$—, where M is bromine, chlorine, or fluorine to provide a dihalobenzodioxolyl fused ring; or iii) pyridyl substituted with —$OC(M)_2O$—, to provide a dihalodioxoleneopyridyl fused ring; $R^3$ and $R^4$ are independently selected from hydrogen and methyl; n and p are independently 1, 2, or 3; and q is 1 or 2, and the corresponding N-oxides and agriculturally acceptable salts.

As set forth in United States Statutory Invention Registration H1,838 compounds of the following structure are reported to be insecticidally active:

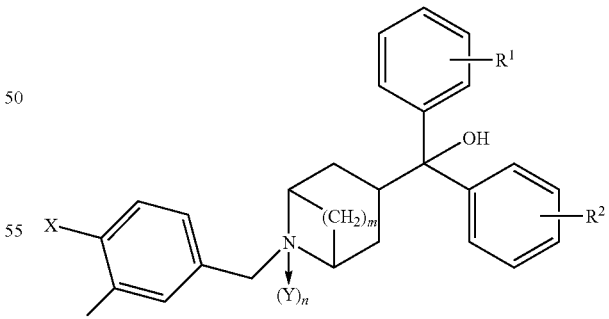

where m is 2 or 3; n is 0 or 1; W is hydrogen or alkoxy; X is hydrogen, alkoxy, cycloalkylalkoxy, haloalkoxyimino, or a five- or six-membered heteroaryl or heteroaryloxy in which one or more hetero atoms may be optionally substituted with alkyl; $R^1$ and $R^2$ are independently selected from hydrogen, haloalkyl, halothio, or haloalkoxy; and when n is 1, Y represents (a) an N-oxide of the ring nitrogen; or (b) an agriculturally acceptable anionic salt of the ring nitrogen; or (c) forms an $OR^3$ linkage in which $R^3$ is selected from hydrogen, alkyl, alkoxycarbonylalkyl, hydroxycarbonylethyl in association with an agriculturally acceptable anion resulting in an ionic salt, or $R^3$ is an oxycarbonylalkyl group bearing a negative charge resulting in an inner salt.

As set forth in United States Statutory Invention Registration H1,996 photostable, agriculturally acceptable acid salts of an organic or inorganic acid of the following structure are reported to be insecticidally active:

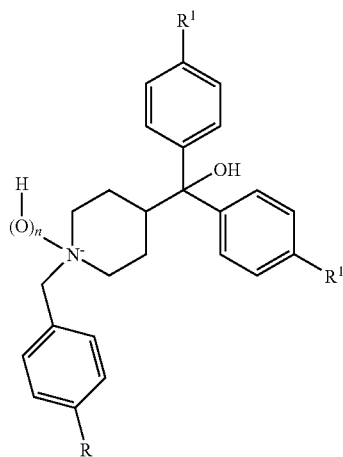

where R is alkoxycarbonyl, alkoxycarbonylamino, cycloalkylalkoxy, 2-alkyl-2H-tetrazol-5-yl, or 2-haloalkyl-2H-tetrazol-5-yl; $R^1$ is trihaloalkyl, or trihaloalkoxy; n is 0, or 1; and said salt is at least 2.5 times more photostable than its non-ionic parent and is derived from hydrochloric acid, hydrobromic acid, boric acid, phosphoric acid, maleic acid, fumaric acid, phthalic acid, D-glucuronic acid; the sulfonic acid $R^2SO_3H$ where $R^2$ is alkyl, haloalkyl, hydroxyalkyl, D-10-camphoryl, or phenyl optionally substituted with alkyl or halogen; the carboxylic acid $R^3CO_2H$ where $R^3$ is hydrogen, alkyl, trihaloalkyl, carboxyl, phenyl optionally substituted with alkyl or halogen, or pyridyl; the boronic acid $R^4B(OH)_2$ where $R^4$ is alkyl or phenyl optionally substituted with alkyl or halogen; the phosphonic acid $R^5PO_3H_2$ where $R^5$ is alkyl, haloalkenyl, or phenyl optionally substituted with alkyl or halogen; the sulfuric acid $R^6OSO_3H$ where $R^6$ is hydrogen or alkyl; or the alkanoic acid $X$—$(CH_2)_qCO_2H$ where q is 0 to 11, X is halogen, trihaloalkyl, haloalkenyl, cyano, aminocarbonyl, or $CO_2R^7$ where $R^7$ is hydrogen or alkyl.

As set forth in United States Statutory Invention Registration H2,007 compounds of the following structures are reported to be insecticidally active:

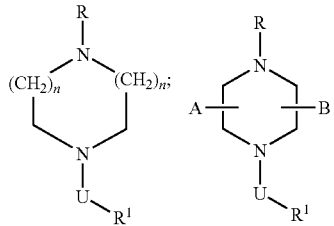

where A and B are independently selected from lower alkyl; U is selected from lower alkylidene, lower alkenylidene, and CH-Z, where Z is selected from hydrogen, lower alkyl, lower cycloalkyl, or phenyl; R is —$CHR^3R^4$ where $R^3$ and $R^4$ are independently selected from phenyl, optionally substituted with halogen, lower alkyl, lower haloalkyl, lower alkoxy, lower haloalkoxy, lower alkenyl, or phenyl; $R^1$ is phenyl, naphthyl, tetrazolylphenyl, phenylcyclopropyl, phenoxyphenyl, benzyloxyphenyl, pyridylphenyl, pyridyloxyphenyl, or thiadiazolyloxyphenyl, each optionally substituted with halogen, cyano, hydroxy, lower alkyl, lower haloalkyl, lower alkoxy, amino, lower dialkylamino, nitro, lower haloalkylsulfonyloxy, lower alkylcarbonyloxy, lower alkylcarbonylamino, lower alkoxycarbonyl, lower alkoxyalkoxycarbonyl, lower cycloalkylalkoxycarbonyl, lower alkoxyalkylalkoxycarbonyl, lower alkoxycarbonylamino, alkoxythiocarbonylamino, lower alkyldithiocarbonylamino, lower dialkyldioxolylalkoxycarbonylamino, or halophenylamino; or lower alkyl substituted with any one of the foregoing cyclic $R^1$ groups; m is 2 or 3; and n is 1, 2, or 3.

As set forth in unexamined Japanese Patent Application 2002-220372 compounds of the following structures are reported to be insecticidally active:

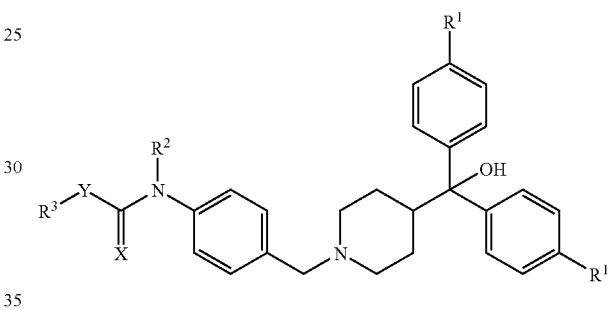

where $R^1$ and $R^2$ are independently selected from hydrogen, halogen, lower alkyl, lower haloalkyl, lower alkoxy, lower haloalkoxy, or lower alkylsulfonyloxy; $R^2$ is selected from hydrogen, lower alkyl, lower alkenyl, lower alkoxyalkyl, or lower alkylcarbonyl; X and Y are independently oxygen or sulfur; $R^3$ is selected from lower alkenyl, or lower alkynyl, which are optionally substituted with hydroxy, halogen, lower alkoxy, lower haloalkoxy, lower alkylthio, lower alkylsulfinyl, lower alkylsulfonyl, lower cycloalkyl, lower alkoxyalkoxy, amino, lower alkylamino, lower dialkylamino, lower alkoxycarbonyl, nitro, cyano, trimethylsilyl, phenyl, or lower cycloalkenyl; and the corresponding N-oxides and salts.

As set forth in PCT Publication WO 02/068392A1 compounds of the following structures are reported to be insecticidally active:

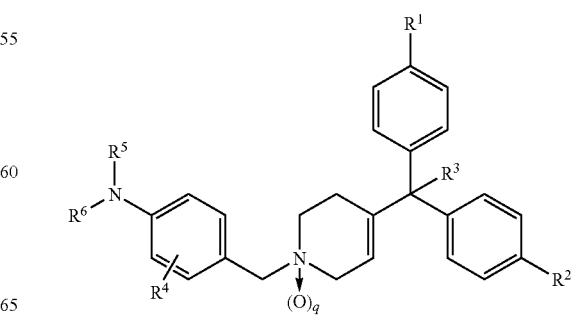

where R[1] and R[2] are independently selected from halogen, $C_1$-$C_6$alkyl, halo$C_1$-$C_6$alkyl, $C_1$-$C_6$alkoxy, halo$C_1$-$C_6$alkoxy, —S(=O)$_p$—R[9], or SF$_5$; R[3] is hydrogen, hydroxy, $C_1$-$C_6$alkoxy, or —OC(=O)—$C_1$-$C_6$alkyl; R[4] is hydrogen, halogen, $C_1$-$C_6$alkyl, halo$C_1$-$C_6$alkyl, $C_1$-$C_6$alkoxy, halo$C_1$-$C_6$alkoxy, or —S(=O)$_p$—R[9], or —SCN; R[5] and R[6] are independently selected from $C_1$-$C_{12}$alkyl, halo$C_1$-$C_{12}$alkyl, $C_2$-$C_{12}$alkenyl, halo$C_2$-$C_{12}$alkenyl, $C_2$-$C_{12}$alkynyl, halo$C_2$-$C_{12}$alkynyl, $C_3$-$C_8$cycloalkyl, —C(=O)—OR[7], —C(=S)—OR[8], —C(=Y)-ZR[8], —S(=O)$_p$—R[9], aryl, aryl$C_1$-$C_6$alkyl, heterocycle, heterocycle$C_1$-$C_6$alkyl, each substituted in the ring from one to five times independently of one another by halogen, hydroxy, cyano, nitro, $C_1$-$C_6$alkyl, halo$C_1$-$C_6$alkyl, $C_1$-$C_6$alkoxy, halo$C_1$-$C_6$alkoxy; or in common together with the nitrogen atom to which they are attached to form a heterocyclic ring which is substituted or unsubstituted; Y is oxygen or sulfur; X is a bond, —NR[10]—, or sulfur; R[7] is $C_1$-$C_6$alkoxy-$C_1$-$C_6$alkyl, $C_1$-$C_6$alkylthio-$C_1$-$C_6$alkyl, $C_1$-$C_6$alkylamino-$C_1$-$C_6$alkyl, $C_3$-$C_6$alkynyl, $C_1$-$C_6$alkyl-S(=O)$_p$—$C_1$-$C_6$alkyl, $C_3$-$C_8$cycloalkyl, aryl, aryl-$C_1$-$C_6$alkyl, heterocyclyl, or heterocyclyl-$C_1$-$C_6$alkyl each substituted in the ring from one to five times independently of one another by halogen, cyano, nitro, $C_1$-$C_6$alkyl, halo$C_1$-$C_6$alkyl, $C_1$-$C_6$alkoxy, or halo$C_1$-$C_6$alkoxy; R[8] is $C_1$-$C_6$alkyl, halo$C_1$-$C_6$alkyl, $C_1$-$C_6$alkoxy-$C_1$-$C_6$alkyl, $C_1$-$C_6$alkylthio-$C_1$-$C_6$alkyl, $C_2$-$C_6$alkenyl, $C_3$-$C_6$alkynyl, $C_1$-$C_6$alkyl-S(=O)$_p$—$C_1$-$C_6$alkyl, $C_3$-$C_8$cycloalkyl, aryl, aryl-$C_1$-$C_6$alkyl, heterocyclyl, or heterocyclyl-$C_1$-$C_6$alkyl, or is $C_3$-$C_8$cycloalkyl, aryl, aryl-$C_1$-$C_6$alkyl, heterocyclyl, or heterocyclyl-$C_1$-$C_6$alkyl each substituted in the ring from one to five times independently of one another by halogen, cyano, nitro, $C_1$-$C_6$alkyl, halo$C_1$-$C_6$alkyl, $C_1$-$C_6$alkoxy, or halo$C_1$-$C_6$alkoxy; R[9] is $C_1$-$C_6$alkyl, $C_3$-$C_8$cycloalkyl, halo$C_1$-$C_6$alkyl, or benzyl; R[10] is hydrogen, $C_1$-$C_6$alkyl, $C_3$-$C_8$cycloalkyl, halo$C_1$-$C_6$alkyl, or benzyl; p is 0, 1, or 2; q is 0 or 1; and, where appropriate, E/Z isomers, E/Z isomer mixtures and/or toutomers, each in free form or in salt form.

As set forth in PCT Publication WO 200020409A1 compounds of the following structures are reported to be insecticidally active:

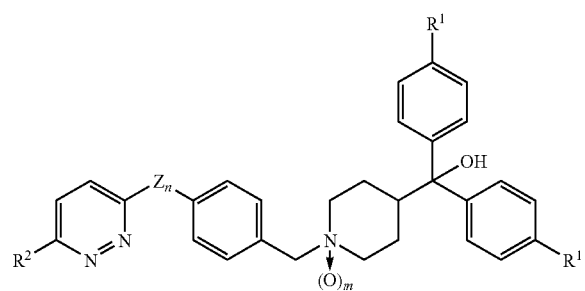

where R[1] is halo, $C_1$-$C_4$alkyl, $C_1$-$C_4$alkoxy, $C_1$-$C_4$haloalkyl, $C_1$-$C_4$haloalkoxy; R[2] is hydrogen, hydroxyl, halo, $C_1$-$C_4$alkyl, $C_1$-$C_4$alkoxy, $C_1$-$C_4$alkoxycarbonyl, $C_1$-$C_4$alkylthio, $C_1$-$C_4$alkylsulfonyl, optionally substituted phenyl or carbamoyl; Z is O or S(O)$_p$, p is 0 or 2; and m and n are 0 or 1.

As set forth in PCT Publication WO 03/022808A1 compounds of the following structures are reported to be insecticidally active:

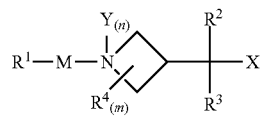

where R[1] is an aryl or heteroaryl that is optionally identically or differently substituted once or several times; R[2] and R[3] are independently selected from aryl or heteroaryl that is optionally identically or differently substituted once or several times, whereby both groups can also be bridged by a common substitutent; M is optionally substituted (CH$_2$)$_l$, where l is 1, 2 or 3, CO or —HNC(O); X is H, OH, halogen, OR[4] or CN; Y is (O), H, OH, OR[4], R[4]; (in the last four groups, in which nitrogen has a positive charge, in combination with a corresponding anion); R[4] is identical or different and represents $C_1$-$C_4$alkyl, $C_1$-$C_4$alkanoyl, $C_1$-$C_4$haloalkyl; m is 0, 1, 2, 3 or 4; and n is 0 or 1.

There is no disclosure or suggestion in any of the citations set forth above of the azacycle derivatives of the present invention.

SUMMARY OF THE INVENTION

In accordance with the present invention, it has now been found that N-substituted azacycle derivatives of Formula I and salts thereof having a substituent X as indicated in the Formula have improved insecticidal activity. The compounds of formula I are represented by the following general formula I:

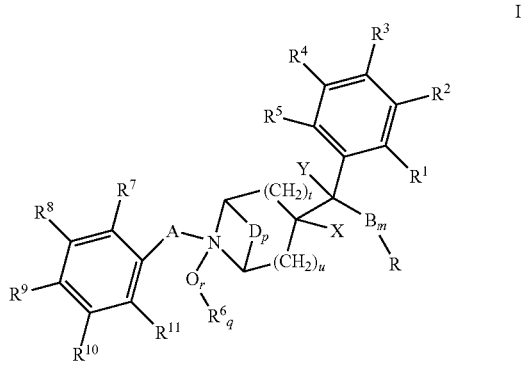

wherein;
m, q, r, t and u are independently selected from 0 or 1; and p is 0, 1, 2, or 3;
X is selected from halogen, hydroxyl, hydroxyalkyl, alkyl, alkoxy, haloalkyl, haloalkoxy, thio, alkylthio, acetoxyalkyl, azidoalkyl, aminoalkyl, acetylaminoalkyl, alkylsulfonyl, alkylsulfoxy, pentahalothio, cyano, nitro, acetyloxy, alkylsulfonyloxy, alkylcarbonyl, alkoxycarbonyl, aryl, or aryloxy;
Y is selected from hydrogen, halogen, alkyl, haloalkyl, hydroxyl, hydroxyalkyl, alkoxy, haloalkoxy, thio, alkylthio, pentahalothio, cyano, nitro, alkylsulfonyl, alkylsulfoxy, alkylsulfonyloxy, alkylcarbonyl, alkoxycarbonyl, aryl, or aryloxy; or
X and Y taken together with —OCR[12]R[13]O—, form a 1,3-dioxolane ring; where
R[12] and R[13] are independently selected from hydrogen, halogen, alkyl, haloalkyl, hydroxyalkyl, alkoxy, haloalkoxy, alkylthio, cyano, nitro, alkylsulfonyloxy, alkylcarbonyl, alkoxycarbonyl, aryl, or aryloxy; or $R^{12}$ and $R^{13}$ taken together with (═O), form 1,3-dioxol-2-one ring;

$R^1, R^2, R^3, R^4$, and $R^5$ are independently selected from hydrogen, halogen, alkyl, haloalkyl, hydroxyl, hydroxyalkyl, alkoxy, haloalkoxy, thio, alkylthio, haloalkylthio, pentahalothio, cyano, nitro, alkylsulfonyl, haloalkylsulfonyl, alkylsulfinyl, haloalkylsulfinyl, alkylsulfonyloxy, haloalkylsulfonyloxy, alkylcarbonyl, alkoxycarbonyl, dialkoxyalkylcarbonyl, alkoxycarbonylamino, alkylaminoxyalkyl, alkoxyiminoalkyl, alkenyloxyiminoalkyl, aryl, aryloxy, dioxanyl, dioxolanyl or either of $R^1$ and $R^2$, or $R^2$ and $R^3$, or $R^3$ and $R^4$, or $R^4$ and $R^5$ taken together with —OC($R^{19}$)$_2$O—, —OC($R^{19}$)$_2$($R^{19}$)$_2$O—, —OC($R^{19}$)$_2$($R^{19}$)$_2$—, —OC($R^{19}$)═N—, or —SC($R^{19}$)═N—, forming a benzo-fused ring, where $R^{19}$ is hydrogen, halogen, alkyl or haloalkyl; and, wherein at least one of $R^1, R^2, R^3, R^4$, and $R^5$ is other than hydrogen;

$R^7, R^8, R^9, R^{10}$, and $R^{11}$ are independently selected from hydrogen, halogen, alkyl, hydroxy, hydroxyalkyl, hydroxyalkoxy, alkoxy, alkoxyalkyl, alkoxyiminoalkyl, haloalkoxyiminoalkyl, cyanoalkoxyiminoalkyl, cyanoiminothioalkylamino, alkenyloxyiminoalkyl, alkynyloxyiminoalkyl, cycloalkoxy, cycloalkylalkoxy, phenoxy, alkoxycarbonylphenoxy, alkoxyalkoxy, alkoxyalkoxyalkoxy, alkylthio, alkylsulfonyl, alkylaminosulfonyl, dialkylaminosulfonyl, cycloalkylaminosulfonyl, alkenyloxy, alkynyloxy, haloalkenyloxy, alkylsulfonyloxy, optionally substituted arylalkoxy, cyano, nitro, amino, alkylamino, alkylcarbonylamino, alkoxycarbonylamino, cycloalkylalkoxycarbonylamino, alkenyloxycarbonylamino, alkynyloxycarbonylamino, haloalkylcarbonylamino, alkoxyalkoxycarbonylamino, alkoxycarbonylamino, alkoxycarbonyloxy, alkenylaminocarbonyloxy, alkynylaminocarbonyloxy, (alkyl)(alkoxycarbonyl)amino, alkylsulfonylamino, optionally substituted (heteroaryl)(alkoxycarbonyl)amino, optionally substituted arylcarbonylamino, alkoxycarbonyl, alkylaminocarbonyloxy, alkylaminocarbonylamino, dialkylaminocarbonylamino, alkylamino(thiocarbonyl)amino, dialkylphosphoroureidyl, acetoxyalkoxy, sulfonyloxyalkoxy, dialkoxyalkoxy, trialkoxyalkoxy, dialkoxyalkylacetal, trialkoxymethylorthoester, cyclic acetal, optionally substituted cyclic acetal, optionally substituted thienyl, optionally substituted 1,3-thiazolylalkoxy, optionally substituted aryl, optionally substituted aryloxy, optionally substituted aryloxyalkyl, optionally substituted arylaminocarbonyloxy, optionally substituted arylalkoxycarbonylamino, optionally substituted heteroaryl, optionally substituted heteroaryloxy, optionally substituted pyrrolyl, optionally substituted pyrazolyl, optionally substituted pyrazinyloxy, optionally substituted cycloalkylcarbonylamino, optionally substituted 1,3-oxazolinyl, optionally substituted 1,3-oxazolinyloxy, optionally substituted 1,3-oxazoliny-lamino, optionally substituted 1,2,4-triazolyl, optionally substituted 1,2,3-thiadiazolyl, optionally substituted 1,2,5-thiadiazolyl, optionally substituted 1,2,5-thiadiazolyloxy, optionally substituted 2H-tetrazolyl, optionally substituted pyridyl, optionally substituted pyridyloxy, optionally substituted pyridylamino, optionally substituted pyrimidinyl, optionally substituted pyrimidinyloxy, optionally substituted 3,4,5,6-tetrahydropyrimidinyloxy, optionally substituted pyridazinyloxy, or optionally substituted 1,2,3,4-tetrahydronaphthalenyl, wherein the optional substituent is selected from one or more of halogen, alkyl, haloalkyl, alkoxy, cyano, nitro, amino, alkylcarbonyl, alkoxycarbonyl, alkoxyiminoalkyl, dialkylacetal, alkylthiol, alkylsulfoxide, or alkoxycarbonylamino; and, wherein at least one of $R^7, R^8, R^9, R^{10}$, and $R^{11}$ is other than hydrogen;

R is alkyl, cycloalkyl, alkenyl, alkoxycarbonyl, optionally substituted pyrid-2-yl wherein the optional substituent is selected from hydrogen, halogen, haloalkoxy or haloalkyl, or substituted phenyl have the following structure,

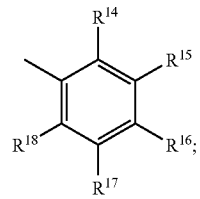

where
$R^{14}, R^{15}, R^{16}, R^{17}$, and $R^{18}$ are independently selected from hydrogen, halogen, alkyl, haloalkyl, hydroxyl, hydroxyalkyl, alkoxy, haloalkoxy, thio, alkylthio, haloalkylthio, pentahalothio, cyano, nitro, alkylsulfonyl, haloalkylsulfonyl, alkylsulfinyl, haloalkylsulfinyl, alkylsulfonyloxy, haloalkylsulfonyloxy, alkylcarbonyl, alkoxycarbonyl, dialkoxyalkylcarbonyl, alkoxycarbonylamino, alkylaminoxyalkyl, alkoxyiminoalkyl, alkenyloxyiminoalkyl, aryl, aryloxy, dioxanyl, dioxolanyl or either of $R^{14}$ and $R^{15}$, or $R^{15}$ and $R^{16}$, or $R^{16}$ and $R^{17}$, or $R^{17}$ and $R^{18}$ taken together with —OC($R^{19}$)$_2$O—, —OC($R^{19}$)$_2$($R^{19}$)$_2$O—, —OC($R^{19}$)$_2$($R^{19}$)$_2$—, —OC($R^{19}$)═N—, or —SC($R^{19}$)═N—, forming a benzo-fused ring, where $R^{19}$ is hydrogen, halogen, alkyl or haloalkyl; and, wherein at least one of $R^{14}, R^{15}, R^{16}, R^{17}$, and $R^{18}$ is other than hydrogen;

A is selected from —CH$_2$—, —CH$_2$CH$_2$—, —CH$_2$CH$_2$CH$_2$—, —OCH$_2$CH$_2$—, —OCH$_2$CH$_2$CH$_2$—, —OCH$_2$CH$_2$CH$_2$CH$_2$—, —OCH$_2$CH(OH)CH$_2$—, —NHCH$_2$CH$_2$—, —N(CH$_3$)CH$_2$CH$_2$—, —N[C(═O)CH$_3$]CH$_2$CH$_2$—, or —N[C(═O)OCH$_3$]CH$_2$CH$_2$—;

B is selected from —O—, —S—, —CH$_2$O—, —OCH$_2$—, —OC(═O)NH—, —OC(═O)O—, or —NHSO$_2$—;

when p is 1, 2, or 3;

D is —CH$_2$—;

$R^6$ is selected from alkyl, haloalkyl, hydroxyalkyl, alkoxyalkyl, dialkylaminoalkyl, alkylaminocarbonyloxyalkyl, alkylthioalkyl, alkylsulfonylalkyl, alkylcarbonyloxyalkyl, alkoxycarbonylalkyl, carboxyalkyl, arylalkyl, arylcarbonyl, sulfonato, or sulfonatoalkyl, and may bear a negative charge resulting in an inner salt; and a separate ion is chloride, bromide, iodide, or an alkyl or phenyl sulfate or sulfonate; and agriculturally-acceptable salts thereof.

The present invention is also directed to compositions containing an insecticidally effective amount of at least one of a compound of formula I, and optionally, an effective amount of at least one of a second compound, with at least one agriculturally acceptable extender or adjuvant.

The present invention is also directed to methods of controlling insects, where control is desired, which comprise applying an insecticidally effective amount of the above composition to the locus of crops, or other areas where insects are present or are expected to be present. Other aspects of the present invention will become apparent.

DETAILED DESCRIPTION OF THE INVENTION

One aspect of the present invention relates to certain new and useful compounds, namely certain novel N-substituted azacycle derivatives as depicted in general formula I:

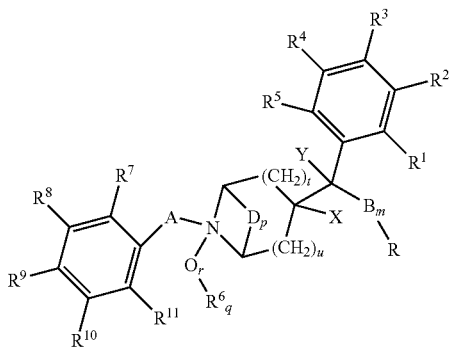

wherein;

m, q, r, t and u are independently selected from 0 or 1; and p is 0, 1, 2, or 3;

X is selected from halogen, hydroxyl, hydroxyalkyl, alkyl, alkoxy, haloalkyl, haloalkoxy, thio, alkylthio, acetoxyalkyl, azidoalkyl, aminoalkyl, acetylaminoalkyl, alkylsulfonyl, alkylsulfoxy, pentahalothio, cyano, nitro, acetyloxy, alkylsulfonyloxy, alkylcarbonyl, alkoxycarbonyl, aryl, or aryloxy;

Y is selected from hydrogen, halogen, alkyl, haloalkyl, hydroxyl, hydroxyalkyl, alkoxy, haloalkoxy, thio, alkylthio, pentahalothio, cyano, nitro, alkylsulfonyl, alkylsulfoxy, alkylsulfonyloxy, alkylcarbonyl, alkoxycarbonyl, aryl, or aryloxy; or X and Y taken together with —OCR$^{12}$R$^{13}$O—, form a 1,3-dioxolane ring; where R$^{12}$ and R$^{13}$ are independently selected from hydrogen, halogen, alkyl, haloalkyl, hydroxyalkyl, alkoxy, haloalkoxy, alkylthio, cyano, nitro, alkylsulfonyloxy, alkylcarbonyl, alkoxycarbonyl, aryl, or aryloxy; or R$^{12}$ and R$^{13}$ taken together with (=O), form 1,3-dioxol-2-one ring;

R$^1$, R$^2$, R$^3$, R$^4$, and R$^5$ are independently selected from hydrogen, halogen, alkyl, haloalkyl, hydroxyl, hydroxyalkyl, alkoxy, haloalkoxy, thio, alkylthio, haloalkylthio, pentahalothio, cyano, nitro, alkylsulfonyl, haloalkylsulfonyl, alkylsulfinyl, haloalkylsulfinyl, alkylsulfonyloxy, haloalkylsulfonyloxy, alkylcarbonyl, alkoxycarbonyl, dialkoxyalkylcarbonyl, alkoxycarbonylamino, alkylaminoxyalkyl, alkoxyiminoalkyl, alkenyloxyiminoalkyl, aryl, aryloxy, dioxanyl, dioxolanyl or either of R$^1$ and R$^2$, or R$^2$ and R$^3$, or R$^3$ and R$^4$, or R$^4$ and R$^5$ taken together with —OC(R$^{19}$)$_2$O—, —OC(R$^{19}$)$_2$(R$^{19}$)$_2$O—, —OC(R$^{19}$)$_2$(R$^{19}$)$_2$—, —OC(R$^{19}$)=N—, or —SC(R$^{19}$)=N—, forming a benzo-fused ring, where R$^{19}$ is hydrogen, halogen, alkyl or haloalkyl; and, wherein at least one of R$^1$, R$^2$, R$^3$, R$^4$, and R$^5$ is other than hydrogen;

R$^7$, R$^8$, R$^9$, R$^{10}$, and R$^{11}$ are independently selected from hydrogen, halogen, alkyl, hydroxy, hydroxyalkyl, hydroxyalkoxy, alkoxy, alkoxyalkyl, alkoxyiminoalkyl, haloalkoxyiminoalkyl, cyanoalkoxyiminoalkyl, cyanoiminothioalkylamino, alkenyloxyiminoalkyl, alkynyloxyiminoalkyl, cycloalkoxy, cycloalkylalkoxy, phenoxy, alkoxycarbonylphenoxy, alkoxyalkoxy, alkoxyalkoxyalkoxy, alkylthio, alkylsulfonyl, alkylaminosulfonyl, dialkylaminosulfonyl, cycloalkylaminosulfonyl, alkenyloxy, alkynyloxy, haloalkenyloxy, alkylsulfonyloxy, optionally substituted arylalkoxy, cyano, nitro, amino, alkylamino, alkylcarbonylamino, alkoxycarbonylamino, cycloalkylalkoxycarbonylamino, alkenyloxycarbonylamino, alkynyloxycarbonylamino, haloalkylcarbonylamino, alkoxyalkoxycarbonylamino, alkoxycarbonylamino, alkoxycarbonyloxy, alkenylaminocarbonyloxy, alkynylaminocarbonyloxy, (alkyl)(alkoxycarbonyl)amino, alkylsulfonylamino, optionally substituted (heteroaryl)(alkoxycarbonyl)amino, optionally substituted arylcarbonylamino, alkoxycarbonyl, alkylaminocarbonyloxy, alkylaminocarbonylamino, dialkylaminocarbonylamino, alkylamino(thiocarbonyl)amino, dialkylphosphoroureidyl, acetoxyalkoxy, sulfonyloxyalkoxy, dialkoxyalkoxy, trialkoxyalkoxy, dialkoxyalkylacetal, trialkoxymethylorthoester, cyclic acetal, optionally substituted cyclic acetal, optionally substituted thienyl, optionally substituted 1,3-thiazolylalkoxy, optionally substituted aryl, optionally substituted aryloxy, optionally substituted aryloxyalkyl, optionally substituted arylaminocarbonyloxy, optionally substituted arylalkoxycarbonylamino, optionally substituted heteroaryl, optionally substituted heteroaryloxy, optionally substituted pyrrolyl, optionally substituted pyrazolyl, optionally substituted pyrazinyloxy, optionally substituted cycloalkylcarbonylamino, optionally substituted 1,3-oxazolinyl, optionally substituted 1,3-oxazolinyloxy, optionally substituted 1,3-oxazolinylamino, optionally substituted 1,2,4-triazolyl, optionally substituted 1,2,3-thiadiazolyl, optionally substituted 1,2,5-thiadiazolyl, optionally substituted 1,2,5-thiadiazolyloxy, optionally substituted 2H-tetrazolyl, optionally substituted pyridyl, optionally substituted pyridyloxy, optionally substituted pyridylamino, optionally substituted pyrimidinyl, optionally substituted pyrimidinyloxy, optionally substituted 3,4,5,6-tetrahydropyrimidinyloxy, optionally substituted pyridazinyloxy, or optionally substituted 1,2,3,4-tetrahydronaphthalenyl, wherein the optional substituent is selected from one or more of halogen, alkyl, haloalkyl, alkoxy, cyano, nitro, amino, alkylcarbonyl, alkoxycarbonyl, alkoxyiminoalkyl, dialkylacetal, alkylthiol, alkylsulfoxide, or alkoxycarbonylamino; and, wherein at least one of R$^7$, R$^8$, R$^9$, R$^{10}$, and R$^{11}$ is other than hydrogen;

R is alkyl, cycloalkyl, alkenyl, alkoxycarbonyl, optionally substituted pyrid-2-yl wherein the optional substituent is selected from hydrogen, halogen, haloalkoxy or haloalkyl, or substituted phenyl have the following structure,

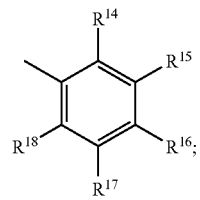

where

R$^{14}$, R$^{15}$, R$^{16}$, R$^{17}$, and R$^{18}$ are independently selected from hydrogen, halogen, alkyl, haloalkyl, hydroxyl, hydroxyalkyl, alkoxy, haloalkoxy, thio, alkylthio, haloalkylthio, pentahalothio, cyano, nitro, alkylsulfonyl, haloalkylsulfonyl, alkylsulfinyl, haloalkylsulfinyl, alkylsulfonyloxy, haloalkylsulfonyloxy, alkylcarbonyl, alkoxycarbonyl, dialkoxyalkylcarbonyl, alkoxycarbonylamino, alkylaminoxyalkyl, alkoxyiminoalkyl, alkenyloxyiminoalkyl, aryl, aryloxy, dioxanyl, dioxolanyl or either of R$^{14}$ and R$^{15}$, or R$^{15}$ and R$^{16}$, or R$^{16}$ and R$^{17}$, or R$^{17}$ and R$^{18}$ taken together with —OC(R$^{19}$)$_2$O—, —OC(R$^{19}$)$_2$(R$^{19}$)$_{2\text{-}O}$—, —OC(R$^{19}$)$_2$ (R$^{19}$)$_2$—, —OC(R$^{19}$)=N—, or —SC(R$^{19}$)=N—, forming a benzo-fused ring, where R$^{19}$ is hydrogen, halogen, alkyl or haloalkyl; and, wherein at least one of $R^{14}$, $R^{15}$, $R^{16}$, $R^{17}$, and $R^{18}$ is other than hydrogen;

A is selected from —CH$_2$—, —CH$_2$CH$_2$—, —CH$_2$CH$_2$CH$_2$—, —OCH$_2$CH$_2$—, —OCH$_2$CH$_2$CH$_2$—, —OCH$_2$CH$_2$CH$_2$CH$_2$—, —OCH$_2$CH(OH)CH$_2$—, —NHCH$_2$CH$_2$—, —N(CH$_3$)CH$_2$CH$_2$—, —N[C(=O)CH$_3$]CH$_2$CH$_2$—, or —N[C(=O)OCH$_3$]CH$_2$CH$_2$—;

B is selected from —O—, —S—, —CH$_2$O—, —OCH$_2$—, —OC(=O)NH—, —OC(=O)O—, or —NHSO$_2$—;

when p is 1, 2, or 3;

D is —CH$_2$—;

$R^6$ is selected from alkyl, haloalkyl, hydroxyalkyl, alkoxyalkyl, dialkylaminoalkyl, alkylaminocarbonyloxyalkyl, alkylthioalkyl, alkylsulfonylalkyl, alkylcarbonyloxyalkyl, alkoxycarbonylalkyl, carboxyalkyl, arylalkyl, arylcarbonyl, sulfonato, or sulfonatoalkyl, and may bear a negative charge resulting in an inner salt; and a separate ion is chloride, bromide, iodide, or an alkyl or phenyl sulfate or sulfonate; and agriculturally-acceptable salts thereof.

Within the scope set forth above, preferred compounds of the present invention are those of formula I wherein m, q and p are 0; t and u are 1; A is —CH$_2$—; X is selected from halogen, hydroxyl or alkoxycarbonyl; Y is selected from hydrogen, halogen or hydroxyl; $R^1$, $R^2$, $R^3$ and $R^4$ are independently selected from hydrogen, halogen, alkyl, alkoxy, haloalkyl, haloalkoxy, —CH$_2$(OH)CH$_3$, —CH=NOC$_2$H$_5$, 1,3-dioxolan-2-yl, or $R^2$ and $R^3$ taken together with —OCF$_2$O—; $R^5$ is hydrogen; $R^7$, $R^{10}$ and $R^{11}$ are hydrogen; $R^8$ is selected from hydrogen, halogen, alkyl or alkoxy; $R^9$ is selected from alkoxy, alkoxyalkoxy, alkoxyalkoxyalkoxy, cyclopropylmethoxy, 2-halophenoxy, 3-halophenoxy, 4-halophenoxy, pyrimidin-2-yl, pyrid-2-yl, 3-halo-pyrid-2-yl, 3-alkyl-pyrid-2-yloxy, 4-alkyl-pyrid-2-yloxy, 5-alkyl-pyrid-2-yloxy, 6-alkyl-pyrid-2-yloxy, 3-halo-pyrid-2-yloxy, 3-trihaloalkyl-pryid-2-yloxy, 3-cyano-pyrid-2-yloxy, 5-cyano-pyrid-2-yloxy, 6-dialkoxyalkyl-pyrid-2-yloxy, pyrid-2-yloxy, CO$_2$CH(CH$_3$)$_2$, —CH=NOCH$_3$, —CH=NOC$_2$H$_5$, —CH=NOCH$_2$CF$_3$, —CH=NOCH$_2$CH=CH$_2$, —CH=NOCH$_2$CN, —CH=NOCH(CH$_3$)$_2$, —CH=NOCH$_2$C≡CH, —CH=NOCH$_2$CH$_2$F, —CH=NOCH$_2$CH$_2$OCH$_3$, —CH=NOCH$_2$OC$_2$H$_5$, —CH=NOCH$_2$CH$_2$OCH$_2$CH$_2$OCH$_3$, —NHCO$_2$CH$_3$, —NHCO$_2$C$_2$H$_5$, —NHCO$_2$CH(CH$_3$)$_2$, —NHCO$_2$CH$_2$-c-C$_3$H$_5$, —CH(OH)C$_6$H$_5$-p-Cl, —OC(=O)NHCH$_3$, —OC(=O)NHC$_2$H$_5$, —OC(=O)NHCH(CH$_3$)$_2$, —NHC(SCH$_3$)=NCN, pyrimidin-2-yloxy, 6-halo-pyridazin-3yloxy, 6-alkoxy-pyridazin-3yloxy, 6-alkyl-pyridazin-3yloxy, 2-alkyl-2H-tetrazol-5-yl, 1,3-dioxan-2-yl or 5,5-dialkyl-1,3-dioxan-2-yl; and R is phenyl substituted with $R^{14}$, $R^{15}$, $R^{16}$, $R^{17}$, and $R^{18}$,

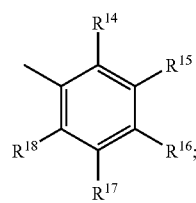

where $R^{14}$, $R^{15}$, $R^{16}$ and $R^{17}$ are independently selected from halogen, haloalkyl, haloalkoxy or $R^{15}$ and $R^{16}$ taken together with —OCF$_2$O—; and $R^{18}$ is hydrogen.

Within the scope set forth above, more preferred compounds of the present invention are those of formula I wherein X is selected from halogen, —CO$_2$C$_2$H$_5$ or hydroxyl; and $R^9$ is selected from —OC$_2$H$_5$, —OC$_3$H$_7$, —OCH(CH$_3$)$_2$, —OCH$_2$CH$_2$OCH$_3$, —OCH$_2$CH$_2$CH$_2$OCH$_3$, cyclopropylmethoxy, 2-chlorophenoxy, 3-chlorophenoxy, 4-chlorophenoxy, pyrimidin-2-yl, pyrid-2-yl, 3-chloro-pyrid-2-yl, 3-methyl-pyrid-2-yloxy, 4-methyl-pyrid-2-yloxy, 5-methyl-pyrid-2-yloxy, 6-methyl-pyrid-2-yloxy, 3-chloro-pyrid-2-yloxy, 3-trifluoromethyl-pryid-2-yloxy, 3-cyano-pyrid-2-yloxy, 5-cyano-pyrid-2-yloxy, 6-dimethoxymethyl-pyrid-2-yloxy, pyrid-2-yloxy, —CO$_2$CH(CH$_3$)$_2$, —CH=NOCH$_3$, —CH=NOC$_2$H$_5$, —CH=NOCH$_2$CF$_3$, —CH=NOCH$_2$CH=CH$_2$, —CH=NOCH$_2$CN, —CH=NOCH(CH$_3$)$_2$, —CH=NOCH$_2$C≡CH, —CH=NOCH$_2$CH$_2$F, —CH=NOCH$_2$CH$_2$OCH$_3$, —CH=NOCH$_2$OC$_2$H$_5$, —CH=NOCH$_2$CH$_2$OCH$_2$CH$_2$OCH$_3$, —NHCO$_2$CH$_3$, —NHCO$_2$C$_2$H$_5$, —NHCO$_2$CH(CH$_3$)$_2$, —NHCO$_2$CH$_2$-c-C$_3$H$_5$, —CH(OH)C$_6$H$_5$-p-Cl, —OC(=O)NHCH$_3$, —OC(=O)NHC$_2$H$_5$, —OC(=O)NHCH(CH$_3$)$_2$, —NHC(SCH$_3$)=NCN, pyrimidin-2-yloxy, 6-chloro-pyridazin-3yloxy, 6-methoxy-pyridazin-3yloxy, 6-methyl-pyridazin-3yloxy, 2-methyl-2H-tetrazol-5-yl, 2-ethyl-2H-tetrazol-5-yl, 1,3-dioxan-2-yl or 5,5-dimethyl-1,3-dioxan-2-yl.

Within the scope set forth above, even more preferred compounds of the present invention are those of formula I wherein X is selected from fluorine, —CO$_2$C$_2$H$_5$ or hydroxyl; Y is selected from hydrogen, fluorine, chlorine or hydroxyl; $R^1$, $R^2$, $R^3$ and $R^4$ are independently selected from hydrogen, halogen, alkyl, tert-butyl, methoxy, trifluoromethyl, difluoromethoxy, trifluoromethoxy, —OCF$_2$CHFCF$_3$, —CH$_2$(OH)CH$_3$, —CH=NOC$_2$H$_5$, 1,3-dioxolan-2-yl, or $R^2$ and $R^3$ taken together with —OCF$_2$O—; $R^5$ is hydrogen; $R^9$ is selected from —OCH$_2$CH$_2$OCH$_3$, —CH=NOCH$_3$, —CH=NOC$_2$H$_5$, —CH=NOCH$_2$CN, —CH=NOCH$_2$CH$_2$OCH$_3$, —NHCO$_2$CH(CH$_3$)$_2$, —OC(=O)NHCH(CH$_3$)$_2$, pyrimidin-2-yl, pyrid-2-yl, 3-chloro-pyrid-2-yl, 3-methyl-pyrid-2-yloxy, 4-methyl-pyrid-2-yloxy, 5-methyl-pyrid-2-yloxy, 6-methyl-pyrid-2-yloxy, 3-chloro-pyrid-2-yloxy, 3-trifluoromethyl-pryid-2-yloxy, 3-cyano-pyrid-2-yloxy, 5-cyano-pyrid-2-yloxy, 6-dimethoxymethyl-pyrid-2-yloxy, pyrid-2-yloxy, pyrimidin-2-yloxy, 6-chloro-pyridazin-3yloxy, 6-methoxy-pyridazin-3yloxy or 6-methyl-pyridazin-3yloxy; and R is phenyl substituted with $R^{14}$, $R^{15}$, $R^{16}$, $R^{17}$, and $R^{18}$,

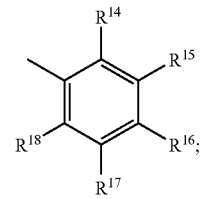

where $R^{14}$, $R^{15}$, $R^{16}$ and $R^{17}$ are independently selected from fluorine, chlorine, trifluoromethyl, difluoromethoxy, trifluoromethoxy, —OCF$_2$CHFCF$_3$ or $R^{15}$ and $R^{16}$ taken together with —OCF$_2$O—.

Within the scope set forth above, most preferred compounds of the present invention are those of formula I wherein X is hydroxyl; Y is hydrogen; $R^3$ is haloalkoxy; $R^9$ is selected —OCH$_2$CH$_2$OCH$_3$, —CH=NOCH$_3$, —CH=NOC$_2$H$_5$, —CH=NOCH$_2$CN, —CH=NOCH$_2$CH$_2$OCH$_3$, —NHCO$_2$CH(CH$_3$)$_2$, OC(=O)NHCH(CH$_3$)$_2$, pyrid-2-yloxy, pyrid-2-yl, 3-cyano-pyrid-2-yloxy, 5-methyl-pyrid-2-yloxy, pyrimidin-2-yloxy, pyrimidin-2-yl, 6-chloro-pyridazin-3-yloxy or 6-methoxy-pyridazin-3-yloxy; and R$^{16}$ is haloalkoxy.

An embodiment of the present invention is a compound of formula I:

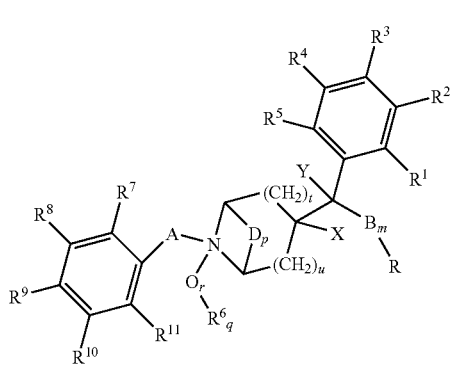

wherein;
m, q and r are independently selected from 0 or 1; t and u are 1; and p is 0;

X is selected from halogen, hydroxyl, hydroxyalkyl, alkyl, alkoxy, haloalkyl, haloalkoxy, thio, alkylthio, acetoxyalkyl, azidoalkyl, aminoalkyl, acetylaminoalkyl, alkylsulfonyl, alkylsulfoxy, pentahalothio, cyano, nitro, acetyloxy, alkylsulfonyloxy, alkylcarbonyl, alkoxycarbonyl, aryl, or aryloxy;

Y is selected from hydrogen, halogen, alkyl, haloalkyl, hydroxyl, hydroxyalkyl, alkoxy, haloalkoxy, thio, alkylthio, pentahalothio, cyano, nitro, alkylsulfonyl, alkylsulfoxy, alkylsulfonyloxy, alkylcarbonyl, alkoxycarbonyl, aryl, or aryloxy; or X and Y taken together with —OCR$^{12}$R$^{13}$O—, form a 1,3-dioxolane ring; where
R$^{12}$ and R$^{13}$ are independently selected from hydrogen, halogen, alkyl, haloalkyl, hydroxyalkyl, alkoxy, haloalkoxy, alkylthio, cyano, nitro, alkylsulfonyloxy, alkylcarbonyl, alkoxycarbonyl, aryl, or aryloxy; or
R$^{12}$ and R$^{13}$ taken together with (=O), form 1,3-dioxol-2-one ring;

R$^1$, R$^2$, R$^3$, R$^4$, and R$^5$ are independently selected from hydrogen, halogen, alkyl, haloalkyl, hydroxyl, hydroxyalkyl, alkoxy, haloalkoxy, thio, alkylthio, haloalkylthio, pentahalothio, cyano, nitro, alkylsulfonyl, haloalkylsulfonyl, alkylsulfinyl, haloalkylsulfinyl, alkylsulfonyloxy, haloalkylsulfonyloxy, alkylcarbonyl, alkoxycarbonyl, dialkoxyalkylcarbonyl, alkoxycarbonylamino, alkylaminoxyalkyl, alkoxyiminoalkyl, alkenyloxyiminoalkyl, aryl, aryloxy, dioxanyl, dioxolanyl or either of R$^1$ and R$^2$, or R$^2$ and R$^3$, or R$^3$ and R$^4$, or R$^4$ and R$^5$ taken together with —OC(R$^{19}$)$_2$O—, —OC(R$^{19}$)$_2$(R$^{19}$)$_2$O—, —OC(R$^{19}$)$_2$(R$^{19}$)$_2$—, —OC(R$^{19}$)=N—, or —SC(R$^{19}$)=N—, forming a benzo-fused ring, where R$^{19}$ is hydrogen, halogen, alkyl or haloalkyl; and, wherein at least one of R$^1$, R$^2$, R$^3$, R$^4$, and R$^5$ is other than hydrogen;

R$^7$, R$^8$, R$^9$, R$^{10}$, and R$^{11}$ are independently selected from hydrogen, halogen, alkyl, hydroxy, hydroxyalkyl, hydroxyalkoxy, alkoxy, alkoxyalkyl, alkoxyiminoalkyl, haloalkoxyiminoalkyl, cyanoalkoxyiminoalkyl, cyanoiminothioalkylamino, alkenyloxyiminoalkyl, alkynyloxyiminoalkyl, cycloalkoxy, cycloalkylalkoxy, phenoxy, alkoxycarbonylphenoxy, alkoxyalkoxy, alkoxyalkoxyalkyl, alkylthio, alkylsulfonyl, alkylaminosulfonyl, dialkylaminosulfonyl, cycloalkylaminosulfonyl, alkenyloxy, alkynyloxy, haloalkenyloxy, alkylsulfonyloxy, optionally substituted arylalkoxy, cyano, nitro, amino, alkylamino, alkylcarbonylamino, alkoxycarbonylamino, cycloalkylalkoxycarbonylamino, alkenyloxycarbonylamino, alkynyloxycarbonylamino, haloalkylcarbonylamino, alkoxyalkoxycarbonylamino, alkoxycarbonylamino, alkoxycarbonyloxy, alkenylaminocarbonyloxy, alkynylaminocarbonyloxy, (alkyl)(alkoxycarbonyl)amino, alkylsulfonylamino, optionally substituted (heteroaryl)(alkoxycarbonyl)amino, optionally substituted arylcarbonylamino, alkoxycarbonyl, alkylaminocarbonyloxy, alkylaminocarbonylamino, dialkylaminocarbonylamino, alkylamino(thiocarbonyl)amino, dialkylphosphoroureidyl, acetoxyalkoxy, sulfonyloxyalkoxy, dialkoxyalkoxy, trialkoxyalkoxy, dialkoxyalkylacetal, trialkoxymethylorthoester, cyclic acetal, optionally substituted cyclic acetal, optionally substituted thienyl, optionally substituted 1,3-thiazolylalkoxy, optionally substituted aryl, optionally substituted aryloxy, optionally substituted aryloxyalkyl, optionally substituted arylaminocarbonyloxy, optionally substituted arylalkoxycarbonylamino, optionally substituted heteroaryl, optionally substituted heteroaryloxy, optionally substituted pyrrolyl, optionally substituted pyrazolyl, optionally substituted pyrazinyloxy, optionally substituted cycloalkylcarbonylamino, optionally substituted 1,3-oxazolinyl, optionally substituted 1,3-oxazolinyloxy, optionally substituted 1,3-oxazolinylamino, optionally substituted 1,2,4-triazolyl, optionally substituted 1,2,3-thiadiazolyl, optionally substituted 1,2,5-thiadiazolyl, optionally substituted 1,2,5-thiadiazolyloxy, optionally substituted 2H-tetrazolyl, optionally substituted pyridyl, optionally substituted pyridyloxy, optionally substituted pyridylamino, optionally substituted pyrimidinyl, optionally substituted pyrimidinyloxy, optionally substituted 3,4,5,6-tetrahydropyrimidinyloxy, optionally substituted pyridazinyloxy, or optionally substituted 1,2,3,4-tetrahydronaphthalenyl, wherein the optional substituent is selected from one or more of halogen, alkyl, haloalkyl, alkoxy, cyano, nitro, amino, alkylcarbonyl, alkoxycarbonyl, alkoxyiminoalkyl, dialkylacetal, alkylthiol, alkylsulfoxide, or alkoxycarbonylamino; and, wherein at least one of R$^7$, R$^8$, R$^9$, R$^{10}$, and R$^{11}$ is other than hydrogen;

R is alkyl, cycloalkyl, alkenyl, alkoxycarbonyl, optionally substituted pyrid-2-yl wherein the optional substituent is selected from hydrogen, halogen, haloalkoxy or haloalkyl, or substituted phenyl have the following structure,

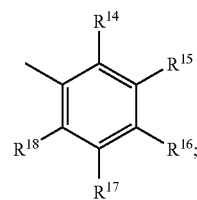

where
R$^{14}$, R$^{15}$, R$^{16}$, R$^{17}$, and R$^{18}$ are independently selected from hydrogen, halogen, alkyl, haloalkyl, hydroxyl, hydroxyalkyl, alkoxy, haloalkoxy, thio, alkylthio, haloalkylthio, pentahalothio, cyano, nitro, alkylsulfonyl, haloalkylsulfonyl, alkylsulfinyl, haloalkylsulfinyl, alkylsulfonyloxy, haloalkylsulfonyloxy, alkylcarbonyl, alkoxycarbonyl, dialkoxyalkylcarbonyl, alkoxycarbonylamino, alkylaminoxyalkyl, alkoxyiminoalkyl, alkenyloxyiminoalkyl, aryl, aryloxy, dioxanyl, dioxolanyl or either of $R^{14}$ and $R^{15}$, or $R^{15}$ and $R^{16}$, or $R^{16}$ and $R^{17}$, or $R^{17}$ and $R^{18}$ taken together with —OC$(R^{19})_2$O—, —OC$(R^{19})_2(R^{19})_2$O—, —OC$(R^{19})_2(R^{19})_2$—, —OC$(R^{19})$=N—, or —SC$(R^{19})$=N—, forming a benzo-fused ring, where $R^{19}$ is hydrogen, halogen, alkyl or haloalkyl; and, wherein at least one of $R^{14}$, $R^{15}$, $R^{16}$, $R^{17}$, and $R^{18}$ is other than hydrogen;

A is selected from —CH$_2$—, —CH$_2$CH$_2$—, —CH$_2$CH$_2$CH$_2$—, —OCH$_2$CH$_2$—, —OCH$_2$CH$_2$CH$_2$—, —OCH$_2$CH$_2$CH$_2$CH$_2$—, —OCH$_2$CH(OH)CH$_2$—, —NHCH$_2$CH$_2$—, —N(CH$_3$)CH$_2$CH$_2$—, —N[C(=O)CH$_3$]CH$_2$CH$_2$—, or —N[C(=O)OCH$_3$]CH$_2$CH$_2$—;

B is selected from —O—, —S—, —CH$_2$O—, —OCH$_2$—, —OC(=O)NH—, —OC(=O)O—, or —NHSO$_2$—;

$R^6$ is selected from alkyl, haloalkyl, hydroxyalkyl, alkoxyalkyl, dialkylaminoalkyl, alkylaminocarbonyloxyalkyl, alkylthioalkyl, alkylsulfonylalkyl, alkylcarbonyloxyalkyl, alkoxycarbonylalkyl, carboxyalkyl, arylalkyl, arylcarbonyl, sulfonato, or sulfonatoalkyl, and may bear a negative charge resulting in an inner salt; and a separate ion is chloride, bromide, iodide, or an alkyl or phenyl sulfate or sulfonate.

Another embodiment of the present invention is a compound of formula I:

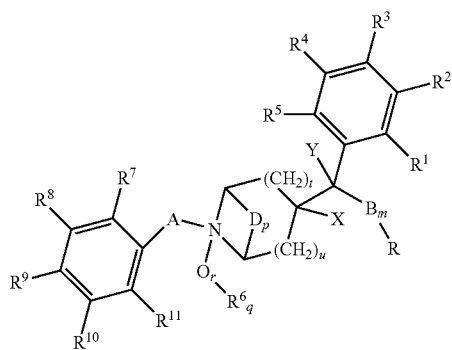

wherein;
r is selected from 0 or 1; m, q and p are 0; t and u are 1;
A is —CH$_2$—;
X is selected from halogen or hydroxyl;
Y is selected from hydrogen or hydroxyl;
$R^1$, $R^2$, $R^3$ and $R^4$ are independently selected from hydrogen, halogen, alkyl, alkoxy, haloalkyl, haloalkoxy or —CH=NOC$_2$H$_5$;
$R^5$ is hydrogen;
$R^7$, $R^8$, $R^{10}$ and $R^{11}$ are hydrogen;
$R^9$ is selected from —OC$_2$H$_5$, —OC$_3$H$_7$, —OCH(CH$_3$)$_2$, —OCH$_2$CH$_2$OCH$_3$, —OCH$_2$CH$_2$CH$_2$OCH$_3$, cyclopropylmethoxy, 2-chlorophenoxy, 3-chlorophenoxy, 4-chlorophenoxy, pyrimidin-2-yl, pyrid-2-yl, 3-chloro-pyrid-2-yl, 3-methyl-pyrid-2-yloxy, 4-methyl-pyrid-2-yloxy, 5-methyl-pyrid-2-yloxy, 6-methyl-pyrid-2-yloxy, 3-chloro-pyrid-2-yloxy, 3-trifluoromethyl-pryid-2-yloxy, 3-cyano-pyrid-2-yloxy, 5-cyano-pyrid-2-yloxy, 6-dimethoxymethyl-pyrid-2-yloxy, pyrid-2-yloxy, CO$_2$CH(CH$_3$)$_2$, —CH=NOCH$_3$, —CH=NOC$_2$H$_5$, —CH=NOCH$_2$CF$_3$, —CH=NOallyl, —CH=NOCH$_2$CH=CH$_2$, —CH=NOCH$_2$CN, —CH=NOCH(CH$_3$)$_2$, —CH=NOCH$_2$C≡CH, —CH=NOCH$_2$CH$_2$F, —CH=NOCH$_2$CH$_2$OCH$_3$, —CH=NOCH$_2$OC$_2$H$_5$, —CH=NOCH$_2$CH$_2$OCH$_2$CH$_2$OCH$_3$, —NHCO$_2$CH$_3$, —NHCO$_2$C$_2$H$_5$, —NHCO$_2$CH(CH$_3$)$_2$, —NHCO$_2$CH$_2$-c-C$_3$H$_5$, —CH(OH)C$_6$H$_5$-p-Cl, —OC(=O)NHCH$_3$, —OC(=O)NHC$_2$H$_5$, —OC(=O)NHCH(CH$_3$)$_2$, —NHC(SCH$_3$)=NCN, pyrimidin-2-yloxy, 6-chloro-pyridazin-3yloxy, 6-methoxy-pyridazin-3yloxy, 6-methyl-pyridazin-3yloxy, 2-methyl-2H-tetrazol-5-yl, 2-ethyl-2H-tetrazol-5-yl, 1,3-dioxan-2-yl or 5,5-dimethyl-1,3-dioxan-2-yl; and R is phenyl substituted with $R^{14}$, $R^{15}$, $R^{16}$, $R^{17}$, and $R^{18}$,

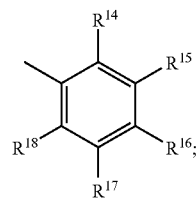

where
$R^{16}$ is selected from haloalkyl or haloalkoxy, and $R^{14}$, $R^{15}$, $R^{17}$ and $R^{18}$ are hydrogen.

Another embodiment of the present invention is a compound of formula I-H or I-J:

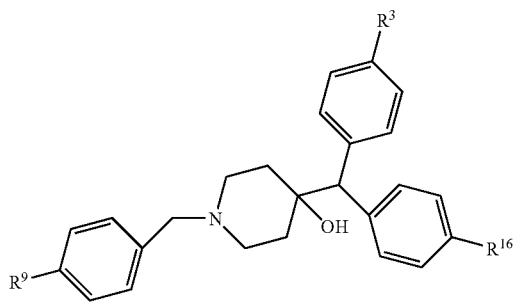

I-H

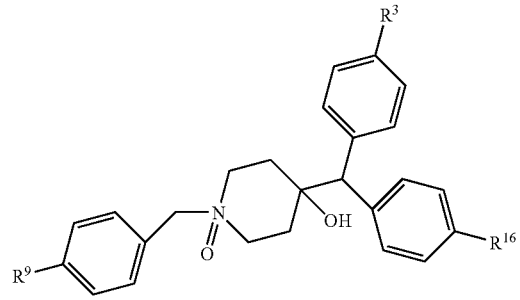

I-J wherein,
$R^3$ is haloalkyl or haloalkoxy;
$R^9$ is selected from —OCH$_2$CH$_2$OCH$_3$, pyrid-2-yloxy, pyrid-2-yl, 3-cyano-pyrid-2-yloxy, 5-methyl-pyrid-2-yloxy, pyrimidin-2-yloxy, pyrimidin-2-yl, 6-chloro-pyridazin-3-yloxy or 6-methoxy-pyridazin-3-yloxy; and $R^{16}$ is haloalkyl or haloalkoxy.

Yet another embodiment of the present invention is the compound:

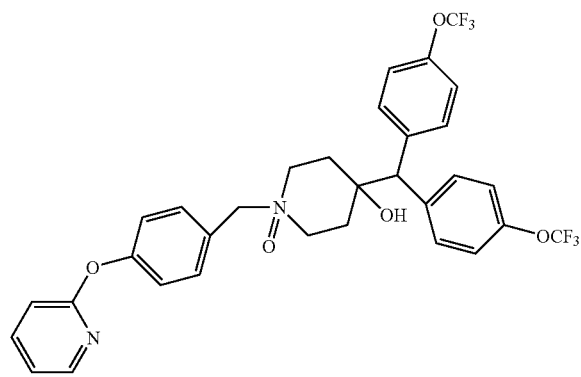

namely, 4-{bis[4-(trifluoromethoxy)phenyl]methyl}-4-hydroxy-1-[(4-(2-pyridyloxy)phenyl)methyl]piperidin-1-oxide, and agriculturally-acceptable salts thereof.

In certain cases the compounds within the scope of formula I may possess asymmetric centers, which can give rise to optical enantiomorphs and diastereomers. Compounds within the scope of formula I may exist in two or more forms, i.e., polymorphs, which are significantly different in physical and chemical properties. Compounds within the scope of formula I may also exist as tautomers, which are in equilibrium. Compounds within the scope of formula I may also possess acidic or basic moieties, which may allow for the formation of agriculturally acceptable salts or agriculturally acceptable metal complexes.

This invention includes the use of such enantiomorphs, polymorphs, tautomers, salts and metal complexes. Agriculturally acceptable salts and metal complexes include, without limitation, for example, ammonium salts, the salts of organic and inorganic acids, such as hydrochloric acid, oleic acid, octanoic acid, 2-ethylhexanoic acid, alkyl sulfonic acid, ethanesulfonic acid, trifluoroacetic acid, methylbenzenesulfonic acid, phosphoric acid, gluconic acid, pamoic acid, and other acid salts, and the alkali metal and alkaline earth metal complexes with, for example, sodium, potassium, lithium, magnesium, calcium, and other metals.

The methods of the present invention are predicated on causing an insecticidally effective amount of a compound of formula I to be present within insects in order to kill or control the insects. Preferred insecticidally effective amounts are those that are sufficient to kill the insect. It is within the scope of the present invention to cause a compound of formula I to be present within insects by contacting the insects with a derivative of that compound, which derivative is converted within the insect to a compound of formula I. This invention includes the use of such compounds, which can be referred to as pro-insecticides.

Another aspect of the present invention relates to compositions containing an insecticidally effective amount of at least one compound of formula I, and, optionally, an effective amount of at least one second compound, with at least one agriculturally acceptable extender or adjuvant.

Another aspect of the present invention relates to methods of controlling insects by applying an insecticidally effective amount of a composition set forth above to a locus of crops such as, without limitation, cereals, cotton, vegetables, and fruits, other areas where insects are present or are expected to be present, or adjacent to areas where insects are present or are expected to be present.

The present invention also includes the use of the compounds and compositions set forth herein for control of insects in greenhouse crops, nursery crops, ornamentals, turfs, forestry, stored food and fiber products, structures, livestock, households, and public and animal health, for example, ants, flies, cockroaches, white grubs, dry wood termites and subterranean termites as well as other insects; and also for use in promotion of animal and human health as pharmaceutical agents and compositions thereof.

As used in this specification and unless otherwise indicated the substituent terms "alkyl", "alkenyl", "alkynyl", "alkoxy", "alkenyloxy", and "alkynyloxy" used alone or as part of a larger moiety, includes straight or branched chains of at least one or two carbon atoms, as appropriate to the substituent, and preferably up to 12 carbon atoms, more preferably up to ten carbon atoms, most preferably up to seven carbon atoms, wherein "alkenyl" has at least one carbon to carbon double bond, and "alkynyl" has at least one carbon to carbon triple bond. The term "aryl" refers to an aromatic ring structure, including fused rings, having four to ten carbon atoms, for example, phenyl and naphthyl. The term "heteroaryl" refers to an aromatic ring structure, including fused rings, having four to ten carbon atoms, and in which one or more of the atoms in the ring is other than carbon, for example, sulfur, oxygen, or nitrogen. The term "THF" refers to tetrahydrofuran. The term "DMSO" refers to methyl sulfoxide. The term "DMF" refers to N,N-dimethylformamide. The term "halogen" or "halo" refers to fluorine, bromine, iodine, or chlorine. The term "ambient temperature" or "room temperature" often abbreviated as "RT", for example, in reference to a chemical reaction mixture temperature, refers to a temperature in the range of 20° C. to 30° C.

Scheme 1 below illustrates a general procedure for synthesizing compounds of formula I, where, for example, m, p, and q are 0; t and u are 1; r is 0 or 1, and if r is 1 an N-oxide is formed; R is phenyl substituted with $R^{14}$, $R^{15}$, $R^{16}$, $R^{17}$ and $R^{18}$; X is OH or F; Y, $R^1$, $R^2$, $R^4$, $R^5$, $R^{14}$, $R^{15}$, $R^{17}$, $R^{18}$, $R^7$, $R^8$, $R^{10}$ and $R^{11}$ are H; $R^3$ and $R^{16}$ are —OCF$_3$; and $R^9$ is pyrimidin-2-yloxy.

Scheme 1

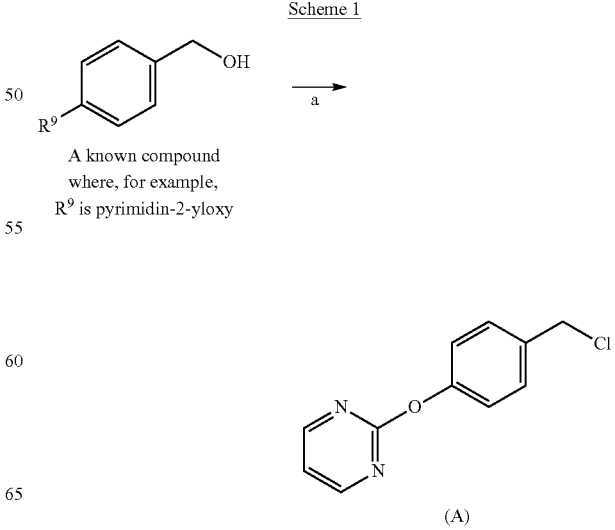

(A)

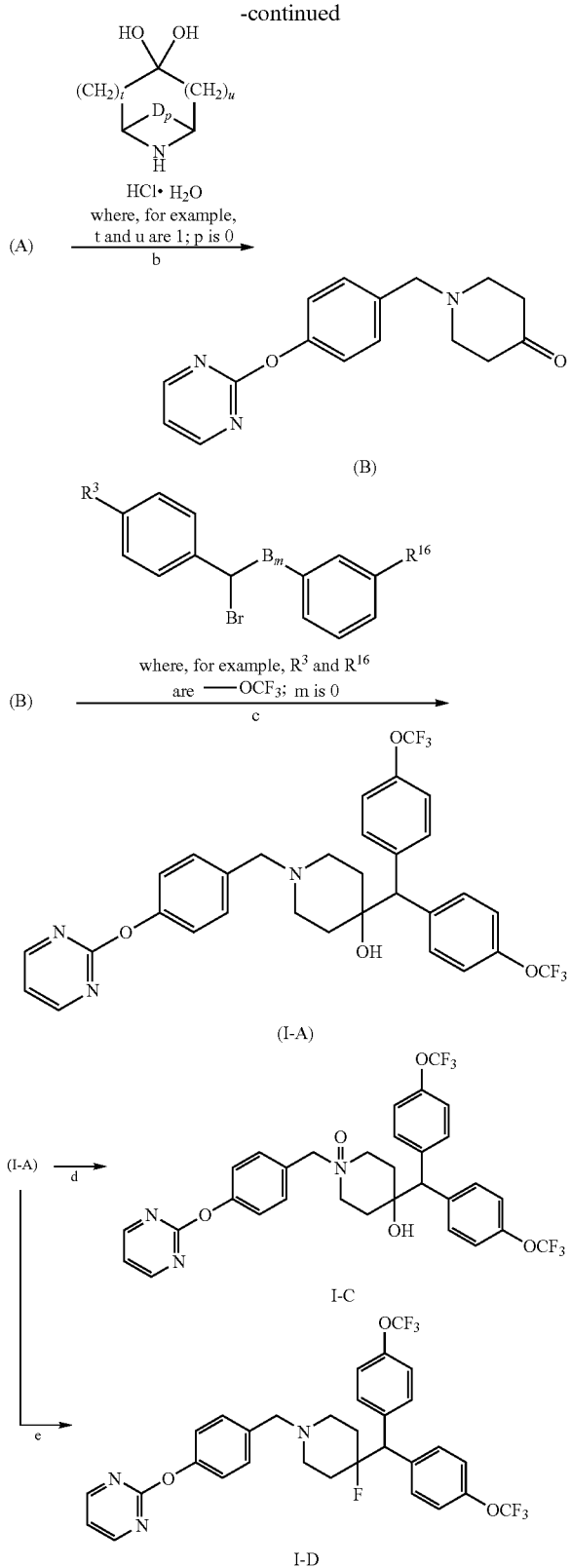

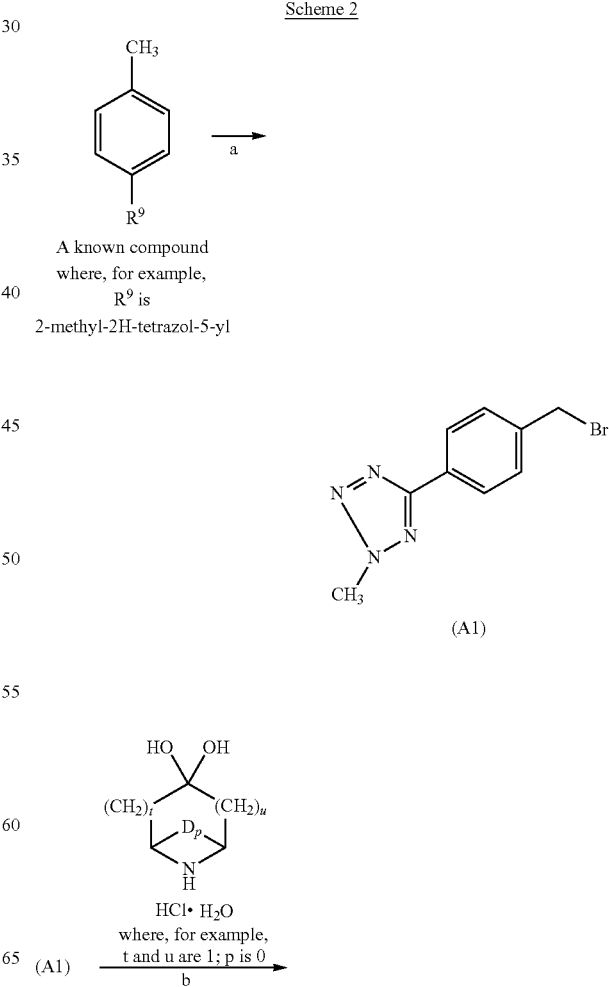

example thionyl chloride, to afford the corresponding 2-[4-(chloromethyl)phenoxy]pyrimidine (A). Intermediate (A) is then reacted under basic conditions with an appropriately substituted cyclic amine derivative, for example, the known compound 4-piperidone hydrochloride monohydrate, to afford the corresponding 1-[(4-pyrimidin-2-yloxyphenyl)methyl]piperidin-4-one (B). A mixture of intermediate (B) and an appropriately substituted haloalkyl derivative, for example bis(trifluoromethoxyphenyl)bromomethane, is reacted in the presence of n-butyl lithium, to afford the corresponding 4-{bis[4-(trifluoromethoxy)phenyl]methyl}-1-[(4-pyrimidin-2-yloxyphenyl)methyl]piperidin-4-ol (I-A). Intermediate (I-A) is then oxidized, with for example hydrogen peroxide, in an appropriate solvent, to form an N-oxide, a compound of formula I-C. In a separate synthesis, intermediate (I-A) is reacted with a thiohalide, for example (dimethylamino)sulfur trifluoride, to provide halogen-derived compounds of formula I-D, wherein X is, for example fluorine. Examples 1 and 3, set forth below, provide detailed methods to how compounds of formula I (-A, -C and -D) shown in Scheme 1 were prepared.

Scheme 2 below illustrates a general procedure for synthesizing compounds of formula I similar to those set forth in Scheme 1, differing in that Y is OH; X is OH; r is 0; and $R^9$ is 2-methyl-2H-tetrazol-5-yl.

Scheme 2

In a first step as depicted in Scheme 1, an appropriately substituted alcohol, for example, the known compound (4-pyrimidin-2-yloxyphenyl)methan-1-ol, is halogenated with, for

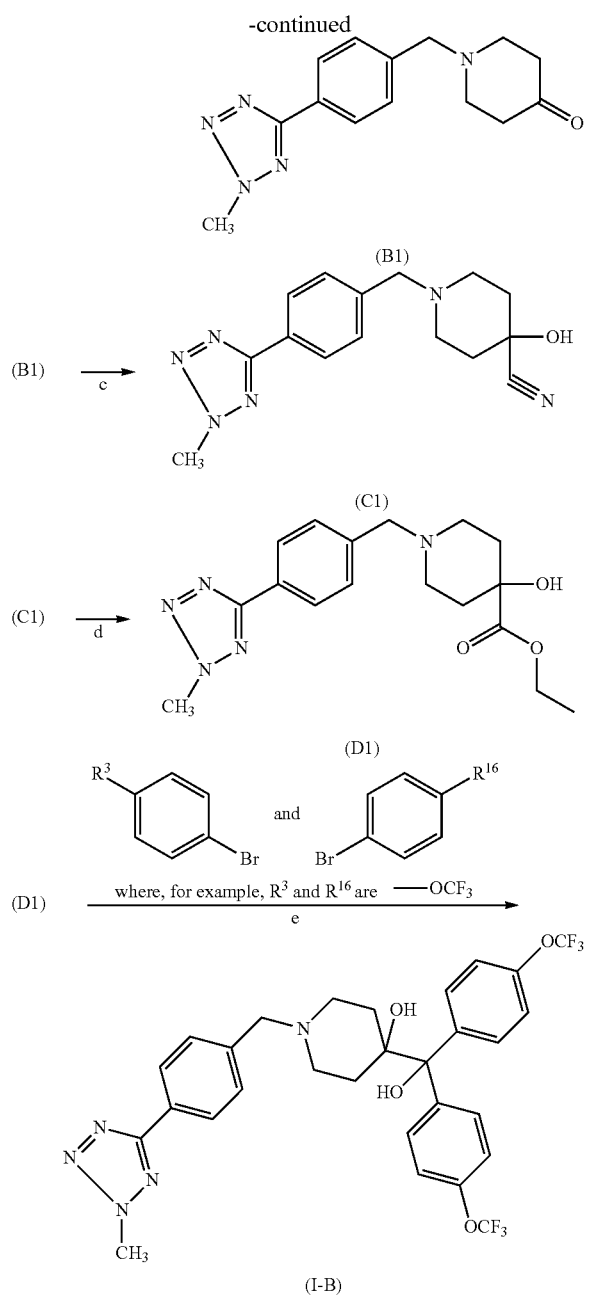

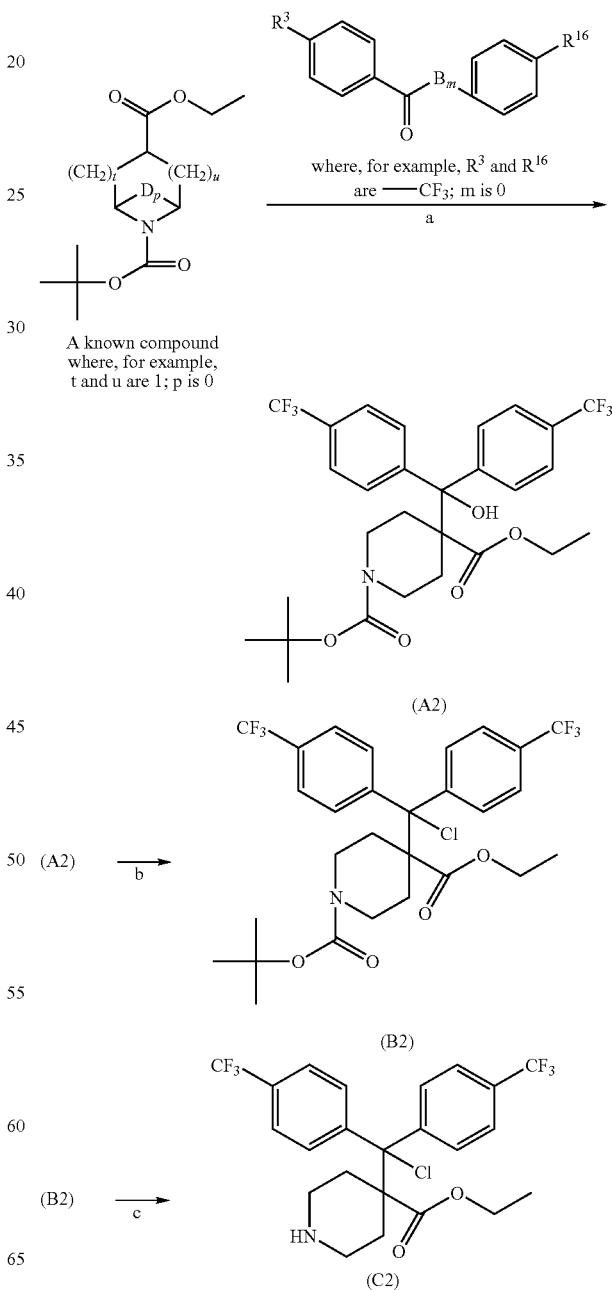

(C1) is esterified under acidic conditions with, for example ethanol, to afford the corresponding ethyl 4-hydroxy-1-{[4-(2-methyl-(1,2,3,4-tetrazol-5-yl))phenyl]methyl}piperidine-4-carboxylate (D1). The Grignard of an appropriately substituted halophenyl derivative, for example 4-trifluoromethoxybromobenzene, is reacted with intermediate (D1) to provide compounds of formula I-B, wherein X and Y are, for example hydroxyl. Example 2, set forth below, provides detailed methods to how compounds of formula I (-B) shown in Scheme 2 were prepared.

Scheme 3 below illustrates a general procedure for synthesizing compounds of formula I similar to those set forth in Scheme 1, differing in that Y is Cl; X is —$CO_2C_2H_5$; r is 0; $R^3$ and $R^{16}$ are —$CF_3$; and $R^9$ is pyrid-2-yloxy.

In a first step as depicted in Scheme 2, an appropriately substituted phenyl derivative, for example, the known compound 2-methyl-5-(4-methylphenyl)-1,2,3,4-tetrazole, is brominated with, for example N-bromosuccinimide and light, to afford the corresponding 5-[4-(bromomethyl)phenyl]-2-methyl-1,2,3,4-tetrazole (A1). Intermediate (A1) is then reacted under basic conditions with an appropriately substituted cyclic amine derivative, for example, the known compound 4-piperidone hydrochloride monohydrate, to afford the corresponding 1-{[4-(2-methyl-1,2,3,4-tetrazol-5-yl)phenyl]methyl}piperidin-4-one (B1). Intermediate (B1) is then reacted under acidic conditions with, for example sodium cyanide, to afford the corresponding nitrile compound, 4-hydroxy-1-{[4-(2-methyl(1,2,3,4-tetrazol-5-yl))phenyl]methyl}piperidine-4-carbonitrile (C1). Intermediate

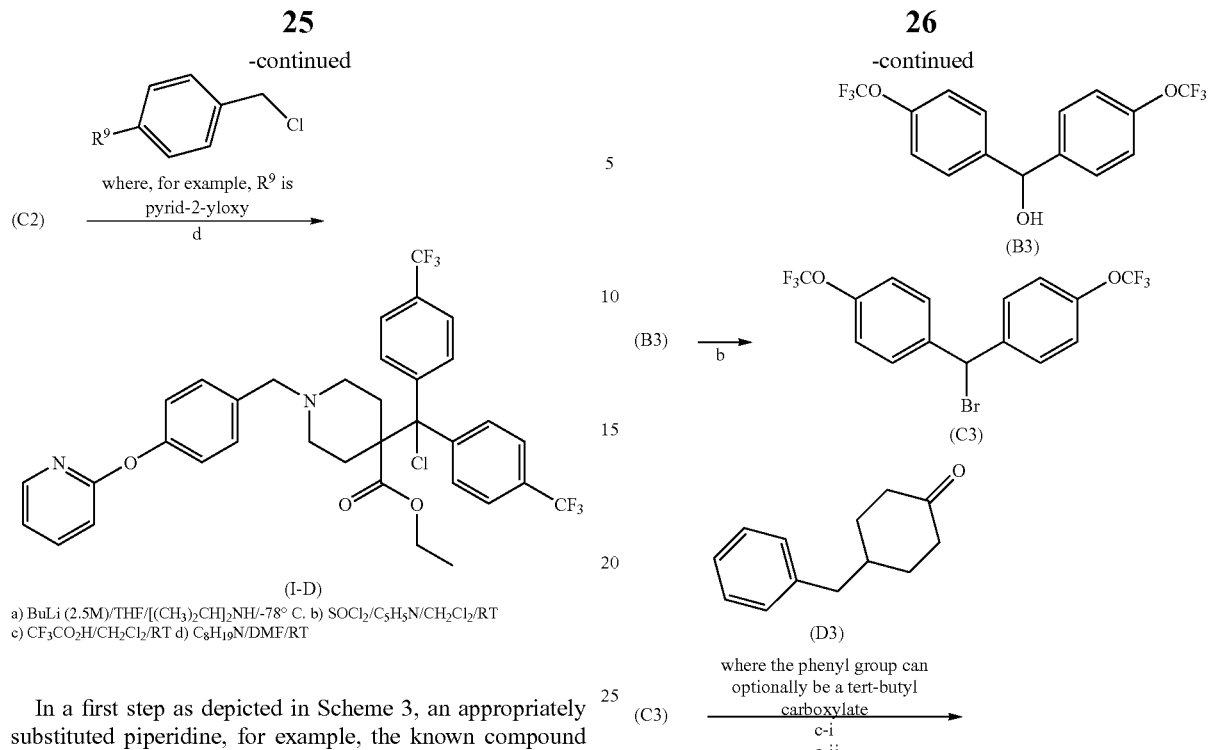

In a first step as depicted in Scheme 3, an appropriately substituted piperidine, for example, the known compound ethyl 1-[(tert-butyl)oxycarbonyl]piperidine-4-carboxylate, is enolated, with for example lithium diisopropylamide, and then reacted under basic conditions with an appropriately substituted phenyl ketone, for example di-4-(trifluoromethyl) phenyl ketone, to afford the corresponding ethyl 1-[(tert-butyl)oxycarbonyl]-4-{bis[4-(trifluoromethyl)phenyl]hydroxymethyl}piperidine-4-carboxylate (A2). Intermediate (A2) is then chlorinated with, for example thionyl chloride, to afford the corresponding ethyl 1-[(tert-butyl)oxycarbonyl]-4-{bis[4-(trifluoromethyl)phenyl]chloromethyl}piperidine-4-carboxylate (B2). The (tert-butyl)oxycarbonyl group is cleaved under acidic conditions from the piperidine ring of (B2), to afford the corresponding 4-{bis[4-(trifluoromethyl)phenyl]chloromethyl}piperidine-4-carboxylate (C2). Intermediate (C2) is then reacted under basic conditions with an appropriately substituted haloalkylphenyl derivative, for example 2-[4-(chloromethyl)phenoxy]pyridine, to provide compounds of formula I-D, wherein X is, for example an alkoxycarbonyl and Y is, for example chlorine. Example 4, set forth below, provides detailed methods to how compounds of formula I (-D) shown in Scheme 3 were prepared.

Scheme 4 below illustrates a general procedure for synthesizing compounds of formula I, where, for example, m, p, and q are 0; t and u are 1; r is 0 or 1, and if r is 1 an N-oxide is formed; R is phenyl substituted with $R^{14}$, $R^{15}$, $R^{16}$, $R^{17}$ and $R^{18}$; X is OH; Y, $R^1$, $R^2$, $R^4$, $R^5$, $R^{14}$, $R^{15}$, $R^{17}$, $R^{18}$, $R^7$, $R^8$, $R^{10}$ and $R^{11}$ are H; $R^3$ and $R^{16}$ are —$OCF_3$; and $R^9$ is pyrid-2-yloxy.

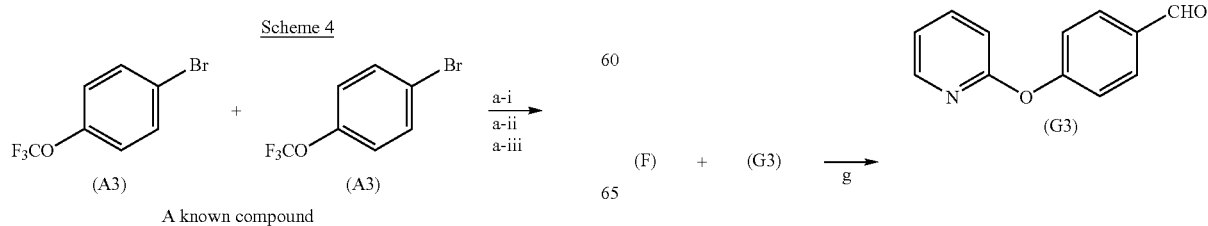

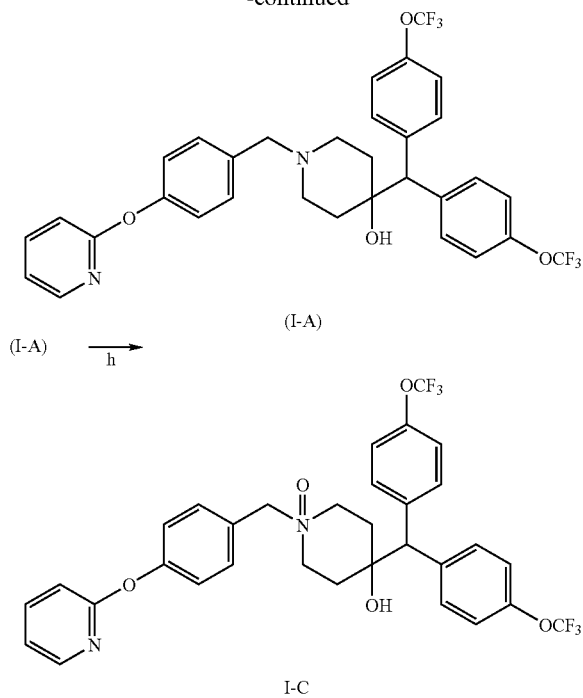

(I-A)

(I-A) → h

I-C a-i) THF/I—PrMgCl/15° C. to RT/24 hours a-ii) HCO₂Et/-10° C. to 0° C. a-iii) 10% NH₄Cl b) Heptane/HBr/Acetic Acid/RT/3 hours c-i) t-BuLi/THF/-85° C. to -60° C./12 hours c-ii) HCl(g) d) MeOH/HCOOH/'Pd(OH)₂/C'/40° C. to 55° C./4 hours e) K₂CO₃/Cu₂O/ 145° C. to 170° C./3.5 hours g) THF/NaBH(OAc)₃/RT/12 hours h) 50% H₂O₂/MeOH/40° C. to 55° C./9-44 hours In the first step as depicted in Scheme 4, two appropriately substituted aryl halides, for example, the known compound 4-bromo-1-(trifluoromethoxy)benzene (A3), were cross-coupled with a Grignard reagent and an alkyl formate, for example, ethyl formate to form bis[4-(trifluoromethoxy)phenyl]methan-1-ol (B3). Intermediate (B3) was then reacted under acidic conditions with hydrogen bromide, to afford the corresponding bis(trifluoromethoxyphenyl)bromomethane (C3). Intermediate (C3) was then lithiated, for example with butyl lithium, and then reacted with an appropriately N-substituted piperidin-4-one, formula (D3), for example 1-benzylpiperidin-4-one, at a temperature in the range of −85° C. to −60° C. to afford the corresponding 4-{bis[4-(trifluoromethoxy)phenyl]methyl}-1-benzylpiperidin-4-ol (E3). Intermediate (E3) was then reacted with an acid, for example formic acid, in the presence of a catalyst, for example a palladium catalyst, to form the hydrogen chloride salt of 4-{bis[4-(trifluoromethoxy)phenyl]methyl}piperidin-4-ol (F3). Next, an appropriately substituted phenol, for example, the known compound 4-hydroxybenzaldehyde, was cross-coupled with a halopyridine, for example 2-chloropyridine, in the presence of potassium carbonate and a catalytic amount of copper oxide at a temperature in the range of 145° C. to 170° C. to form 4-(2-pyridyloxy)benzaldehyde (G3). Intermediate (F3) was then cross-coupled with Intermediate (G3) in the presence of sodium triacetoxyborohydride to form 4-{bis[4-(trifluoromethoxy)phenyl]methyl}-1-[(4-(2-pyridyloxy)phenyl)methyl]piperidin-4-ol (I-A). Intermediate (I-A) was then oxidized with hydrogen peroxide at a temperature in the range of 40° C. to 55° C. to form a compound of formula I-C.

Scheme 5 below illustrates a general procedure for synthesizing compounds of formula I, where, for example, m, p, and q are 0; t and u are 1; r is 0 or 1, and if r is 1 an N-oxide is formed; R is phenyl substituted with $R^{14}$, $R^{15}$, $R^{16}$, $R^{17}$ and $R^{18}$; X is OH; Y, $R^1$, $R^2$, $R^4$, $R^5$, $R^{14}$, $R^{15}$, $R^{17}$, $R^{18}$, $R^7$, $R^8$, $R^{10}$ and $R^{11}$ are H; $R^3$ and $R^{16}$ are —OCF₃; and $R^9$ is pyrid-2-yloxy.

Scheme 5

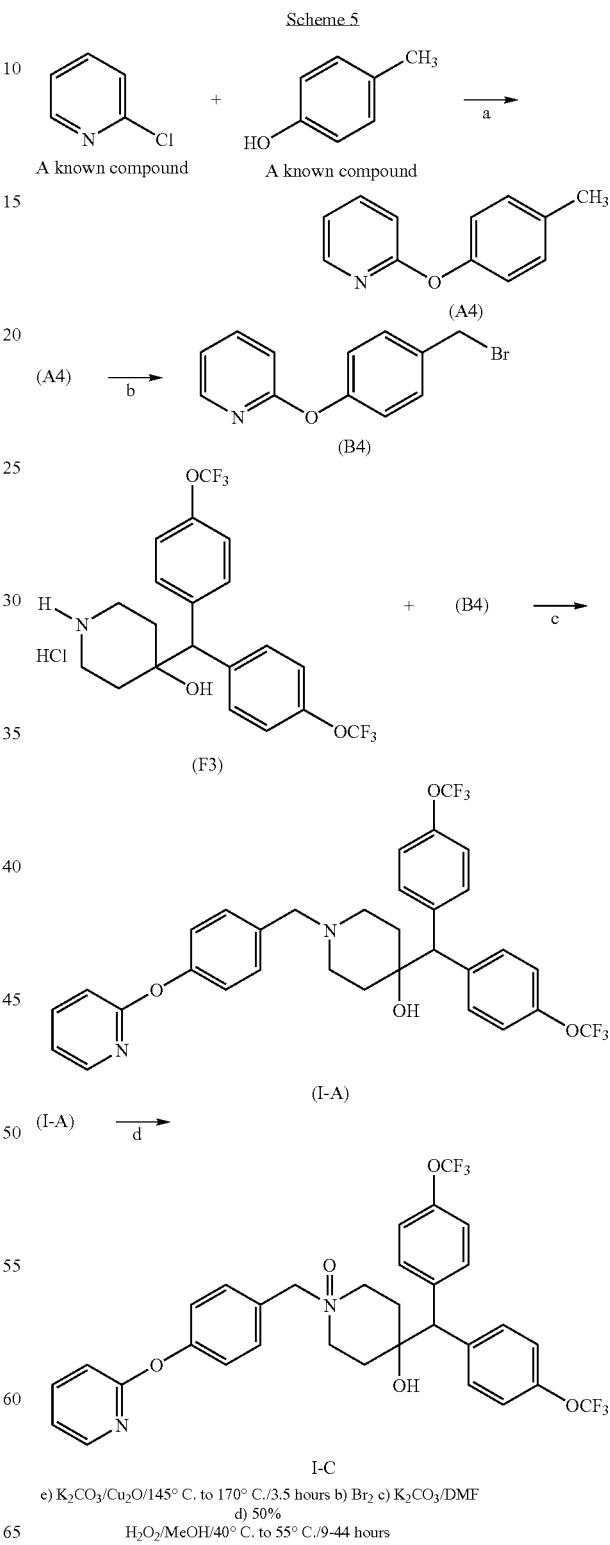

I-C e) K₂CO₃/Cu₂O/145° C. to 170° C./3.5 hours b) Br₂ c) K₂CO₃/DMF d) 50% H₂O₂/MeOH/40° C. to 55° C./9-44 hours In the first step of Scheme 5, an appropriately substituted phenol, for example, the known compound 4-methyl phenol, can be cross-coupled with a halopyridine, for example 2-chloropyridine, in the presence of potassium carbonate and a catalytic amount of copper oxide at a temperature in the range of 145° C. to 170° C. to form 2-(4-methylphenoxy) pyridine (A4). Intermediate (A4) can then be halogenated with, for example bromine, to form 2-[4-(bromomethyl)phenoxy]pyridine (B4). Intermediate (F3), made as in Scheme 4, can then be cross-coupled with Intermediate (B4) in the presence of potassium carbonate to form 4-{bis[4-(trifluoromethoxy)phenyl]methyl}-1-[(4-(2-pyridyloxy)phenyl) methyl]piperidin-4-ol (I-A). Intermediate (I-A) can then be oxidized as in Scheme 4 to form a compound of formula I-C.

One skilled in the art will, of course, recognize that the formulation and mode of application of a toxicant may affect the activity of the material in a given application. Thus, for agricultural use the present insecticidal compounds may be formulated as a granular product of relatively large particle size (for example, 8/16 or 4/8 US Mesh), as water-soluble or water-dispersible granules, as powdery dusts, as wettable powders, as emulsifiable concentrates, as aqueous emulsions, as solutions, or as any of other known types of agriculturally-useful formulations, depending on the desired mode of application. It is to be understood that the amounts specified in this specification are intended to be approximate only, as if the word "about" were placed in front of the amounts specified.

These insecticidal compositions may be applied either as water-diluted sprays, or dusts, or granules to the areas in which suppression of insects is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders, also useful formulations for insecticides, are in the form of finely divided particles that disperse readily in water or other dispersant. The wettable powder is ultimately applied to the locus where insect control is needed either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.0 parts of the insecticidal compound, 17.9 parts of Palmetto clay, and 1.0 part of sodium lignosulfonate and 0.3 part of sulfonated aliphatic polyester as wetting agents. Additional wetting agent and/or oil will frequently be added to a tank mix for to facilitate dispersion on the foliage of the plant.

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isphorone, or other non-volatile organic solvents. For insecticidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs, except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low-boiling dispersant solvent carrier may also be used. Water-soluble or water-dispersible granules are free flowing, non-dusty, and readily water-soluble or water-miscible. In use by the farmer on the field, the granular formulations, emulsifiable concentrates, flowable concentrates, aqueous emulsions, solutions, etc., may be diluted with water to give a concentration of active ingredient in the range of say 0.1% or 0.2% to 1.5% or 2%.

The active insecticidal compounds of this invention may be formulated and/or applied with one or more second compounds. Such combinations may provide certain advantages, such as, without limitation, exhibiting synergistic effects for greater control of insect pests, reducing rates of application of insecticide thereby minimizing any impact to the environment and to worker safety, controlling a broader spectrum of insect pests, safening of crop plants to phytotoxicity, and improving tolerance by non-pest species, such as mammals and fish.

Second compounds include, without limitation, other pesticides, plant growth regulators, fertilizers, soil conditioners, or other agricultural chemicals. In applying an active compound of this invention, whether formulated alone or with other agricultural chemicals, an effective amount and concentration of the active compound is of course employed; the amount may vary in the range of, e.g. about 0.001 to about 3 kg/ha, preferably about 0.03 to about 1 kg/ha. For field use, where there are losses of insecticide, higher application rates (e.g., four times the rates mentioned above) may be employed.

When the active insecticidal compounds of the present invention are used in combination with one or more of second compounds, e.g., with other pesticides such as herbicides, the herbicides include, without limitation, for example: N-(phosphonomethyl)glycine ("glyphosate"); aryloxyalkanoic acids such as (2,4-dichlorophenoxy)acetic acid ("2,4-D"), (4-chloro-2-methylphenoxy)acetic acid ("MCPA"), (+/−)-2-(4-chloro-2-methylphenoxy)propanoic acid ("MCPP"); ureas such as N,N-dimethyl-N'-[4-(1-methylethyl)phenyl]urea ("isoproturon"); imidazolinones such as 2-[4,5-dihydro-4-methyl-4-(1-methylethyl)-5-oxo-1H-imidazol-2-yl]-3-pyridinecarboxylic acid ("imazapyr"), a reaction product comprising (+/−)-2-[4,5-dihydro-4-methyl-4-(1-methylethyl)-5-oxo-1H-imidazol-2-yl]-4-methylbenzoic acid and (+/−)$_2$-[4,5-dihydro-4-methyl-4-(1-methylethyl)-5-oxo-1H-imidazol-2-yl]-5-methylbenzoic acid ("imazamethabenz"), (+/−)-2-[4,5-dihydro-4-methyl-4-(1-methylethyl)-5-oxo-1H-imidazol-2-yl]-5-ethyl-3-pyridinecarboxylic acid ("imazethapyr"), and (+/−)-2-[4,5-dihydro-4-methyl-4-(1-methylethyl)-5-oxo-1H-imidazol-2-yl]-3-quinolinecarboxylic acid ("imazaquin"); diphenyl ethers such as 5-[2-chloro-4-(trifluoromethyl)phenoxy]-2-nitrobenzoic acid ("acifluorfen"), methyl 5-(2,4-dichlorophenoxy)-2-nitrobenzoate ("bifenox"), and 5-[2-chloro-4-(trifluoromethyl)phenoxy]-N-(methylsulfonyl)-2-nitrobenzamide ("fomasafen"); hydroxybenzonitriles such as 4-hydroxy-3,5-diiodobenzonitrile ("ioxynil") and 3,5-dibromo-4-hydroxybenzonitrile ("bromoxynil"); sulfonylureas such as 2-[[[[(4-chloro-6-methoxy-2-pyrimidinyl)amino]carbonyl]amino]sulfonyl]benzoic acid ("chlorimuron"), 2-chloro-N-[[(4-methoxy-6-methyl-1,3,5-triazin-2-yl)amino]carbonyl]benzenesulfonamide (achlorsulfuron"), 2-[[[[[(4,6-dimethoxy-2-pyrimidinyl)amino]carbonyl]amino]sulfonyl]methyl]benzoic acid ("bensulfuron"), 2-[[[[(4,6-dimethoxy-2-pyrimidinyl)amino]carbonyl]amino]sulfonyl]-1-methyl-1H-pyrazol-4-carboxylic acid ("pyrazosulfuron"), 3-[[[[(4-methoxy-6-methyl-1,3,5-triazin-2-yl)amino]carbonyl]amino]sulfonyl]-2-thiophenecarboxylic acid ("thifensulfuron"), and 2-(2-chloroethoxy)-N[[(4-methoxy-6-methyl-1,3,5-triazin-2-yl)amino]carbonyl]benzenesulfonamide ("triasulfuron"); 2-(4-aryloxyphenoxy)alkanoic acids such as (+/−)-2[4-[(6-chloro-2-benzoxazolyl)oxy]phenoxy]-propanoic acid ("fenoxaprop"), (+/−)-2-[4[[5-(trifluoromethyl)-2-pyridinyl]oxy]-phenoxy]propanoic acid ("fluazifop"), (+/−)-2-[4-(6-chloro-2-quinoxalinyl)oxy]-phenoxy]propanoic acid ("quizalofop"), and (+/−)-2-[(2,4-dichlorophenoxy)phenoxy]propanoic acid ("diclofop"); benzothiadiazinones such as 3-(1-methylethyl)-1H-1,2,3-benzothiadiazin-4(3H)-one-2,2-dioxide ("bentazone"); 2-chloroacetanilides such as N-(butoxymethyl)-2-chloro-N-(2,6-diethylphenyl)acetamide ("butachlor"), 2-chloro-N-(2-ethyl-6-methylphenyl)-N-(2-methoxy-1-methylethyl)acetamide ("metolachlor"), 2-chloro-N-(ethoxymethyl)-N-(2-ethyl-6-methylphenyl)acetamide ("acetochlor"), and (RS)-2-chloro-N-(2,4-dimethyl-3-thienyl)-N-(2-methoxy-1-methylethyl)acetamide ("dimethenamide"); arenecarboxylic acids such as 3,6-dichloro-2-methoxybenzoic acid ("dicamba"); pyridyloxyacetic acids such as [(4-amino-3,5-dichloro-6-fluoro-2-pyridinyl)oxy]acetic acid ("fluoroxypyr"), and other herbicides.

When the active insecticidal compounds of the present invention are used in combination with one or more of second compounds, e.g., with other pesticides such as other insecticides, the other insecticides include, for example: organophosphate insecticides, such as chlorpyrifos, diazinon, dimethoate, malathion, parathion-methyl, and terbufos; pyrethroid insecticides, such as fenvalerate, deltamethrin, fenpropathrin, cyfluthrin, flucythrinate, alpha-cypermethrin, biphenthrin, resolved cyhalothrin, etofenprox, esfenvalerate, tralomehtrin, tefluthrin, cycloprothrin, betacyfluthrin, and acrinathrin; carbamate insecticides, such as aldecarb, carbaryl, carbofuran, and methomyl; organochlorine insecticides, such as endosulfan, endrin, heptachlor, and lindane; benzoylurea insecticides, such as diflubenuron, triflumuron, teflubenzuron, chlorfluazuron, flucycloxuron, hexaflumuron, flufenoxuron, and lufenuron; and other insecticides, such as amitraz, clofentezine, fenpyroximate, hexythiazox, spinosad, and imidacloprid.

When the active insecticidal compounds of the present invention are used in combination with one or more of second compounds, e.g., with other pesticides such as fungicides, the fungicides include, for example: benzimidazole fungicides, such as benomyl, carbendazim, thiabendazole, and thiophanate-methyl; 1,2,4-triazole fungicides, such as epoxyconazole, cyproconazole, flusilazole, flutriafol, propiconazole, tebuconazole, triadimefon, and triadimenol; substituted anilide fungicides, such as metalaxyl, oxadixyl, procymidone, and vinclozolin; organophosphorus fungicides, such as fosetyl, iprobenfos, pyrazophos, edifenphos, and tolclofos-methyl; morpholine fungicides, such as fenpropimorph, tridemorph, and dodemorph; other systemic fungicides, such as fenarimol, imazalil, prochloraz, tricyclazole, and triforine; dithiocarbamate fungicides, such as mancozeb, maneb, propineb, zineb, and ziram; non-systemic fungicides, such as chlorothalonil, dichlofluanid, dithianon, and iprodione, captan, dinocap, dodine, fluazinam, gluazatine, PCNB, pencycuron, quintozene, tricylamide, and validamycin; inorganic fungicides, such as copper and sulphur products, and other fungicides.

When the active insecticidal compounds of the present invention are used in combination with one or more of second compounds, e.g., with other pesticides such as nematicides, the nematicides include, for example: carbofuran, carbosulfan, turbufos, aldecarb, ethoprop, fenamphos, oxamyl, isazofos, cadusafos, and other nematicides.

When the active insecticidal compounds of the present invention are used in combination with one or more of second compounds, e.g., with other materials such as plant growth regulators, the plant growth regulators include, for example: maleic hydrazide, chlormequat, ethephon, gibberellin, mepiquat, thidiazon, inabenfide, triaphenthenol, paclobutrazol, unaconazol, DCPA, prohexadione, trinexapac-ethyl, and other plant growth regulators.

Soil conditioners are materials which, when added to the soil, promote a variety of benefits for the efficacious growth of plants. Soil conditioners are used to reduce soil compaction, promote and increase effectiveness of drainage, improve soil permeability, promote optimum plant nutrient content in the soil, and promote better pesticide and fertilizer incorporation. When the active insecticidal compounds of the present invention are used in combination with one or more of second compounds, e.g., with other materials such as soil conditioners, the soil conditioners include organic matter, such as humus, which promotes retention of cation plant nutrients in the soil; mixtures of cation nutrients, such as calcium, magnesium, potash, sodium, and hydrogen complexes; or microorganism compositions which promote conditions in the soil favorable to plant growth. Such microorganism compositions include, for example, *bacillus, pseudomonas, azotobacter, azospirillum, rhizobium*, and soil-borne cyanobacteria.

Fertilizers are plant food supplements, which commonly contain nitrogen, phosphorus, and potassium. When the active insecticidal compounds of the present invention are used in combination with one or more of second compounds, e.g., with other materials such as fertilizers, the fertilizers include nitrogen fertilizers, such as ammonium sulfate, ammonium nitrate, and bone meal; phosphate fertilizers, such as superphosphate, triple superphosphate, ammonium sulfate, and diammonium sulfate; and potassium fertilizers, such as muriate of potash, potassium sulfate, and potassium nitrate, and other fertilizers.

The following examples further illustrate the present invention, but, of course, should not be construed as in any way limiting its scope. The examples are organized to present protocols for the synthesis of the compounds of formula I of the present invention, set forth a list of such synthesized species, and set forth certain biological data indicating the efficacy of such compounds.

EXAMPLE 1

This example illustrates the preparation of 4-{bis[4-(trifluoromethoxy)phenyl]methyl}-4-hydroxy-1-[(4-pyrimidin-2-yloxyphenyl)methyl]piperidin-1-oxide (Compound 112 in table below)

Step A Synthesis of 2-[4-(chloromethyl)phenoxy]pyrimidine as an Intermediate A stirred solution of 2.0 grams (0.0099 mole) of (4-pyrimidin-2-yloxyphenyl)methan-1-ol (known compound) and 7 drops of pyridine in 50 mL of methylene chloride was cooled in an ice-water bath, and 0.94 mL (0.013 mole) of thionyl chloride was added dropwise. Upon completion of the addition, the reaction mixture was stirred for 3 hours at 10° C. to 20° C. The reaction mixture was then poured into ice-water and basified using sodium bicarbonate. The aqueous layer was separated from the organic layer, and was extracted one time with 75 mL of methylene chloride. The methylene chloride extract and organic layer were combined and passed through silicone coated filter paper. The fitrate was then concentrated under reduced pressure, yielding 2.1 grams of the subject compound.

Step B Synthesis of 1-[(4-pyrimidin-2-yloxyphenyl)methyl]piperidin-4-one as an Intermediate A solution of 1.47 grams (0.0096 mole) of 4-piperidone monohydrate hydrochloride, 2.1 grams (0.0096 mole) of 2-[4-(chloromethyl)phenoxy]pyrimidine, and 4.34 grams (0.0336 mole) of bis(methylethyl)ethylamine in 35 mL of dimethylsulfoxide (DMSO) was stirred at ambient temperature for about 24 hours. The reaction mixture was then diluted with 200 mL of water and was extracted two times with 200 mL of ethyl acetate. The extracts were then combined and washed two times with 75 mL of an aqueous mixture of 10% lithium chloride. The resultant organic layer was dried over magnesium sulfate, filtered and concentrated under reduced pressure to a residue. The residue was purified with column chromatography on silica get using 1:2 ethyl acetate:petroleum ether as an eluant. The appropriate fractions were combined and concentrated under reduced pressure, yielding 2.71 grams of the subject compound.

Step C Synthesis of 4-{bis[4-(trifluoromethoxy)phenyl]methyl}-1-[(4-pyrimidin-2-yloxyphenyl)methyl]piperidin-4-ol as an Intermediate A stirred solution of 0.8 gram (0.0019 mole) of bis(trifluoromethoxyphenyl)bromomethane and 2.2 grams (0.0078 mole) of 1-[(4-pyrimidin-2-yloxyphenyl)methyl]piperidin-4-one in 50 mL of THF was chilled to −78° C., and 1.5 mL of n-butyl lithium (2.5 M) was added dropwise during a 15-minute period while maintaining the temperature of the reaction mixture between −80° C. to −70° C. The reaction mixture was then allowed to warm to about 0° C. The reaction mixture was quenched with a saturated aqueous solution of ammonium chloride, and the mixture was extracted two times with 75 mL of ethyl acetate. The combined extracts were dried over sodium sulfate, filtered and concentrated under reduced pressure to a residue. The residue was purified with column chromatography on silica gel using 1:4 acetone:methylene chloride as an eluant. The appropriate fractions were combined and further purified by passing them through a Waters SEP-PAK® Vac 35 cc NH2 Cartridge (purchased from Waters, 34 Maple Street, Milford, Mass. 01757) using 1:4 ethyl acetate:petroleum ether as an eluant. The appropriate fractions were combined and concentrated under reduced pressure, yielding 0.42 gram of the subject compound. The NMR spectrum was consistent with the proposed structure.

Step D Synthesis of Compound 112

A solution of 0.28 gram (0.00045 mole) of 4-{bis[4-(trifluoromethoxy)phenyl]methyl}-1-[(4-pyrimidin-2-yloxyphenyl)methyl]piperidin-4-ol and 1.4 grams of 50% aqueous hydrogen peroxide in 40 mL of methanol was stirred at ambient temperature for about 4 days. The reaction mixture was then diluted with 200 mL of water and extracted twice with 200 mL each of ethyl acetate. The combined extracts were then washed twice with 75 mL each of aqueous mixture of 10% lithium chloride. The organic layer was dried over magnesium sulfate, filtered and concentrated under reduced pressure to a residue. The residue was purified with column chromatography on silica get using 1:2 ethyl acetate:petroleum ether as an eluant. The appropriate fractions were combined and concentrated under reduced pressure, yielding 0.29 gram of Compound 112.

EXAMPLE 2

This example illustrates the preparation of 4-{bis[4-(trifluoromethoxy)phenyl]hydroxymethyl}-1-{[4-(2-methyl(1,2,3,4-tetrazol-5-yl))phenyl]methyl}piperidin-4-ol (Compound 93 in the table below)

Step A Synthesis of 5-[4-(bromomethyl)phenyl]-2-methyl-1,2,3,4-tetrazole as an Intermediate A stirred solution of 45 grams (0.258 mole) of 2-methyl-5-(4-methylphenyl)-1,2,3,4-tetrazole (known compound), 46 grams (1 equivalent) of N-bromosuccinimide, and a catalytic amount of benzoyl peroxide in 200 mL of carbon tetrachloride was irradiated with light during a 3.5 hour period. The mixture was then cooled in an ice bath and filtered to collect 35.1 grams of the subject compound. The NMR spectrum was consistent with the proposed structure.

Step B Synthesis of 1-{[4-(2-methyl-1,2,3,4-tetrazol-5-yl)phenyl]methyl}piperidin-4-one as an Intermediate A solution of 23 grams (0.091 mole) of 5-[4-(bromomethyl)phenyl]-2-methyl-1,2,3,4-tetrazole, 14 grams (0.091 mole) of 4-piperidone monohydrate hydrochloride, and 47 mL (3 equivalents) of N,N-diisopropylethylamine in 200 mL of dimethylsulfoxide (DMSO) was stirred for about 3 days. The reaction was quenched by pouring the reaction mixture onto 400 mL of dilute, cold sodium hydroxide. The resultant solution was extracted one time with 300 mL of ethyl acetate. An emulsion formed, which was broken up by warming it to about 35° C. The organic layer was separated and concentrated under reduced pressure to a residue. The residue was purified with column chromatography on silica gel using 40:1 methylene chloride:methanol as an eluant. The appropriate fractions were combined and concentrated under reduced pressure, yielding 9.12 grams of the subject compound. The NMR spectrum was consistent with the proposed structure.

Step C Synthesis of 4-hydroxy-1-{[4-(2-methyl(1,2,3,4-tetrazol-5-yl))phenyl]methyl}piperidine-4-carbonitrile as an Intermediate A stirred solution of 8.62 grams (0.032 mole) of 1-{[4-(2-methyl-1,2,3,4-tetrazol-5-yl)phenyl]methyl}piperidin-4-one in 100 mL of ether and 150 mL of water was cooled to about 10° C. and 3.9 grams (2.5 equivalents) of sodium cyanide was added in one portion. To this was added 6.6 mL (2.5 equivalents) of hydrochloric acid (12 M) dropwise while maintaining the reaction mixture temperature at about 10° C. Upon completion of the addition, the reaction mixture was stirred for 1.5 hours while warming to ambient temperature. The reaction mixture was then poured into 200 mL of water, to which was then added 200 mL of ethyl acetate. The organic layer was separated and concentrated under reduced pressure to yield 9.6 grams of the subject compound. The NMR spectrum was consistent with the proposed structure.

Step D Synthesis of ethyl 4-hydroxy-1-{[4-(2-methyl(1,2,3,4-tetrazol-5-yl))phenyl]methyl}piperidine-4-carboxylate as an Intermediate A solution of 9.6 grams (0.032 mole) of 4-hydroxy-1-{[4-(2-methyl(1,2,3,4-tetrazol-5-yl))phenyl]methyl}piperidine-4-carbonitrile in 200 mL of ethanol was saturated with gaseous hydrogen chloride, and then it was stirred at 55° C. for about 20 hours. The reaction mixture was allowed to cool and then it was poured onto 500 mL of ice. The resultant mixture was basified with 50% sodium hydroxide and extracted once with 300 mL of ethyl acetate. The extract was washed three times with 80 mL brine, dried over magnesium sulfate, filtered and concentrated under reduced pressure to a residue, yielding 5.14 grams of the subject compound. The NMR spectrum was consistent with the proposed structure.

Step E Synthesis of Compound 93

A solution of 1.6 grams (4.5 equivalents) of magnesium and 8.9 mL (4 equivalents) of 4-trifluoromethoxybromobenzene (known compound) in 75 mL of THF was stirred and 5.14 grams (0.0149 mole) of ethyl 4-hydroxy-1-{[4-(2-methyl(1,2,3,4-tetrazol-5-yl))phenyl]methyl}piperidine-4-carboxylate was added in one portion. After a mild exotherm, the reaction mixture was heated to 50° C. where it was stirred for 2 hours. The reaction mixture was allowed to cool to ambient temperature as it stirred for 72 hours; then it was poured into 200 mL of an aqueous solution saturated with ammonium chloride. The mixture was extracted one time with 200 mL of ethyl acetate, and the extract was washed two times with 80 mL of brine. The extract was dried with magnesium sulfate, filtered and concentrated under reduced pressure to a residue. The residue was purified with column chromatography on silica gel using diethyl ether as an eluant. The appropriate fractions were combined and concentrated under reduced pressure, yielding 9.29 grams of Compound 93.

EXAMPLE 3

This example illustrates the preparation of 4-{bis[4-(trifluoromethoxy)phenyl]methyl}-4-fluoro-1-[(4-pyrimidin-2-yloxyphenyl)methyl]piperidine (Compound 192 in the table below)

A stirred solution of 0.11 gram (0.170 mmole) of 4-{bis[4-(trifluoromethoxy)phenyl]methyl}-1-[(4-pyrimidin-2-yloxyphenyl)methyl]piperidin-4-ol (prepared as in Example 1, Steps A through C) in 2.0 mL of methylene chloride was cooled to −40° C., and 18.2 μL (0.186 mmoles) of (dimethylamino)sulfur trifluoride was added. The reaction mixture was allowed to warm to ambient temperature where it stirred for 20 minutes. The reaction mixture was then poured onto 10 mL of an aqueous solution saturated with sodium bicarbonate, and the mixture was extracted with three 20 mL portions of ethyl acetate. The combined extracts were dried with sodium sulfate, filtered and concentrated under reduced pressure to a residue. The residue was purified with column chromatography on silica gel using 1:1 ethyl acetate:hexane as an eluant. The appropriate fractions were combined and concentrated under reduced pressure, yielding 85 milligrams of Compound 192. The NMR spectrum was consistent with the proposed structure.

EXAMPLE 4

This example illustrates the preparation of ethyl 4-{bis[4-(trifluoromethyl)phenyl]chloromethyl}-1-[(4-(2-pyridyloxy)phenyl)methyl]piperidine-4-carboxylate (Compound 195 in the table below)

Step A Synthesis of ethyl 1-[(tert-butyl)oxycarbonyl]-4-{bis[4-(trifluoromethyl)phenyl]hydroxymethyl}piperidine-4-carboxylate as an Intermediate A stirred solution of 1 mL of diisopropyl amine in 10 mL THF was cooled to about 0° C. and 2.55 mL of n-butyl lithium (2.5 M in hexane) was added slowly. The reaction mixture was stirred for 15 minutes, then it was cooled to −78° C. To this was then added a solution of 1.26 grams (4.9 mmole) of ethyl 1-[(tert-butyl)oxycarbonyl]piperidine-4-carboxylate (known compound) in 10 mL of THF. The reaction mixture continued to stir at −78° C. for 1 hour, then a solution of 1.56 grams (4.9 mmole) of di-4-(trifluoromethyl)phenyl ketone (known compound) in 5 mL of THF was added. Upon completion of the addition, the reaction mixture was warmed to ambient temperature during a 14 hour period. The reaction was then quenched by adding 125 mL of aqueous 5% hydrochloric acid to the reaction mixture. The mixture was then extracted with three 125 mL portions of ethyl acetate and the combined extracts were dried with sodium sulfate, filtered and concentrated under reduced pressure to a residue. The residue was purified with column chromatography on silica gel using 1:5 ethyl acetate:hexane as an eluant. The appropriate fractions were combined and concentrated under reduced pressure, yielding 2.2 grams of the subject compound. The NMR spectrum was consistent with the proposed structure.

Step B Synthesis of ethyl 1-[(tert-butyl)oxycarbonyl]-4-{bis[4-(trifluoromethyl)phenyl]chloromethyl}piperidine-4-carboxylate as an Intermediate A solution of 290 milligrams (0.504 mmole) of ethyl 1-[(tert-butyl)oxycarbonyl]-4-{bis[4-(trifluoromethyl)phenyl]hydroxymethyl}piperidine-4-carboxylate, 110 μL (1.513 mmole) of thionyl chloride, and 408 μL (5.04 mmole) of pyridine in 5 mL of methylene chloride was stirred at ambient temperature for 1 hour. The reaction mixture was then poured into 25 mL of an aqueous solution saturated with sodium bicarbonate, and the mixture was extracted with three 50 mL portions of ethyl acetate. The combined extracts were dried with sodium sulfate, filtered and concentrated under reduced pressure to a residue. The residue was purified with column chromatography on silica gel using 1:10 ethyl acetate:hexane as an eluant. The appropriate fractions were combined and concentrated under reduced pressure, yielding 240 milligrams of the subject compound. The NMR spectrum was consistent with the proposed structure.

Step C Synthesis of ethyl 4-{bis[4-(trifluoromethyl)phenyl]chloromethyl}piperidine-4-carboxylate as an Intermediate A solution of 190 milligrams (0.320 mmole) of ethyl 1-[(tert-butyl)oxycarbonyl]-4-{bis[4-(trifluoromethyl)phenyl]chloromethyl}piperidine-4-carboxylate and 2 mL of trifluoro acetic acid (TFA) in 0.5 mL of methylene chloride was stirred at room temperature for 10 minutes. The reaction mixture was then diluted with toluene and concentrated under reduced pressure, yielding 158 milligrams of the subject compound. The NMR spectrum was consistent with the proposed structure.

Step D Synthesis of Compound 195

A solution of 158 milligrams (0.320 mmole) of ethyl 4-{bis[4-(trifluoromethyl)phenyl]chloromethyl}piperidine-4-carboxylate, 78 milligrams (0.352 mmole) of 2-[4-(chloromethyl)phenoxy]pyridine and 0.28 mL of diisopropylethylamine in 4 mL of DMF was stirred at room temperature for 48 hours. The reaction mixture was then poured into 20 mL of an aqueous solution saturated with sodium bicarbonate, and the mixture was extracted with three 40 mL portions of ethyl acetate. The combined extracts were dried with sodium sulfate, filtered and concentrated under reduced pressure to a residue. The residue was purified with column chromatography on silica gel using 1:5 ethyl acetate:hexane as an eluant. The appropriate fractions were combined and concentrated under reduced pressure, yielding 42 milligrams of Compound 195. The NMR spectrum was consistent with the proposed structure.

EXAMPLE 5

This example illustrates the preparation of 4-{bis[4-(trifluoromethoxy)phenyl]methyl}-4-hydroxy-1-{[4-(2-methoxyethoxy)phenyl]methyl}piperidin-1-oxide (Compound 385 in table below)

Step A Synthesis of 4-(2-methoxyethoxy)benzaldehyde as an Intermediate

A solution of 5.0 grams (0.041 mole) of 4-hydroxybenzaldehyde, 9.5 grams (0.041 mole) of p-toluene sulfonic acid 2-methoxyethyl ester, and 6.3 grams (0.046 mole) of anhydrous potassium carbonate in 50 mL of dimethylsulfoxide (DMSO) was stirred at ambient temperature for about 72 hours. The reaction mixture was then partitioned between 300 mL of an aqueous mixture of 10% lithium chloride and 100 mL of ethyl acetate. The ethyl acetate portion was washed three times; first, with 100 mL of an aqueous mixture of 10% sodium hydroxide, second, with 100 mL of an aqueous mixture of 10% lithium chloride, and, third, with 100 mL of brine. The resultant organic layer was dried over magnesium sulfate, filtered and concentrated under reduced pressure to a residue. The residue was purified with column chromatography on silica gel using methylene chloride as an eluant. The appropriate fractions were combined and concentrated under reduced pressure, yielding 7.3 grams of the subject compound. The NMR spectrum was consistent with the proposed structure.

Step B Synthesis of tert-butyl 4-{bis[4-(trifluoromethoxy)phenyl]methyl}-4-hydroxypiperidine carboxylate as an Intermediate A stirred solution of 8.9 grams (0.022 mole) of bis(trifluoromethoxyphenyl)bromomethane and 4.82 grams (0.024 mole) of tert-butyl 4-oxo-1-piperidine carboxylate in 150 mL of THF was chilled to −78° C., and 9.24 mL of n-butyl lithium (2.5 M) was added dropwise during a 15-minute period while maintaining the temperature of the reaction mixture between −85° C. to −75° C. The reaction mixture was then stirred for 30 minutes while maintaining the temperature of the reaction mixture between −80° C. to −70° C. The reaction mixture was quenched with an aqueous solution saturated with ammonium chloride keeping the internal temperature at less than −55° C., then the mixture was extracted two times with 100 mL of ethyl acetate. The extracts were combined and washed once with 75 mL of an aqueous mixture of 10% lithium chloride. The combined extracts were dried over sodium sulfate, filtered and concentrated under reduced pressure to a residue. The residue was triturated with petroleum ether and a trace of ether then filtered, yielding 3.43 grams of the subject compound. The NMR spectrum was consistent with the proposed structure.

Step C Synthesis of 4-{bis[4-(trifluoromethoxy)phenyl]methyl}piperidin-4-ol as an Intermediate A mixture of 3.0 grams (0.0057 mole) of tert-butyl 4-{bis[4-(trifluoromethoxy)phenyl]methyl}-4-hydroxypiperidine carboxylate and 25 mL of methylene chloride was chilled in a wet ice bath. A solution of 2.63 mL trifluoro acetic acid and 5 mL methylene chloride was added dropwise to the reaction mixture during a 5-minute period. The wet ice bath was removed and the reaction mixture was allowed to warm to ambient temperature. The reaction mixture was then warmed to reflux, and allowed to cool to ambient temperature. The reaction mixture was concentrated under reduced pressure. The residue can then be dissolved in 100 mL methylene chloride and reacted with 200 mL of an aqueous solution saturated with sodium carbonate. The methylene chloride layer can then be separated, dried over magnesium sulfate, filtered and concentrated under reduced pressure to yield the subject compound.

Step D Synthesis of 4-{bis[4-(trifluoromethoxy)phenyl]methyl}-1-{[4-(2-methoxyethoxy)phenyl]methyl}piperidin-4-ol (Compound 308 in table below) as an Intermediate A solution of 2.2 grams (0.0050 mole) of 4-{bis[4-(trifluoromethoxy)phenyl]methyl}piperidin-4-ol, 1.1 grams (0.0061 mole) of 4-(2-methoxyethoxy)benzaldehyde and 1.35 grams (0.0064 mole) of sodium triacetoxyborohydride in 25 mL of methylene chloride was stirred at ambient temperature for 18 hours. The reaction mixture was then diluted with 200 mL of water and stirred at ambient temperature for 5 hours. The phases were separated. The organic phase was washed three times; first, with 100 mL of an aqueous mixture of 10% sodium hydroxide, second, with 100 mL of an aqueous mixture of 10% lithium chloride, and, third, with 100 mL of brine. The resultant organic layer was dried over magnesium sulfate, filtered and concentrated under reduced pressure to a residue. The residue was purified with column chromatography on silica gel using methylene chloride:1%-5% methanol as an eluant. The appropriate fractions were combined and concentrated under reduced pressure, yielding 2.2 grams of the subject compound. The NMR spectrum was consistent with the proposed structure.

Step E Synthesis of Compound 385

A solution of 1.9 grams (0.0032 mole) of 4-{bis[4-(trifluoromethoxy)phenyl]methyl}-{[4-(2-methoxyethoxy)phenyl]methyl}piperidin-4-ol and 2.0 mL of 50% aqueous hydrogen peroxide in 25 mL of methanol was stirred at ambient temperature for about 7 days. The reaction mixture was then partitioned between 300 mL of an aqueous mixture of 10% lithium chloride and 100 mL of ethyl acetate. The aqueous phase was extracted twice with 100 mL each of ethyl acetate. The organic phase and extracts were combined and washed twice; first, with 100 mL of aqueous mixture of 10% lithium chloride, second, with 100 mL of brine. The resultant organic layer was dried over sodium sulfate, filtered and concentrated under reduced pressure to a residue, yielding 1.9 gram of Compound 385. The NMR spectrum was consistent with the proposed structure.

It is well known to one of ordinary skill in the art that compounds like the compounds of formula I of the present invention can contain optically active and racemic forms. It is also well known in the art that compounds like the compounds of formula I may contain stereoisomeric forms, tautomeric forms and/or exhibit polymorphism. It is to be understood that the present invention encompasses any racemic, optically active, polymorphic, tautomeric, or stereoisomeric form, or mixtures thereof. It should be noted that it is well known in the art how to prepare optically active forms, for example by resolution of a racemic mixture, or by synthesis from optically active intermediates.

The following table sets forth some additional examples of compounds of formula I.

TABLE 1

N-Substituted Azacycles

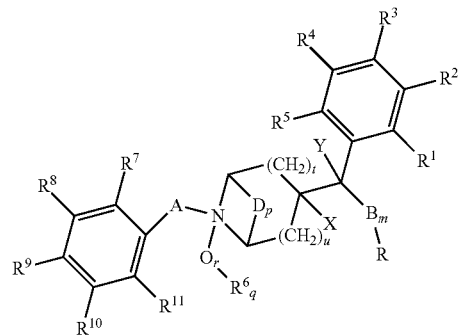

Where
m, p, q and r are 0; t and u are 1; R is phenyl substituted with $R^{14}$, $R^{15}$, $R^{16}$, $R^{17}$, $R^{18}$;
X is OH; A is —$CH_2$—; and $R^5$, $R^7$, $R^8$, $R^{10}$, $R^{11}$ and Y are H:

I-A

TABLE 1-continued

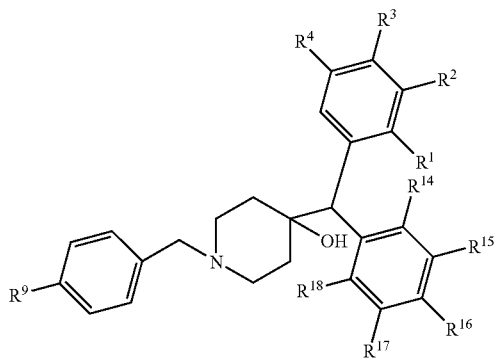

| Compd No. | R¹ | R² | R³ | R⁴ | R⁹ | R¹⁴ | R¹⁵ | R¹⁶ | R¹⁷ | R¹⁸ |
|---|---|---|---|---|---|---|---|---|---|---|
| 1 | Cl | H | H | H | pyrimidin-2-yloxy | H | H | H | H | Cl |
| 2 | H | H | CF$_3$ | H | pyrimidin-2-yloxy | H | H | OCF$_3$ | H | H |
| 3 | H | Cl | H | Cl | pyrimidin-2-yloxy | H | H | CF$_3$ | H | H |
| 4 | H | F | Cl | H | pyrimidin-2-yloxy | H | H | Cl | F | H |
| 5 | H | H | CF$_3$ | H | pyrimidin-2-yloxy | H | OCH$_3$ | H | OCH$_3$ | H |
| 6 | H | Cl | Cl | H | pyrimidin-2-yloxy | H | Cl | Cl | H | H |
| 7 | H | H | CF$_3$ | H | pyrimidin-2-yloxy | H | H | Cl | H | H |
| 8 | H | F | H | H | pyrimidin-2-yloxy | H | H | H | F | H |
| 9 | H | Cl | Cl | H | pyrimidin-2-yloxy | H | H | CF$_3$ | H | H |
| 10 | H | F | H | F | pyrimidin-2-yloxy | H | F | H | F | H |
| 11 | H | F | H | F | pyrimidin-2-yloxy | H | H | CF$_3$ | H | H |
| 12 | H | H | CF$_3$ | H | pyrimidin-2-yloxy | H | H | H | F | H |
| 13 | H | H | CF$_3$ | H | pyrimidin-2-yloxy | Cl | H | H | Cl | H |
| 14 | H | H | CF$_3$ | H | pyrimidin-2-yloxy | H | H | H | Cl | H |
| 15 | Cl | H | Cl | H | pyrimidin-2-yloxy | H | H | CF$_3$ | H | H |
| 16 | H | H | CF$_3$ | H | pyrimidin-2-yloxy | H | H | CF$_3$ | H | H |
| 17 | H | H | CF$_3$ | H | pyrimidin-2-yloxy | H | H | F | F | H |
| 18 | H | H | CF$_3$ | H | pyrimidin-2-yloxy | H | H | H | H | Cl |
| 19 | H | H | OCF$_3$ | H | pyrimidin-2-yloxy | H | H | OCF$_3$ | H | H |
| 20 | H | H | OCF$_3$ | H | pyrimidin-2-yl | H | H | OCF$_3$ | H | H |
| 21 | H | H | OCF$_3$ | H | pyrid-2-yloxy | H | H | OCF$_3$ | H | H |
| 22 | H | H | CF$_3$ | H | pyrid-2-yloxy | H | H | CF$_3$ | H | H |
| 23 | H | H | Cl | H | 2-ethyl-2H-tetrazol-5-yl | H | H | Cl | H | H |
| 24 | H | H | H | Cl | 2-ethyl-2H-tetrazol-5-yl | H | H | H | Cl | H |
| 25 | H | H | OCF$_3$ | H | 2-ethyl-2H-tetrazol-5-yl | H | H | OCF$_3$ | H | H |
| 26 | H | Cl | Cl | H | 2-ethyl-2H-tetrazol-5-yl | H | H | Cl | Cl | H |
| 27 | H | H | CF$_3$ | H | 2-ethyl-2H-tetrazol-5-yl | H | H | CF$_3$ | H | H |
| 28 | H | H | OCF$_3$ | H | CH=NOC$_2$H$_5$ | H | H | OCF$_3$ | H | H |
| 29 | H | H | OCF$_3$ | H | NHC(=O)OCH(CH$_3$)$_2$ | H | H | OCF$_3$ | H | H |
| 30 | H | H | OCF$_3$ | H | 3-(CF$_3$)pyrid-2-yloxy | H | H | OCF | H | H |
| 31 | H | H | CF$_3$ | H | CH=NOCH$_3$ | H | H | CF$_3$ | H | H |
| 32 | H | H | CF$_3$ | H | CH=NOC$_3$H$_7$ | H | H | CF$_3$ | H | H |
| 33 | H | H | CF$_3$ | H | CH=NOCH(CH$_3$)$_2$ | H | H | CF$_3$ | H | H |
| 34 | H | H | CF$_3$ | H | CH=NOCH$_2$CH=CH$_2$ | H | H | CF$_3$ | H | H |
| 35 | H | H | CF$_3$ | H | CH=NOCH$_2$C≡CH | H | H | CF$_3$ | H | H |
| 36 | H | H | CF$_3$ | H | CH=NOC$_2$H$_5$ | H | H | CF$_3$ | H | H |
| 37 | H | H | OCF$_3$ | H | CH=NOCH$_3$ | H | H | OCF$_3$ | H | H |
| 38 | H | H | OCF$_3$ | H | CH=NOC$_3$H$_7$ | H | H | OCF$_3$ | H | H |
| 39 | H | H | OCF$_3$ | H | CH=NOCH(CH$_3$)$_2$ | H | H | OCF$_3$ | H | H |
| 40 | H | H | OCF$_3$ | H | CH=NOCH$_2$CH=CH$_2$ | H | H | OCF$_3$ | H | H |
| 41 | H | H | OCF$_3$ | H | CH=NOCH$_2$C≡CH | H | H | OCF$_3$ | H | H |
| 42 | H | H | OCF$_3$ | H | CH=NOC$_2$H$_5$ | H | H | OCF$_3$ | H | H |
| 43 | H | H | CF$_3$ | H | CH=NOC$_2$H$_5$ | F | H | CF$_3$ | H | H |
| 44 | H | H | CF$_3$ | H | CH=NOC$_2$H$_5$ | Cl | H | CF$_3$ | H | H |
| 45 | H | H | OCF$_3$ | H | phenoxy | H | H | OCF$_3$ | H | H |
| 46 | H | H | OCF$_3$ | H | 4-(1-methylethyoxycarbonyl)phenoxy | H | H | OCF$_3$ | H | H |
| 47 | H | H | OCF$_3$ | H | 4-(methoxycarbonyl)phenoxy | H | H | OCF$_3$ | H | H |
| 48 | H | H | OCF$_3$ | H | 6-chloro-pyridazin-3yloxy | H | H | OCF$_3$ | H | H |
| 49 | H | H | CF$_3$ | H | 6-chloro-pyridazin-3yloxy | H | H | CF$_3$ | H | H |
| 50 | H | H | OCF$_3$ | H | NHCO$_2$CH$_3$ | H | H | OCF$_3$ | H | H |
| 51 | H | H | OCF$_3$ | H | NHCO$_2$C$_2$H$_5$ | H | H | OCF$_3$ | H | H |
| 52 | H | H | OCF$_3$ | H | NHCO$_2$CH$_2$CH=CH$_2$ | H | H | OCF$_3$ | H | H |
| 53 | H | H | OCF$_3$ | H | NHCO$_2$CH$_2$C≡CH | H | H | OCF$_3$ | H | H |
| 54 | H | H | CF$_3$ | H | NHCO$_2$CH(CH$_3$)$_2$ | H | H | CF$_3$ | H | H |
| 55 | H | H | CF$_3$ | H | NHCO$_2$CH$_3$ | H | H | CF$_3$ | H | H |
| 56 | H | H | CF$_3$ | H | NHCO$_2$CH$_2$CH=CH$_2$ | H | H | CF$_3$ | H | H |
| 57 | H | H | CF$_3$ | H | OC(=O)NHCH$_3$ | H | H | CF$_3$ | H | H |
| 58 | H | H | CF$_3$ | H | OC(=O)NHC$_2$H$_5$ | H | H | CF$_3$ | H | H |
| 59 | H | H | CF$_3$ | H | OC(=O)NHCH(CH$_3$)$_2$ | H | H | CF$_3$ | H | H |

TABLE 1-continued

| | | | | | | | | | | |
|---|---|---|---|---|---|---|---|---|---|---|
| 60 | H | H | $CF_3$ | H | $OC(=O)NHCH_2CH=CH_2$ | H | H | $CF_3$ | H | H |
| 61 | H | H | $OCF_3$ | H | $OC(=O)NHCH_3$ | H | H | $OCF_3$ | H | H |
| 62 | H | H | $OCF_3$ | H | $OC(=O)NHC_2H_5$ | H | H | $OCF_3$ | H | H |
| 63 | H | H | $OCF_3$ | H | $OC(=O)NHCH(CH_3)_2$ | H | H | $OCF_3$ | H | H |
| 64 | H | H | $OCF_3$ | H | $OC(=O)NHCH_2CH=CH_2$ | H | H | $OCF_3$ | H | H |
| 65 | H | H | $OCF_3$ | H | $OC(=O)NHCH_2C≡CH$ | H | H | $OCF_3$ | H | H |
| 66 | H | H | $CF_3$ | H | $OCH_3$ | H | H | $CF_3$ | H | H |
| 67 | H | H | $CF_3$ | H | $OC_2H_5$ | H | H | $CF_3$ | H | H |
| 68 | H | H | $CF_3$ | H | $OC_3H_7$ | H | H | $CF_3$ | H | H |
| 69 | H | H | $CF_3$ | H | cyclopentoxy | H | H | $CF_3$ | H | H |
| 70 | H | H | $OCF_3$ | H | $OCH_3$ | H | H | $OCF_3$ | H | H |
| 71 | H | H | $OCF_3$ | H | $OC_2H_5$ | H | H | $OCF_3$ | H | H |
| 72 | H | H | $OCF_3$ | H | $OC_3H_7$ | H | H | $OCF_3$ | H | H |
| 73 | H | H | $OCF_3$ | H | $OCH(CH_3)_2$ | H | H | $OCF_3$ | H | H |
| 74 | H | H | $OCF_3$ | H | cyclopentoxy | H | H | $OCF_3$ | H | H |
| 75 | H | H | $OCHF_2$ | H | pyrid-2-yloxy | H | H | $OCHF_2$ | H | H |
| 76 | H | H | $OCHF_2$ | H | pyrimidin-2-yloxy | H | H | $OCHF_2$ | H | H |
| 77 | H | H | $OCHF_2$ | H | $CH=NOC_2H_5$ | H | H | $OCHF_2$ | H | H |
| 78 | H | H | $OCHF_2$ | H | $OC(=O)NHCH(CH_3)_2$ | H | H | $OCHF_2$ | H | H |
| 79 | H | H | $OCHF_2$ | H | $NHCO_2CH(CH_3)_2$ | H | H | $OCHF_2$ | H | H |
| 80 | H | H | $OCHF_2$ | H | $OC_3H_7$ | H | H | $OCHF_2$ | H | H |
| 81 | H | H | $OCF_2CHF_2$ | H | pyrid-2-yloxy | H | H | $OCF_2CHF_2$ | H | H |
| 82 | H | H | $OCF_2CHF_2$ | H | pyrimidin-2-yloxy | H | H | $OCF_2CHF_2$ | H | H |
| 83 | H | H | $OCF_2CHF_2$ | H | 6-chloro-pyridazin-3yloxy | H | H | $OCF_2CHF_2$ | H | H |
| 84 | H | H | $OCF_2CHF_2$ | H | $OC_3H_7$ | H | H | $OCF_2CHF_2$ | H | H |
| 85 | H | H | $OCF_2CHF_2$ | H | $OC(=O)NHCH(CH_3)_2$ | H | H | $OCF_2CHF_2$ | H | H |
| 86 | H | H | $OCF_2CHF_2$ | H | $NHCO_2CH(CH_3)_2$ | H | H | $OCF_2CHF_2$ | H | H |
| 87 | H | H | $OCF_2CHF_2$ | H | $OCO_2CH(CH_3)_2$ | H | H | $OCF_2CHF_2$ | H | H |
| 88 | H | H | $SF_5$ | H | pyrimidin-2-yloxy | H | H | $SF_5$ | H | H |
| 89 | H | H | $SF_5$ | H | pyrimidin-2-yloxy | H | H | $CF_3$ | H | H |
| 90 | H | H | $OCF_3$ | H | $CO_2CH(CH_3)_2$ | H | H | $OCF_3$ | H | H | where
m, p, q and r are 0; t and u are 1; R is phenyl substituted with $R^{14}$, $R^{15}$, $R^{16}$, $R^{17}$, $R^{18}$;
X and Y are OH; A is —$CH_2$—; and $R^1$, $R^2$, $R^4$, $R^5$, $R^{14}$, $R^{15}$, $R^{17}$, $R^{18}$, $R^7$, $R^8$, $R^{10}$, and $R^{11}$ are H:

I-B

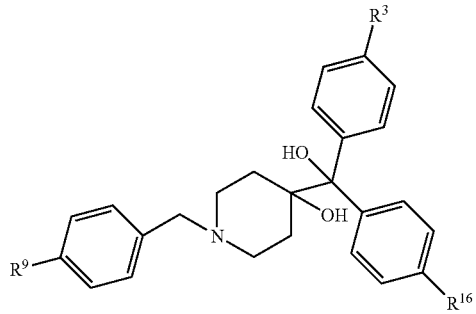

| Compd. No. | $R^3$ | $R^9$ | $R^{16}$ |
|---|---|---|---|
| 91 | $OCF_3$ | $OC_3H_7$ | $OCF_3$ |
| 92 | $CF_3$ | $OC_3H_7$ | $CF_3$ |
| 93 | $OCF_3$ | 2-methyl-2H-tetrazol-5-yl | $OCF_3$ |
| 94 | $CF_3$ | pyrid-2-yloxy | $CF_3$ |
| 95 | $CF_3$ | pyrimidin-2-yloxy | $CF_3$ |
| 96 | $CF_3$ | 6-chloro-pyridazin-3yloxy | $CF_3$ |
| 97 | $CF_3$ | 6-methoxy-pyridazin-3yloxy | $CF_3$ |
| 98 | $CF_3$ | 2-ethyl-2H-tetrazol-5-yl | $CF_3$ |
| 99 | $CF_3$ | $CH=NOCH_3$ | $CF_3$ |
| 100 | $CF_3$ | $CH=NOCH_2CH=CH_2$ | $CF_3$ |
| 101 | $CF_3$ | $CH=NOCH_2C≡CH$ | $CF_3$ |
| 102 | $CF_3$ | 4-(1-methylethoxycarbonyl)phenoxy | $CF_3$ |
| 103 | $OCF_3$ | $CH=NOCH_2C≡CH$ | $OCF_3$ |
| 104 | $OCF_3$ | pyrid-2-yloxy | $OCF_3$ |
| 105 | $OCF_3$ | pyrimidin-2-yloxy | $OCF_3$ |
| 106 | $OCF_3$ | 6-chloro-pyridazin-3yloxy | $OCF_3$ |
| 107 | $OCF_3$ | 6-methoxy-pyridazin-3yloxy | $OCF_3$ |
| 108 | $OCF_3$ | $CH=NOCH_3$ | $OCF_3$ |
| 109 | $OCF_3$ | $CH=NOCH_2CH=CH_2$ | $OCF_3$ |
| 110 | $OCF_3$ | 4-(1-methylethoxycarbonyl)phenoxy | $OCF_3$ | where
m, p, and q are 0; t and u are 1; r is 1, forming an N-oxide; R is phenyl substituted
with $R^{14}$, $R^{15}$, $R^{16}$, $R^{17}$, $R^{18}$;
X is OH; A is —$CH_2$—; and $R^1$, $R^4$, $R^5$, $R^{15}$, $R^{18}$, $R^7$, $R^8$,
$R^{10}$, and $R^{11}$ are H:

TABLE 1-continued

I-C

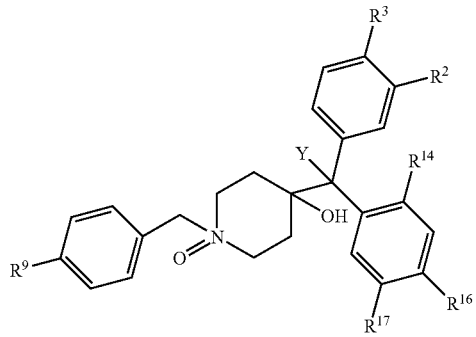

| Compd. No. | R² | R³ | R⁹ | R¹⁴ | R¹⁶ | R¹⁷ | Y |
|---|---|---|---|---|---|---|---|
| 111 | H | CF₃ | pyrid-2-yloxy | H | CF₃ | H | H |
| 112 | H | OCF₃ | pyrimidin-2-yloxy | H | OCF₃ | H | H |
| 113 | H | CF₃ | 2-ethyl-2H-tetrazol-5-yl | H | CF₃ | H | H |
| 114 | H | OCF₃ | 2-ethyl-2H-tetrazol-5-yl | H | OCF₃ | H | H |
| 115 | F | Cl | pyrimidin-2-yloxy | H | Cl | F | H |
| 116 | H | OCF₃ | pyrimidin-2-yl | H | OCF₃ | H | H |
| 117 | H | OCF₃ | pyrid-2-yloxy | H | OCF₃ | H | H |
| 118 | H | OCF₃ | CH=NOC₂H₅ | H | OCF₃ | H | H |
| 119 | H | OCF₃ | NHC(=O)OCH(CH₃)₂ | H | OCF₃ | H | H |
| 120 | H | CF₃ | pyrimidin-2-yloxy | H | CF₃ | H | H |
| 121 | H | CF₃ | OC₃H₇ | H | CF₃ | H | OH |
| 122 | H | OCF₃ | 2-methyl-2H-tetrazol-5-yl | H | OCF₃ | H | OH |
| 123 | H | OCF₃ | OC₃H₇ | H | OCF₃ | H | OH |
| 124 | H | CF₃ | CH=NOCH₃ | H | CF₃ | H | H |
| 125 | H | CF₃ | CH=NOC₃H₇ | H | CF₃ | H | H |
| 126 | H | CF₃ | CH=NOCH(CH₃)₂ | H | CF₃ | H | H |
| 127 | H | CF₃ | CH=NOCH₂CH=CH₂ | H | CF₃ | H | H |
| 128 | H | CF₃ | CH=NOCH₂C≡CH | H | CF₃ | H | H |
| 129 | H | CF₃ | CH=NOC₂H₅ | H | CF₃ | H | H |
| 130 | H | OCF₃ | CH=NOCH₃ | H | OCF₃ | H | H |
| 131 | H | OCF₃ | CH=NOC₃H₇ | H | OCF₃ | H | H |
| 132 | H | OCF₃ | CH=NOCH(CH₃)₂ | H | OCF₃ | H | H |
| 133 | H | OCF₃ | CH=NOCH₂CH=CH₂ | H | OCF₃ | H | H |
| 134 | H | OCF₃ | CH=NOCH₂C≡CH | H | OCF₃ | H | H |
| 135 | H | OCF₃ | CH=NOC₂H₅ | H | OCF₃ | H | H |
| 136 | H | CF₃ | CH=NOC₂H₅ | H | CF₃ | H | H |
| 137 | H | CF₃ | CH=NOC₂H₅ | H | CF₃ | H | H |
| 138 | H | OCF₃ | phenoxy | H | OCF₃ | H | H |
| 139 | H | OCF₃ | 4-(1-methylethyoxycarbonyl)phenoxy | H | OCF₃ | H | H |
| 140 | H | OCF₃ | 4-(methoxycarbonyl)phenoxy | H | OCF₃ | H | H |
| 141 | H | OCF₃ | 6-chloro-pyridazin-3yloxy | H | OCF₃ | H | H |
| 142 | H | CF₃ | 6-chloro-pyridazin-3yloxy | H | CF₃ | H | H |
| 143 | H | OCF₃ | NHCO₂CH₃ | H | OCF₃ | H | H |
| 144 | H | OCF₃ | NHCO₂C₂H₅ | H | OCF₃ | H | H |
| 145 | H | OCF₃ | NHCO₂CH₂CH=CH₂ | H | OCF₃ | H | H |
| 146 | H | OCF₃ | NHCO₂CH₂C≡CH | H | OCF₃ | H | H |
| 147 | H | CF₃ | NHCO₂CH(CH₃)₂ | H | CF₃ | H | H |
| 148 | H | CF₃ | NHCO₂CH₃ | H | CF₃ | H | H |
| 149 | H | CF₃ | NHCO₂CH₂CH=CH₂ | H | CF₃ | H | H |
| 150 | H | CF₃ | OC(=O)NHCH₃ | H | CF₃ | H | H |
| 151 | H | CF₃ | OC(=O)NHC₂H₅ | H | CF₃ | H | H |
| 152 | H | CF₃ | OC(=O)NHCH(CH₃)₂ | H | CF₃ | H | H |
| 153 | H | CF₃ | OC(=O)NHCH₂CH=CH₂ | H | CF₃ | H | H |
| 154 | H | OCF₃ | OC(=O)NHCH₃ | H | OCF₃ | H | H |
| 155 | H | OCF₃ | OC(=O)NHC₂H₅ | H | OCF₃ | H | H |
| 156 | H | OCF₃ | OC(=O)NHCH(CH₃)₂ | H | OCF₃ | H | H |
| 157 | H | OCF₃ | OC(=O)NHCH₂CH=CH₂ | H | OCF₃ | H | H |
| 158 | H | OCF₃ | OC(=O)NHCH₂C≡CH | H | OCF₃ | H | H |
| 159 | H | CF₃ | OCH₃ | H | CF₃ | H | H |
| 160 | H | CF₃ | OC₂H₅ | H | CF₃ | H | H |
| 161 | H | CF₃ | OC₃H₇ | H | CF₃ | H | H |
| 162 | H | CF₃ | cyclopentoxy | H | CF₃ | H | H |
| 163 | H | OCF₃ | OCH₃ | H | OCF₃ | H | H |
| 164 | H | OCF₃ | OC₂H₅ | H | OCF₃ | H | H |
| 165 | H | OCF₃ | OC₃H₇ | H | OCF₃ | H | H |
| 166 | H | OCF₃ | OCH(CH₃)₂ | H | OCF₃ | H | H |
| 167 | H | OCF₃ | cyclopentoxy | H | OCF₃ | H | H |

TABLE 1-continued

| | | | | | | | |
|---|---|---|---|---|---|---|---|
| 168 | H | OCHF$_2$ | pyrid-2-yloxy | H | OCHF$_2$ | H | H |
| 169 | H | OCHF$_2$ | pyrimidin-2-yloxy | H | OCHF$_2$ | H | H |
| 170 | H | OCHF$_2$ | CH=NOC$_2$H$_5$ | H | OCHF$_2$ | H | H |
| 171 | H | OCHF$_2$ | OC(=O)NHCH(CH$_3$)$_2$ | H | OCHF$_2$ | H | H |
| 172 | H | OCHF$_2$ | NHCO$_2$CH(CH$_3$)$_2$ | H | OCHF$_2$ | H | H |
| 173 | H | OCHF$_2$ | OC$_3$H$_7$ | H | OCHF$_2$ | H | H |
| 174 | H | OCF$_2$CHF$_2$ | pyrid-2-yloxy | H | OCF$_2$CHF$_2$ | H | H |
| 175 | H | OCF$_2$CHF$_2$ | pyrimidin-2-yloxy | H | OCF$_2$CHF$_2$ | H | H |
| 176 | H | OCF$_2$CHF$_2$ | 6-chloro-pyridazin-3yloxy | H | OCF$_2$CHF$_2$ | H | H |
| 177 | H | OCF$_2$CHF$_2$ | OC$_3$H$_7$ | H | OCF$_2$CHF$_2$ | H | H |
| 178 | H | OCF$_2$CHF$_2$ | OC(=O)NHCH(CH$_3$)$_2$ | H | OCF$_2$CHF$_2$ | H | H |
| 179 | H | OCF$_2$CHF$_2$ | NHCO$_2$CH(CH$_3$)$_2$ | H | OCF$_2$CHF$_2$ | H | H |
| 180 | H | OCF$_2$CHF$_2$ | OCO$_2$CH(CH$_3$)$_2$ | H | OCF$_2$CHF$_2$ | H | H |
| 181 | H | SF$_5$ | pyrid-2-yloxy | H | SF$_5$ | H | H |
| 182 | H | OCF$_3$ | pyrid-2-yloxy | Cl | OCF$_3$ | H | H |
| 183 | H | CF$_3$ | pyrid-2-yloxy | Cl | CF$_3$ | H | H |
| 184 | H | OCF$_3$ | pyrimidin-2-yloxy | Cl | OCF$_3$ | H | H |
| 185 | H | OCF$_3$ | CH=NOC$_2$H$_5$ | Cl | OCF$_3$ | H | H |
| 186 | H | OCF$_3$ | 6-chloro-pyridizin-3yloxy | Cl | OCF$_3$ | H | H |
| 187 | H | OCF$_3$ | pyrid-2-yloxy | Cl | Cl | H | H |
| 188 | H | OCF$_3$ | pyrid-2-yloxy | F | OCF$_3$ | H | H |
| 189 | H | OCF$_3$ | pyrimidin-2-yloxy | F | OCF$_3$ | H | H |
| 190 | H | OCF$_3$ | CH=NOC$_2$H$_5$ | F | OCF$_3$ | H | H |
| 191 | H | OCF$_3$ | CO$_2$CH(CH$_3$)$_2$ | H | OCF$_3$ | H | H | where
m, p, q and r are 0; t and u are 1; R is phenyl substituted with R$^{14}$, R$^{15}$, R$^{16}$, R$^{17}$, R$^{18}$;
A is —CH$_2$—; and R$^1$, R$^2$, R$^4$, R$^5$, R$^{14}$, R$^{15}$, R$^{17}$, R$^7$, R$^8$, R$^{10}$ and R$^{11}$ are H:

I-D

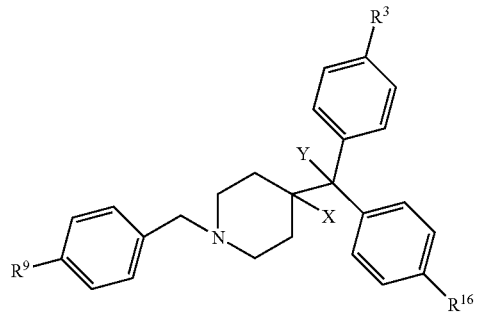

| Compd. No. | X | Y | R$^3$ | R$^9$ | R$^{16}$ |
|---|---|---|---|---|---|
| 192 | F | H | OCF$_3$ | pyrimidin-2-yloxy | OCF$_3$ |
| 193 | F | H | CF$_3$ | pyrid-2-yloxy | CF$_3$ |
| 194 | F | H | CF$_3$ | pyrimidin-2-yloxy | CF$_3$ |
| 195 | C(=O)OC$_2$H$_5$ | Cl | CF$_3$ | pyrid-2-yloxy | CF$_3$ |
| 196 | C(=O)OC$_2$H$_5$ | H | CF$_3$ | pyrid-2-yloxy | CF$_3$ |
| 197 | C(=O)OC$_2$H$_5$ | F | CF$_3$ | pyrid-2-yloxy | CF$_3$ |
| 198 | C≡N | Cl | CF$_3$ | pyrid-2-yloxy | CF$_3$ |
| 199 | OH | CH$_3$ | CF$_3$ | pyrid-2-yloxy | CF$_3$ |
| 200 | OH | CH(CH$_3$)$_2$ | CF$_3$ | pyrid-2-yloxy | CF$_3$ |
| 201 | CH$_2$OH | H | CF$_3$ | pyrid-2-yloxy | CF$_3$ |
| 202 | OH | CH$_3$ | CF$_3$ | pyrimidin-2-yl | CF$_3$ |
| 203 | OH | CH$_3$ | CF$_3$ | CH=NOCH$_3$ | CF$_3$ |
| 204 | OH | CH$_3$ | OCF$_3$ | pyrid-2-yl | OCF$_3$ |
| 205 | OH | CH$_3$ | OCF$_3$ | pyrimidin-2-yl | OCF$_3$ |
| 206 | OH | CH$_3$ | OCF$_3$ | CH=NOCH$_3$ | OCF$_3$ |
| 207 | C(=O)OCH$_3$ | CH$_3$ | OCF$_3$ | pyrid-2-yl | OCF$_3$ |
| 208 | OSO$_2$CH$_3$ | CH$_3$ | OCF$_3$ | pyrid-2-yl | OCF$_3$ |
| 209 | SH | H | OCF$_3$ | pyrid-2-yl | OCF$_3$ |
| 210 | C(=O)OH | H | OCF$_3$ | pyrid-2-yl | OCF$_3$ | where
m, p, q and r are 0; t and u are 1; R is phenyl substituted with R$^{14}$, R$^{15}$, R$^{16}$, R$^{17}$, R$^{18}$;
R$^1$, R$^2$, R$^4$, R$^5$, R$^{14}$, R$^{15}$, R$^{17}$, R$^{18}$, R$^7$, R$^8$, R$^{10}$ and R$^{11}$ are H; A is —CH$_2$—; and X and Y
are taken together with —OCR$^{12}$R$^{13}$O—, forming a 1,3-dioxolane ring:

TABLE 1-continued

I-E

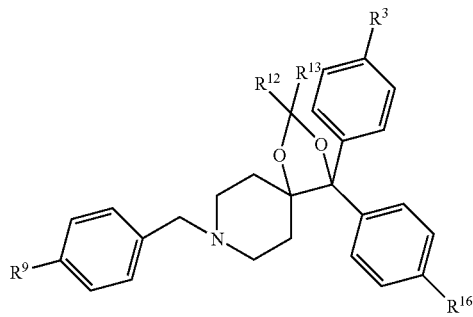

| Compd. No. | $R^3$ | $R^9$ | $R^{12}$ | $R^{13}$ | $R^{16}$ |
| --- | --- | --- | --- | --- | --- |
| 211 | $CF_3$ | pyrid-2-yloxy | H | H | $CF_3$ |
| 212 | $CF_3$ | pyrimidin-2-yloxy | H | H | $CF_3$ |
| 213 | $CF_3$ | 6-chloro-pyridazin-3yloxy | H | H | $CF_3$ |
| 214 | $CF_3$ | 2-ethyl-2H-tetrazol-5-yl | H | H | $CF_3$ |
| 215 | $CF_3$ | $OC_3H_7$ | H | H | $CF_3$ |
| 216 | $CF_3$ | $CH=NOCH_3$ | H | H | $CF_3$ |
| 217 | $CF_3$ | $CH=NOC_2H_5$ | H | H | $CF_3$ |
| 218 | $CF_3$ | pyrid-2-yloxy | $CH_3$ | $CH_3$ | $CF_3$ |
| 219 | $CF_3$ | pyrimidin-2-yloxy | $CH_3$ | $CH_3$ | $CF_3$ |
| 220 | $CF_3$ | 6-chloro-pyridazin-3yloxy | $CH_3$ | $CH_3$ | $CF_3$ |
| 221 | $CF_3$ | 2-ethyl-2H-tetrazol-5-yl | $CH_3$ | $CH_3$ | $CF_3$ |
| 222 | $CF_3$ | $OC_3H_7$ | $CH_3$ | $CH_3$ | $CF_3$ |
| 223 | $CF_3$ | $CH=NOCH_3$ | $CH_3$ | $CH_3$ | $CF_3$ |
| 224 | $CF_3$ | $CH=NOC_2H_5$ | $CH_3$ | $CH_3$ | $CF_3$ |
| 225 | $CF_3$ | $OC(=O)NHCH(CH_3)_2$ | $CH_3$ | $CH_3$ | $CF_3$ | where
m, p, q and r are 0; t and u are 1; r is 1, forming an N-oxide; R is phenyl substituted with $R^{14}$, $R^{15}$, $R^{16}$, $R^{17}$, $R^{18}$; $R^1$, $R^2$, $R^4$, $R^5$, $R^{14}$, $R^{15}$, $R^{17}$, $R^{18}$, $R^7$, $R^8$, $R^{10}$ and $R^{11}$ are H; A is —$CH_2$—; and X and Y are taken together with —$OCR^{12}R^{13}O$—, forming a 1,3-dioxolane ring:

I-F

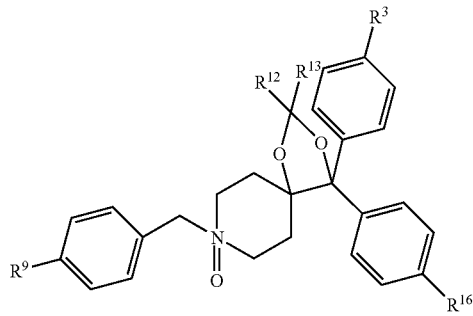

| Compd. No. | $R^3$ | $R^9$ | $R^{12}$ | $R^{13}$ | $R^{16}$ |
| --- | --- | --- | --- | --- | --- |
| 226 | $CF_3$ | pyrid-2-yloxy | H | H | $CF_3$ |
| 227 | $CF_3$ | pyrimidin-2-yloxy | H | H | $CF_3$ |
| 228 | $CF_3$ | 6-chloro-pyridizin-3yloxy | H | H | $CF_3$ |
| 229 | $CF_3$ | 2-ethyl-2H-tetrazol-5-yl | H | H | $CF_3$ |
| 230 | $CF_3$ | $OC_3H_7$ | H | H | $CF_3$ |
| 231 | $CF_3$ | $CH=NOCH_3$ | H | H | $CF_3$ |
| 232 | $CF_3$ | $CH=NOC_2H_5$ | H | H | $CF_3$ |
| 233 | $CF_3$ | pyrid-2-yloxy | $CH_3$ | $CH_3$ | $CF_3$ |
| 234 | $CF_3$ | pyrimidin-2-yloxy | $CH_3$ | $CH_3$ | $CF_3$ |
| 235 | $CF_3$ | 6-chloro-pyridizin-3yloxy | $CH_3$ | $CH_3$ | $CF_3$ |
| 236 | $CF_3$ | 2-ethyl-2H-tetrazol-5-yl | $CH_3$ | $CH_3$ | $CF_3$ |
| 237 | $CF_3$ | $OC_3H_7$ | $CH_3$ | $CH_3$ | $CF_3$ |
| 238 | $CF_3$ | $CH=NOCH_3$ | $CH_3$ | $CH_3$ | $CF_3$ |
| 239 | $CF_3$ | $CH=NOC_2H_5$ | $CH_3$ | $CH_3$ | $CF_3$ |
| 240 | $CF_3$ | $OC(=O)NHCH(CH_3)_2$ | $CH_3$ | $CH_3$ | $CF_3$ | where
p, q and r are 0; t and u are 1; R is phenyl substituted with $R^{14}$, $R^{15}$, $R^{16}$, $R^{17}$, $R^{18}$;
A is —$CH_2$—; and $R^1$, $R^2$, $R^4$, $R^5$, $R^{14}$, $R^{15}$, $R^{17}$, $R^{18}$, $R^7$, $R^8$, $R^{10}$ and $R^{11}$ are H:

TABLE 1-continued

I-G

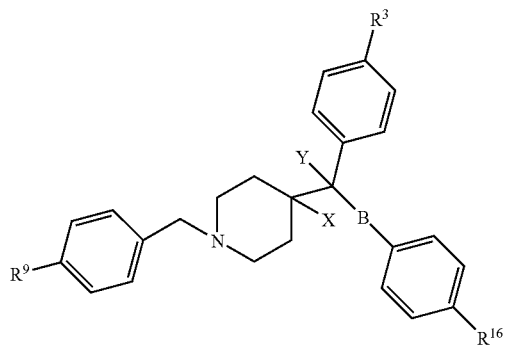

| Compd. No. | R³ | R⁹ | X | Y | B | R¹⁶ |
|---|---|---|---|---|---|---|
| 241 | CF₃ | pyrid-2-yloxy | OH | H | O | CF₃ |
| 242 | CF₃ | pyrid-2-yloxy | OH | CH₃ | O | CF₃ |
| 243 | CF₃ | pyrimidin-2-yloxy | OH | H | O | CF₃ |
| 244 | CF₃ | CH=NOCH₃ | OH | H | O | CF₃ |
| 245 | CF₃ | pyrid-2-yloxy | OH | H | OC(=O)NH | CF₃ |
| 246 | OCF₃ | pyrid-2-yloxy | OH | H | O | OCF₃ |
| 247 | OCF₃ | pyrid-2-yloxy | OH | CH₃ | O | OCF₃ |
| 248 | OCF₃ | pyrid-2-yloxy | F | H | O | OCF₃ |
| 249 | OCF₃ | pyrid-2-yloxy | F | CH₃ | O | OCF₃ |
| 250 | OCF₃ | pyrid-2-yloxy | F | H | OC(=O)NH | OCF₃ |
| 251 | OCF₃ | CH=NOCH₃ | F | H | O | OCF₃ |
| 252 | OCF₃ | pyrid-2-yloxy | OH | H | NHSO₂ | OCF₃ |
| 253 | OCF₃ | pyrid-2-yloxy | OH | H | OCH₂ | OCF₃ |
| 254 | OCF₃ | pyrid-2-yloxy | OH | H | CH₂O | OCF₃ | where
m, p, q and r are 0; t and u are 1; R is phenyl substituted with R¹⁴, R¹⁵, R¹⁶, R¹⁷, R¹⁸;
X is OH; A is —CH₂—; and R¹, R², R⁴, R⁵, R⁷, R⁸, R¹⁰, R¹¹, R¹⁴,
R¹⁵, R¹⁷, R¹⁸ and Y are H:

I-H

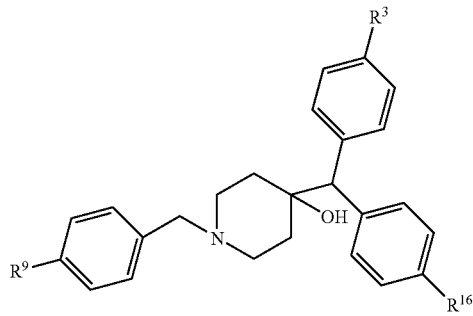

| Compd No. | R³ | R⁹ | R¹⁶ |
|---|---|---|---|
| 255 | OCF₃ | 6-methyl-pyridazin-3-yloxy | OCF₃ |
| 256 | CHO | pyrid-2-yloxy | OCF₃ |
| 257 | C(CH₃)₃ | pyrid-2-yloxy | OCF₃ |
| 258 | OCF₃ | CH=NOCH₂CH₂OCH₂CH₂OCH₃ | OCF₃ |
| 259 | OCF₃ | CH=NOCH₂OCH₂CH₃ | OCF₃ |
| 260 | OCH₃ | pyrid-2-yloxy | OCF₃ |
| 261 | Br | pyrid-2-yloxy | OCF₃ |
| 262 | CH₃ | pyrid-2-yloxy | OCF₃ |
| 263 | OCF₃ | 1,3-dioxolan-2-yl | OCF₃ |
| 264 | CF₃ | 1,3-dioxolan-2-yl | CF₃ |
| 265 | CF₃ | pyrid-2-yloxy | OCF₃ |
| 266 | OCF₃ | CH=NOCH₂CH₂OCH₃ | OCF₃ |
| 267 | Cl | pyrid-2-yloxy | Cl |
| 268 | F | pyrid-2-yloxy | OCF₃ |
| 269 | OCHF₂ | pyrid-2-yloxy | OCF₃ |
| 270 | CF₃ | CH=NOH | CF₃ |
| 271 | OCF₃ | 3-methyl-pyrid-2-yloxy | OCF₃ |
| 272 | OCF₃ | 5-methyl-pyrid-2-yloxy | OCF₃ |
| 273 | OCF₃ | CH(OCH₂CH₃)₂ | OCF₃ |
| 274 | OCF₃ | 6-methoxy-pyridazin-3-yloxy | OCF₃ |

TABLE 1-continued

| | | | |
|---|---|---|---|
| 275 | OCF$_3$ | CH=NOCH$_2$C=N | OCF$_3$ |
| 276 | OCF$_3$ | 6-methyl-pyrid-2-yloxy | OCF$_3$ |
| 277 | OCF$_3$ | C(Cl)=NOCH$_3$ | OCF$_3$ |
| 278 | OCF$_3$ | 4-chlorophenylCH(OH) | OCF$_3$ |
| 279 | OCF$_3$ | OCH$_2$C(=O)OCH$_2$CH$_3$ | OCF$_3$ |
| 280 | OCF$_3$ | 5,5-dimethyl-1,3-dioxan-2-yl | OCF$_3$ |
| 281 | OCF$_3$ | 3-cyano-pyrid-2-yloxy | OCF$_3$ |
| 282 | OCF$_3$ | pyrid-2-yl-CH(OH) | OCF$_3$ |
| 283 | OCF$_3$ | 5-cyano-pyrid-2-yloxy | OCF$_3$ |
| 284 | OCF$_3$ | pyrid-2-yloxy | CH=NOCH$_2$CH=C(CH$_3$)CH$_2$—CH$_2$CH=C(CH$_3$)$_2$ |
| 285 | OCF$_3$ | C(=O)NHOCH$_3$ | OCF$_3$ |
| 286 | OCF$_3$ | 3-chlorophenoxy | OCF$_3$ |
| 287 | OCF$_3$ | pyrid-2-yloxy | CH(OH)CH$_3$ |
| 288 | H | pyrid-2-yloxy | OCF$_3$ |
| 289 | OCF$_3$ | 4-chlorophenyl-CH(OC(=O)CH$_3$) | OCF$_3$ |
| 290 | OCF$_3$ | 4-chlorophenoxy | OCF$_3$ |
| 291 | CF$_3$ | OCH$_2$C(=O)OCH$_2$CH$_3$ | CF$_3$ |
| 292 | OCF$_3$ | 1,3-dioxan-2-yl | OCF$_3$ |
| 293 | OCF$_3$ | OCH$_2$CH=C(Cl)$_2$ | OCF$_3$ |
| 294 | OCF$_3$ | 3-(dimethoxymethyl)-pyrid-2-yl | OCF$_3$ |
| 295 | 1,3-dioxolan-2-yl | pyrid-2-yloxy | OCF$_3$ |
| 296 | OCF$_3$ | C(C=N)=NOCH$_3$ | OCF$_3$ |
| 297 | OCF$_3$ | 2-chlorophenoxy | OCF$_3$ |
| 298 | OCF$_3$ | OC(=O)NH-cyclopropane | OCF$_3$ |
| 299 | CF$_3$ | cyclopropylmethoxy | CF$_3$ |
| 300 | OCF$_3$ | OC(=O)NHC$_3$H$_7$ | OCF$_3$ |
| 301 | OCF$_3$ | CH=NOCH$_2$CF$_3$ | OCF$_3$ |
| 302 | CF$_3$ | OH | CF$_3$ |
| 303 | CF$_3$ | OCH(CH$_3$)$_2$ | CF$_3$ |
| 304 | OCF$_3$ | phenylmethoxy | OCF$_3$ |
| 305 | OCF$_3$ | CH=NHOCH$_2$CH=C(CH$_3$)CH$_2$CH$_2$—CH=C(CH$_3$)$_2$ | OCF$_3$ |
| 306 | OCF$_2$CHFCF$_3$ | pyrimidin-2-yloxy | OCF$_2$CHFCF$_3$ |
| 307 | CF$_3$ | 6-chloro-pyridazin-3-yloxy | CF$_3$ |
| 308 | OCF$_3$ | OCH$_2$CH$_2$OCH$_3$ | OCF$_3$ |
| 309 | OCF$_3$ | pyrid-2-yl | OCF$_3$ |
| 310 | OCF$_3$ | NHC(=O)OCH$_2$CH$_2$CH$_3$ | OCF$_3$ |
| 311 | OCF$_3$ | OC(=O)NHC(CH$_3$)$_3$ | OCF$_3$ |
| 312 | OCF$_3$ | CH=NOCH$_2$CH$_2$F | OCF$_3$ |
| 313 | CF$_3$ | NHC(=O)OCH$_2$CH$_2$CH$_3$ | CF$_3$ |
| 314 | Cl | pyrid-2-yloxy | OCF$_3$ |
| 315 | OCF$_3$ | cyclopropylmethoxy | OCF$_3$ |
| 316 | CF$_3$ | phenylmethoxy | CF$_3$ |
| 317 | OCF$_3$ | OC(=O)NHCH$_2$C(=O)OC$_2$H$_5$ | OCF$_3$ |
| 318 | CF$_3$ | NHC(=O)OCH$_2$CH$_3$ | CF$_3$ |
| 319 | CF$_3$ | NHC(=O)OCH$_2$-cyclopropane | CF$_3$ |
| 320 | OCF$_3$ | OC(=O)NH-cyclopentane | OCF$_3$ |
| 321 | OCF$_3$ | 4-methyl-pyrid-2-yloxy | OCF$_3$ |
| 322 | OCF$_3$ | 3-chloro-pyrid-2-yloxy | OCF$_3$ |
| 323 | OCF$_3$ | OC(=O)NHCH$_2$(3,4-dichlorophenyl) | OCF$_3$ |
| 324 | OCF$_3$ | OC(=O)NH(4-chlorophenyl) | OCF$_3$ |
| 325 | Cl | pyrimidin-2-yloxy | OCF$_3$ |
| 326 | OCF$_3$ | OC(=O)NHC$_4$H$_9$ | OCF$_3$ |
| 327 | OCF$_3$ | NHC(=O)OCH$_2$-cyclopropane | OCF$_3$ |
| 328 | Cl | CH=NOC$_2$H$_5$ | OCF$_3$ |
| 329 | OCF$_3$ | OC(=O)NH-cyclohexane | OCF$_3$ |
| 330 | CF$_3$ | C(=O)OCH(CH$_3$)$_2$ | CF$_3$ |
| 331 | CF$_3$ | OH | CF$_3$ |
| 332 | OCF$_3$ | NHC(=O)C(CH$_2$CH$_2$)C=N | OCF$_3$ |
| 333 | CF$_3$ | NHC(=O)C(CH$_2$CH$_2$)C=N | CF$_3$ | where
m, p, and q are 0; t and u are 1; r is 1, forming an N-oxide; R is phenyl substituted with $R^{14}$, $R^{15}$, $R^{16}$, $R^{17}$, $R^{18}$; X is OH, A is —CH$_2$—; and $R^1$, $R^2$, $R^4$, $R^5$, $R^7$, $R^8$, $R^{10}$, $R^{11}$, $R^{14}$, $R^{15}$, $R^{17}$, $R^{18}$ and Y are H:

TABLE 1-continued

I-J

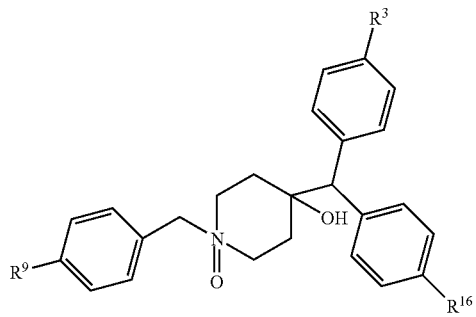

| Compd No. | R³ | R⁹ | R¹⁶ |
| --- | --- | --- | --- |
| 334 | CHO | pyrid-2-yloxy | OCF₃ |
| 335 | C(CH₃)₃ | pyrid-2-yloxy | OCF₃ |
| 336 | OCF₃ | CH=NOCH₂CH₂OCH₂CH₂OCH₃ | OCF₃ |
| 337 | OCF₃ | CH=NOCH₂OCH₂CH₃ | OCF₃ |
| 338 | OCH₃ | pyrid-2-yloxy | OCF₃ |
| 339 | Br | pyrid-2-yloxy | OCF₃ |
| 340 | CH₃ | pyrid-2-yloxy | OCF₃ |
| 341 | OCF₃ | 1,3-dioxolan-2-yl | OCF₃ |
| 342 | CF₃ | 1,3-dioxolan-2-yl | CF₃ |
| 343 | CF₃ | pyrid-2-yloxy | OCF₃ |
| 344 | OCF₃ | CH=NOCH₂CH₂OCH₃ | OCF₃ |
| 345 | Cl | pyrid-2-yloxy | Cl |
| 346 | F | pyrid-2-yloxy | OCF₃ |
| 347 | OCHF₂ | pyrid-2-yloxy | OCF₃ |
| 348 | CF₃ | CH=NOH | CF₃ |
| 349 | OCF₃ | 3-methyl-pyrid-2-yloxy | OCF₃ |
| 350 | OCF₃ | 5-methyl-pyrid-2-yloxy | OCF₃ |
| 351 | OCF₃ | CH(OCH₂CH₃)₂ | OCF₃ |
| 352 | OCF₃ | 6-methoxy-pyridazin-3-yloxy | OCF₃ |
| 353 | OCF₃ | CH=NOCH₂C≡N | OCF₃ |
| 354 | OCF₃ | 6-methyl-pyrid-2-yloxy | OCF₃ |
| 355 | OCF₃ | C(Cl)=NOCH₃ | OCF₃ |
| 356 | OCF₃ | 4-chlorophenylCH(OH) | OCF₃ |
| 357 | OCF₃ | OCH₂C(=O)OCH₂CH₃ | OCF₃ |
| 358 | OCF₃ | 5,5-dimethyl-1,3-dioxan-2-yl | OCF₃ |
| 359 | OCF₃ | 3-cyano-pyrid-2-yloxy | OCF₃ |
| 360 | OCF₃ | pyrid-2-yl-CH(OH) | OCF₃ |
| 361 | OCF₃ | 5-cyano-pyrid-2-yloxy | OCF₃ |
| 362 | OCF₃ | pyrid-2-yloxy | CH=NOCH₂CH=C(CH₃)CH₂—CH₂CH=C(CH₃)₂ |
| 363 | OCF₃ | C(=O)NHOCH₃ | OCF₃ |
| 364 | OCF₃ | 3-chlorophenoxy | OCF₃ |
| 365 | OCF₃ | pyrid-2-yloxy | CH(OH)CH₃ |
| 366 | H | pyrid-2-yloxy | OCF₃ |
| 367 | OCF₃ | 4-chlorophenyl-CH(OC(=O)CH₃) | OCF₃ |
| 368 | OCF₃ | 4-chlorophenoxy | OCF₃ |
| 369 | CF₃ | OCH₂C(=O)OCH₂CH₃ | CF₃ |
| 370 | OCF₃ | 1,3-dioxan-2-yl | OCF₃ |
| 371 | OCF₃ | OCH₂CH=C(Cl)₂ | OCF₃ |
| 372 | OCF₃ | 3-(dimethoxymethyl)-pyrid-2-yl | OCF₃ |
| 373 | 1,3-dioxolan-2-yl | pyrid-2-yloxy | OCF₃ |
| 374 | OCF₃ | C(C≡N)=NOCH₃ | OCF₃ |
| 375 | OCF₃ | 2-chlorophenoxy | OCF₃ |
| 376 | OCF₃ | OC(=O)NH-cyclopropane | OCF₃ |
| 377 | OCF₃ | OC(=O)NHC₃H₇ | OCF₃ |
| 378 | OCF₃ | CH=NOCH₂CF₃ | OCF₃ |
| 379 | CF₃ | OH | CF₃ |
| 380 | CF₃ | OCH(CH₃)₂ | CF₃ |
| 381 | OCF₃ | phenylmethoxy | OCF₃ |
| 382 | OCF₃ | CH=NHOCH₂CH=C(CH₃)CH₂CH₂—CH=C(CH₃)₂ | OCF₃ |
| 383 | CF₃ | cyclopropylmethoxy | CF₃ |
| 384 | CF₃ | 6-chloro-pyridazin-3-yloxy | CF₃ |
| 385 | OCF₃ | OCH₂CH₂OCH₃ | OCF₃ |
| 386 | OCF₃ | pyrid-2-yl | OCF₃ |
| 387 | OCF₃ | NHC(=O)OCH₂CH₂CH₃ | OCF₃ |
| 388 | OCF₃ | OC(=O)NHC(CH₃)₃ | OCF₃ |
| 389 | OCF₃ | CH=NOCH₂CH₂F | OCF₃ |
| 390 | CF₃ | NHC(=O)OCH₂CH₂CH₃ | CF₃ |

TABLE 1-continued

| | | | |
|---|---|---|---|
| 391 | Cl | pyrid-2-yloxy | OCF$_3$ |
| 392 | OCF$_3$ | cyclopropylmethoxy | OCF$_3$ |
| 393 | CF$_3$ | phenylmethoxy | CF$_3$ |
| 394 | OCF$_3$ | OC(=O)NHCH$_2$C(=O)OC$_2$H$_5$ | OCF$_3$ |
| 395 | CF$_3$ | NHC(=O)OCH$_2$CH$_3$ | CF$_3$ |
| 396 | CF$_3$ | NHC(=O)OCH$_2$-cyclopropane | CF$_3$ |
| 397 | OCF$_3$ | OC(=O)NH-cyclopentane | OCF$_3$ |
| 398 | OCF$_3$ | 4-methyl-pyrid-2-yloxy | OCF$_3$ |
| 399 | OCF$_3$ | 3-chloro-pyrid-2-yloxy | OCF$_3$ |
| 400 | OCF$_3$ | OC(=O)NHCH$_2$(3,4-dichlorophenyl) | OCF$_3$ |
| 401 | OCF$_3$ | OC(=O)NH(4-chlorophenyl) | OCF$_3$ |
| 402 | Cl | pyrimidin-2-yloxy | OCF$_3$ |
| 403 | OCF$_3$ | OC(=O)NHC$_4$H$_9$ | OCF$_3$ |
| 404 | OCF$_3$ | NHC(=O)OCH$_2$-cyclopropane | OCF$_3$ |
| 405 | Cl | CH=NOC$_2$H$_5$ | OCF$_3$ |
| 406 | OCF$_3$ | OC(=O)NH-cyclohexane | OCF$_3$ |
| 407 | CF$_3$ | C(=O)OCH(CH$_3$)$_2$ | CF$_3$ |
| 408 | CF$_3$ | OH | CF$_3$ |
| 409 | OCF$_2$CHFCF$_3$ | pyrimidin-2-yloxy | OCF$_2$CHFCF$_3$ |
| 410 | OCF$_3$ | CH=NOCH$_2$C(=O)NH$_2$ | OCF$_3$ |
| 411 | OCF$_3$ | 3-chloro-pyrid-2-yl | OCF$_3$ |
| 412 | OCF$_3$ | 6-chloro-pyridazin-3-yloxy | OCF$_3$ |
| 413 | OCF$_3$ | 6-methyl-pyridazin-3-yloxy | OCF$_3$ |
| 414 | OCF$_3$ | NHC(=O)C(CH$_2$CH$_2$)C≡N | OCF$_3$ |
| 415 | CF$_3$ | NHC(=O)C(CH$_2$CH$_2$)C≡N | CF$_3$ | where
m, p, q and r are 0; t and u are 1; R is phenyl substituted with $R^{14}$, $R^{15}$, $R^{16}$, $R^{17}$, $R^{18}$; X and Y are OH; $R^3$ and $R^{16}$ are OCF$_3$; A is —CH$_2$—; and $R^1$, $R^2$, $R^4$, $R^5$, $R^{14}$, $R^{15}$, $R^{17}$, $R^{18}$, $R^7$, $R^8$, $R^{10}$, and $R^{11}$ are H:

I-K

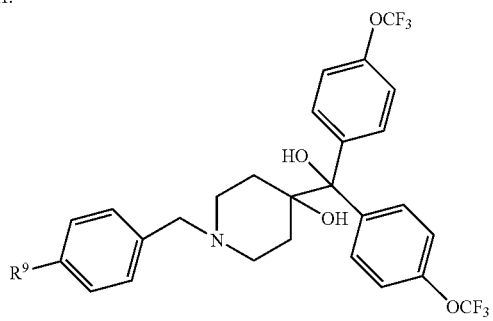

| Compd. No. | $R^9$ |
|---|---|
| 416 | 2-ethyl-2H-tetrazol-5-yl |
| 417 | CH=NOCH$_2$CH$_3$ |
| 418 | CHO |
| 419 | NHC(=O)OCH(CH$_3$)$_2$ |
| 420 | NHC(=O)C(CH$_2$CH$_2$)C≡N | where
m, p, and q are 0; t and u are 1; r is 1, forming an N-oxide; R is phenyl substituted with $R^{14}$, $R^{15}$, $R^{16}$, $R^{17}$, $R^{18}$; A is —CH$_2$—; and $R^1$, $R^2$, $R^4$, $R^5$, $R^{14}$, $R^{15}$, $R^{17}$, $R^{18}$, $R^7$, $R^8$, $R^{10}$, and $R^{11}$ are H:

I-L

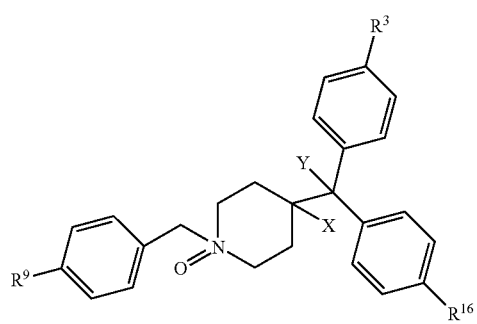

| Compd. No. | $R^3$ | $R^9$ | $R^{16}$ | X | Y |
|---|---|---|---|---|---|
| 421 | OCF$_3$ | pyrid-2-yloxy | OCF$_3$ | OH | OH |
| 422 | OCF$_3$ | pyrimidin-2-yloxy | OCF$_3$ | OH | OH |

TABLE 1-continued

| | | | | | |
|---|---|---|---|---|---|
| 423 | OCF$_3$ | NHC(=O)OCH(CH$_3$)$_2$ | OCF$_3$ | OH | OH |
| 424 | OCF$_3$ | CH=NOCH$_2$CH$_3$ | OCF$_3$ | OH | OH |
| 425 | OCF$_3$ | 6-chloro-pyridazin-3-yloxy | OCF$_3$ | OH | OH |
| 426 | OCF$_3$ | 2-ethyl-2H-tetrazol-5-yl | OCF$_3$ | OH | OH |
| 428 | OCF$_3$ | NHC(=O)C(CH$_2$CH$_2$)C≡N | OCF$_3$ | OH | OH |
| 429 | CF$_3$ | NHC(=O)C(CH$_2$CH$_2$)C≡N | CF$_3$ | OH | F |
| 430 | OCF$_3$ | pyrid-2-yloxy | OCF$_3$ | OH | F |
| 431 | OCF$_3$ | pyrid-2-yloxy | OCF$_3$ | | X and Y taken together with bridging group —O— |
| 432 | OCF$_3$ | pyrimidin-2-yloxy | OCF$_3$ | | X and Y taken together with bridging group —O— | where
m, p, q and r are 0; t and u are 1; R is phenyl substituted with $R^{14}$, $R^{15}$, $R^{16}$, $R^{17}$, $R^{18}$;
A is —CH$_2$—; and $R^7$, $R^8$, $R^{11}$, $R^{14}$ and Y are H:

I-M

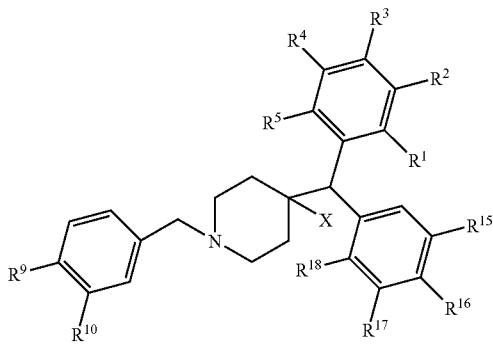

| Compd No. | $R^1$ | $R^2$ | $R^3$ | $R^4$ | $R^5$ | $R^9$ | $R^{10}$ | $R^{15}$ | $R^{16}$ | $R^{17}$ | $R^{18}$ | X |
|---|---|---|---|---|---|---|---|---|---|---|---|---|
| 433 | Cl | H | Cl | H | H | pyrid-2-yloxy | H | H | OCF$_3$ | H | H | OH |
| 434 | F | H | H | H | H | pyrimidin-2-yloxy | H | H | H | H | F | OH |
| 435 | H | CH$_3$ | Cl | H | H | pyrid-2-yloxy | H | H | OCF$_3$ | H | H | OH |
| 436 | CH$_3$ | H | Cl | H | H | pyrid-2-yloxy | H | H | OCF$_3$ | H | H | OH |
| 437 | Cl | H | H | H | H | pyrid-2-yloxy | H | H | OCF$_3$ | H | H | OH |
| 438 | Cl | Cl | H | H | H | pyrid-2-yloxy | H | H | OCF$_3$ | H | H | OH |
| 439 | H | Cl | H | H | H | pyrid-2-yloxy | H | H | OCF$_3$ | H | H | OH |
| 440 | H | H | CH=NO—C$_2$H$_5$ | H | H | pyrid-2-yloxy | H | H | OCF$_3$ | H | H | OH |
| 441 | H | Cl | Cl | H | H | pyrid-2-yloxy | H | H | OCF$_3$ | H | H | OH |
| 442 | H | Cl | H | Cl | H | pyrid-2-yloxy | H | H | OCF$_3$ | H | H | OH |
| 443 | Cl | H | H | Cl | H | pyrid-2-yloxy | H | H | OCF$_3$ | H | H | OH |
| 444 | Cl | H | Cl | H | H | CH=NOC$_2$H$_5$ | H | H | OCF$_3$ | H | H | OH |
| 445 | F | H | Cl | H | H | pyrid-2-yloxy | H | H | OCF$_3$ | H | H | OH |
| 446 | H | H | $R^3$ and $R^4$ taken together with bridging group —OC(F$_2$)O— | H | H | pyrid-2-yloxy | H | H | $R^{16}$ and $R^{17}$ taken together with bridging group —OC(F$_2$)O— | H | OH |
| 447 | H | H | OCF$_3$ | H | H | pyrid-2-yloxy | OCH$_3$ | H | OCF$_3$ | H | H | OH |
| 448 | H | H | CF$_3$ | H | H | pyrimidin-2-yloxy | H | H | CF$_3$ | H | H | CH$_2$OH |
| 449 | H | H | CF$_3$ | H | H | OCH$_2$-cyclopropane | H | H | CF$_3$ | H | H | CH$_2$N=N=N |
| 450 | H | H | CF$_3$ | H | H | OCH$_2$-cyclopropane | H | H | CF$_3$ | H | H | CH$_2$NH$_2$ |
| 451 | H | H | CF$_3$ | H | H | pyrimidin-2-yloxy | H | H | CF$_3$ | H | H | CH$_2$NH—C(=O)—CH$_3$ |
| 452 | H | H | CF$_3$ | H | H | pyrimidin-2-yloxy | H | H | CF$_3$ | H | H | CH$_2$O—C(=O)—CH$_3$ | where
m, p, and q are 0; t and u are 1; r is 1, forming an N-oxide; R is phenyl substituted
with $R^{14}$, $R^{15}$, $R^{16}$, $R^{17}$, $R^{18}$; A is —CH$_2$—; and $R^7$, $R^8$, $R^{11}$, $R^{14}$
and Y are H:

TABLE 1-continued

I-N

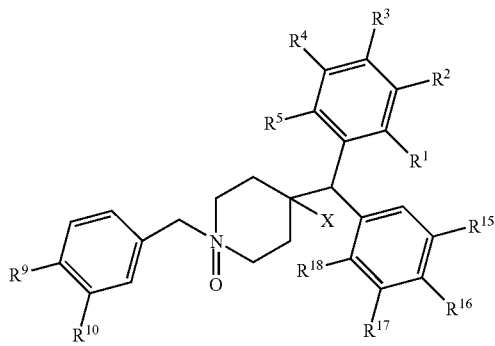

| Compd No. | R¹ | R² | R³ | R⁴ | R⁵ | R⁹ | R¹⁰ | R¹⁵ | R¹⁶ | R¹⁷ | R¹⁸ | X |
|---|---|---|---|---|---|---|---|---|---|---|---|---|
| 453 | Cl | H | Cl | H | H | CH=NOC₂H₅ | H | H | OCF₃ | H | H | OH |
| 454 | Cl | H | Cl | H | H | pyrid-2-yloxy | H | H | OCF₃ | H | H | OH |
| 455 | H | Cl | Cl | H | H | pyrid-2-yloxy | H | H | OCF₃ | H | H | OH |
| 456 | Cl | H | H | H | H | pyrid-2-yloxy | H | H | OCF₃ | H | H | OH |
| 457 | H | Cl | H | Cl | H | pyrid-2-yloxy | H | H | OCF₃ | H | H | OH |
| 458 | H | Cl | H | H | H | pyrid-2-yloxy | H | H | OCF₃ | H | H | OH |
| 459 | Cl | H | H | H | H | pyrid-2-yloxy | H | H | OCF₃ | H | H | OH |
| 460 | Cl | H | H | Cl | H | pyrid-2-yloxy | H | H | OCF₃ | H | H | OH |
| 461 | CH₃ | H | Cl | H | H | pyrid-2-yloxy | H | H | OCF₃ | H | H | OH |
| 462 | H | CH₃ | Cl | H | H | pyrid-2-yloxy | H | H | OCF₃ | H | H | OH |
| 463 | F | H | Cl | H | H | pyrid-2-yloxy | H | H | OCF₃ | H | H | OH |
| 464 | H | R² and R³ taken together with bridging group —OC(F₂)O— | | H | H | pyrid-2-yloxy | H | R¹⁵ and R¹⁶ taken together with bridging group —OC(F₂)O— | | H | H | OH |
| 465 | H | H | OCF₃ | H | H | pyrid-2-yloxy | OCH₃ | H | OCF₃ | H | H | OH |
| 466 | H | H | CF₃ | H | H | pyrimidin-2-yloxy | H | H | CF₃ | H | H | CH₂NH—C(=O)—CH₃ |
| 467 | H | H | CF₃ | H | H | OCH₂-cyclopropane | H | H | CF₃ | H | H | CH₂N=N=N |
| 468 | H | H | CF₃ | H | H | pyrimidin-2-yloxy | H | H | CF₃ | H | H | CH₂O—C(=O)—CH₃ | where
m, p, q and r are 0; t and u are 1; R is phenyl substituted with R¹⁴, R¹⁵, R¹⁶, R¹⁷, R¹⁸; R³ and R¹⁶ are OCF₃; and R¹, R², R⁴, R⁵, R¹⁴, R¹⁵, R¹⁷, R¹⁸, R¹⁰ and R¹¹ are H:

I-P

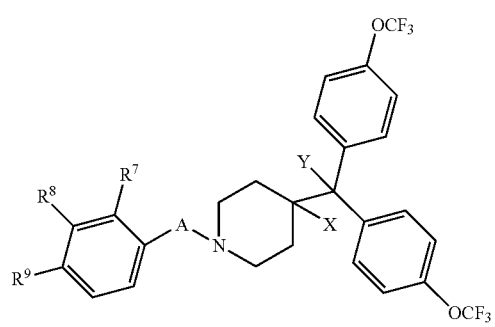

| Compd. No. | X | Y | A | R⁷ | R⁸ | R⁹ |
|---|---|---|---|---|---|---|
| 470 | OH | H | OCH₂CH(OH)CH₂ | H | H | Cl |
| 471 | OH | H | OCH₂CH(OH)CH₂ | H | Cl | H |
| 472 | OH | H | OCH₂CH(OH)CH₂ | Cl | H | H |
| 473 | OH | H | OCH₂CH₂CH₂ | H | H | Cl |
| 474 | OH | H | CH₂CH₂ | H | H | Cl |
| 475 | OH | H | OCH₂CH₂ | H | H | Cl |
| 476 | OH | H | OCH₂CH₂CH₂CH₂ | H | H | Cl |
| 477 | OH | H | OCH₂CH₂ | H | H | Br | where
m, p, and q are 0; t and u are 1; r is 1, forming an N-oxide; R is phenyl substituted with R¹⁴, R¹⁵, R¹⁶, R¹⁷, R¹⁸; R³ and R¹⁶ are OCF₃; and R¹, R², R⁴, R⁵, R⁷, R⁸, R¹⁰, R¹¹, R¹⁴, R¹⁵, R¹⁷, R¹⁸ and Y are H:

TABLE 1-continued

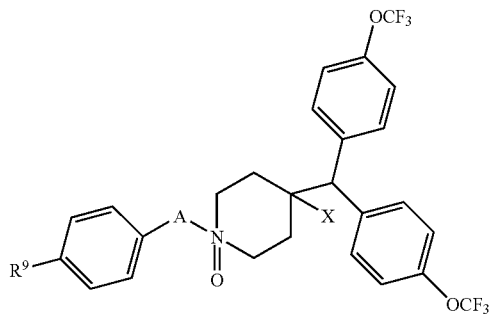

I-Q

| Compd. No. | X | A | $R^9$ |
|---|---|---|---|
| 478 | OH | $OCH_2CH_2$ | Cl |
| 479 | OH | $CH_2CH_2$ | Cl |
| 480 | OH | $OCH_2CH_2CH_2CH_2$ | Cl |
| 481 | OH | $OCH_2CH_2CH_2$ | Cl |
| 482 | OH | $OCH_2CH_2$ | Br | where
m, p, and q are 0; t and u are 1; r is 1, R is phenyl substituted with $R^{14}$, $R^{15}$, $R^{16}$, $R^{17}$, $R^{18}$;
X is OH; A is —$CH_2$—; and $R^1$, $R^2$, $R^4$, $R^5$, $R^7$, $R^8$, $R^{10}$, $R^{11}$, $R^{14}$, $R^{15}$, $R^{17}$, $R^{18}$ and Y are H:

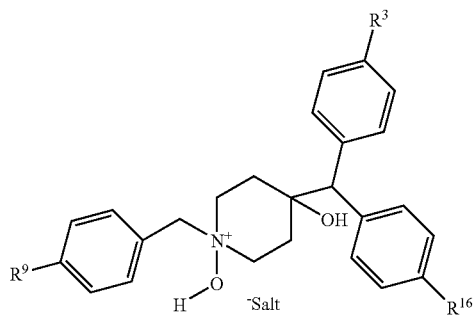

I-R

| Compd No. | $R^3$ | $R^9$ | $R^{16}$ | ⁻Salt |
|---|---|---|---|---|
| 483 | $OCF_3$ | CH=$NOC_2H_5$ | $OCF_3$ | 3-hydroxypropanesulfonic acid |
| 484 | $OCF_3$ | CH=$NOC_2H_5$ | $OCF_3$ | 2-ethoxypropanoic acid |
| 485 | $OCF_3$ | 6-chloro-pyridazin-3-yloxy | $OCF_3$ | 2-ethylhexanoic acid |
| 486 | $OCF_3$ | CH=$NOC_2H_5$ | $OCF_3$ | 2-ethylhexanoic acid |
| 487 | $OCF_3$ | CH=$NOC_2H_5$ | $OCF_3$ | 1,1,2,2,3,3,4,4,4-nonafluorobutanesulfonic acid |
| 488 | $CF_3$ | 6-chloro-pyridazin-3-yloxy | $CF_3$ | 2-hydroxypropane-1,2,3-tricarboxylic acid |
| 489 | $OCF_3$ | CH=$NOCH_2C(=O)NH_2$ | $OCF_3$ | 2-hydroxypropane-1,2,3-tricarboxylic acid |
| 490 | $OCF_3$ | CH=$NOC_2H_5$ | $OCF_3$ | ((4R)-7,7-dimethyl-2-oxobicyclo[2.2.1]heptyl)methanesulfonic acid |
| 491 | $OCF_3$ | CH=$NOC_2H_5$ | $OCF_3$ | ethanesulfonic acid |
| 492 | $OCF_3$ | 6-chloro-pyridazin-3-yloxy | $OCF_3$ | 2-hydroxypropane-1,2,3-tricarboxylic acid |
| 493 | $OCF_3$ | CH=$NOC_2H_5$ | $OCF_3$ | cyclohexanecarboxylic acid |
| 494 | $OCF_3$ | CH=$NOC_2H_5$ | $OCF_3$ | 2-hydroxypropane-1,2,3-tricarboxylic acid |
| 495 | $OCF_3$ | CH=$NOC_2H_5$ | $OCF_3$ | 1,1,2,2,3,3,4,4,5,5,6,6,7,7,8,8,8-heptadecafluorooctanesulfonic acid |
| 496 | $OCF_3$ | pyrid-2-yloxy | $OCF_3$ | 1,1,2,2,3,3,4,4,5,5,6,6,7,7,8,8,8-heptadecafluorooctanesulfonic acid |
| 497 | $OCF_3$ | pyrid-2-yloxy | $OCF_3$ | ⁻Cl |
| 498 | $OCF_3$ | pyrid-2-yloxy | $OCF_3$ | ((4S)-7,7-dimethyl-2-oxobicyclo[2.2.1]heptyl)methanesulfonic acid |
| 499 | $OCF_3$ | pyrid-2-yloxy | $OCF_3$ | 2-ethylhexanoic acid |
| 500 | $OCF_3$ | pyrid-2-yloxy | $OCF_3$ | 3-hydroxypropanesulfonic acid |
| 501 | $OCF_3$ | CH(Cl)=$NOCH_3$ | $OCF_3$ | 2-hydroxypropane-1,2,3-tricarboxylic acid |
| 502 | $OCF_3$ | pyrid-2-yloxy | $OCF_3$ | cyclohexanecarboxylic acid |
| 503 | $OCF_3$ | pyrid-2-yloxy | $OCF_3$ | 2-ethoxypropanoic acid |
| 504 | $OCF_3$ | pyrid-2-yloxy | $OCF_3$ | 2-hydroxypropane-1,2,3-tricarboxylic acid |
| 505 | $OCF_3$ | pyrid-2-yloxy | $OCF_3$ | ((4R)-7,7-dimethyl-2-oxobicyclo[2.2.1]heptyl)methanesulfonic acid |
| 506 | $OCF_3$ | pyrid-2-yloxy | $OCF_3$ | ethanesulfonic acid |
| 507 | $OCF_3$ | CH=$NOC_2H_5$ | $OCF_3$ | ((4R)-7,7-dimethyl-2-oxobicyclo[2.2.1]heptyl)methanesulfonic acid |
| 508 | $OCF_3$ | pyrid-2-yloxy | $OCF_3$ | 1,1,2,2,3,3,4,4,4-nonafluorobutanesulfonic acid |

TABLE 1-continued

| | | | | |
|---|---|---|---|---|
| 509 | $OCF_3$ | pyrid-2-yloxy | $OCF_3$ | 3,7-dimethyloct-6-enoic acid |
| 510 | $OCF_3$ | pyrid-2-yloxy | $OCF_3$ | 2-hydroxyacetic acid |
| 511 | $OCF_3$ | pyrid-2-yloxy | $OCF_3$ | adamantanecarboxylic acid |
| 512 | $OCF_3$ | pyrid-2-yloxy | $OCF_3$ | pentanedioic acid |
| 513 | $OCF_3$ | pyrid-2-yloxy | $OCF_3$ | (9E)octadec-9-enoic acid |
| 514 | $OCF_3$ | pyrid-2-yloxy | $OCF_3$ | heptanedioic acid |
| 515 | $OCF_3$ | pyrid-2-yloxy | $OCF_3$ | 4-dodecylbenzenesulfonic acid |
| 516 | $OCF_3$ | pyrid-2-yloxy | $OCF_3$ | hexanedioic acid |
| 517 | $OCF_3$ | pyrid-2-yloxy | $OCF_3$ | octanoic acid |
| 518 | $CF_3$ | 6-chloro-pyridazin-3-yloxy | $CF_3$ | ethanesulfonic acid |
| 519 | $CF_3$ | 6-chloro-pyridazin-3-yloxy | $CF_3$ | 3-((1Z)-2-chloro-3,3,3-trifluoroprop-1-enyl)-2,2-dimethylcyclopropanecarboxylic acid |
| 520 | $CF_3$ | 6-chloro-pyridazin-3-yloxy | $CF_3$ | 1,1,2,2,3,3,4,4,5,5,6,6,7,7,8,8,9,9,9-nonadecafluorononanesulfonic acid | where
m, p and r are 0; t and u are 1; R is phenyl substituted
with $R^{14}$, $R^{15}$, $R^{16}$, $R^{17}$, $R^{18}$;
X is OH; A is —$CH_2$—; $R^3$ and $R^{16}$ are $OCF_3$; and $R^1$, $R^2$, $R^4$, $R^5$, $R^7$, $R^8$, $R^{10}$, $R^{11}$, $R^{14}$, $R^{15}$, $R^{17}$ and $R^{18}$ are H:

I-S

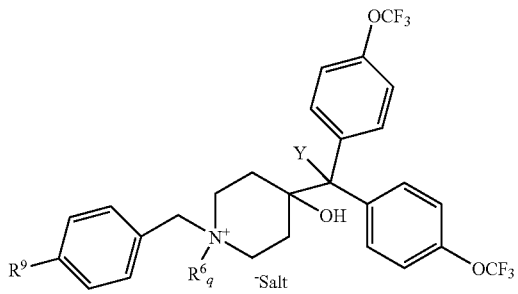

| Compd No. | q | Y | $R^6$ | $R^9$ | ⁻Salt |
|---|---|---|---|---|---|
| 521 | 1 | OH | (methylethoxy)-carboxamide-phenyl-4-meth-yl | NHC(=O)OCH(CH$_3$)$_2$ | ⁻Cl |
| 522 | 0 | H | — | pyrid-2-yloxy | H•⁻Cl | where
m, p, and q are 0; t and u are 1; R is phenyl substituted
with $R^{14}$, $R^{15}$, $R^{16}$, $R^{17}$, $R^{18}$;
$R^1$, $R^2$, $R^4$, $R^5$, $R^{14}$, $R^{15}$, $R^{17}$, $R^{18}$, $R^7$, $R^8$, $R^{10}$ and $R^{11}$ are H;
A is —$CH_2$—; and X and Y are taken together with —OC(=O)O—, forming a 1,3 dioxol-2-one ring:

I-T

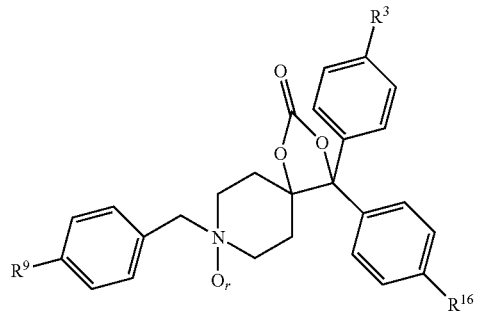

note if r = 1, the n-oxide is formed:

| Compd. No. | r | $R^3$ | $R^9$ | $R^{16}$ |
|---|---|---|---|---|
| 523 | 0 | $CF_3$ | pyrid-2-yloxy | $CF_3$ |
| 524 | 0 | $CF_3$ | pyrimidin-2-yloxy | $CF_3$ |
| 525 | 0 | $CF_3$ | 6-chloro-pyridazin-3yloxy | $CF_3$ |
| 526 | 0 | $CF_3$ | 2-ethyl-2H-tetrazol-5-yl | $CF_3$ |
| 527 | 0 | $CF_3$ | $OC_3H_7$ | $CF_3$ |
| 528 | 0 | $CF_3$ | CH=$NOCH_3$ | $CF_3$ |
| 529 | 0 | $CF_3$ | CH=$NOC_2H_5$ | $CF_3$ |
| 530 | 0 | $CF_3$ | pyrid-2-yloxy | $CF_3$ |
| 531 | 0 | $CF_3$ | pyrimidin-2-yloxy | $CF_3$ |
| 532 | 0 | $CF_3$ | 6-chloro-pyridazin-3yloxy | $CF_3$ |
| 533 | 0 | $CF_3$ | 2-ethyl-2H-tetrazol-5-yl | $CF_3$ |

TABLE 1-continued

| | | | | |
|---|---|---|---|---|
| 534 | 0 | CF$_3$ | OC$_3$H$_7$ | CF$_3$ |
| 535 | 0 | CF$_3$ | CH=NOCH$_3$ | CF$_3$ |
| 536 | 0 | CF$_3$ | CH=NOC$_2$H$_5$ | CF$_3$ |
| 537 | 0 | CF$_3$ | OC(=O)NHCH(CH$_3$)$_2$ | CF$_3$ |
| 538 | 1 | CF$_3$ | pyrid-2-yloxy | CF$_3$ |
| 539 | 1 | CF$_3$ | pyrimidin-2-yloxy | CF$_3$ |
| 540 | 1 | CF$_3$ | 6-chloro-pyridazin-3yloxy | CF$_3$ |
| 541 | 1 | CF$_3$ | 2-ethyl-2H-tetrazol-5-yl | CF$_3$ |
| 542 | 1 | CF$_3$ | OC$_3$H$_7$ | CF$_3$ |
| 543 | 1 | CF$_3$ | CH=NOCH$_3$ | CF$_3$ |
| 544 | 1 | CF$_3$ | CH=NOC$_2$H$_5$ | CF$_3$ |
| 545 | 1 | CF$_3$ | pyrid-2-yloxy | CF$_3$ |
| 546 | 1 | CF$_3$ | pyrimidin-2-yloxy | CF$_3$ |
| 547 | 1 | CF$_3$ | 6-chloro-pyridazin-3yloxy | CF$_3$ |
| 548 | 1 | CF$_3$ | 2-ethyl-2H-tetrazol-5-yl | CF$_3$ |
| 549 | 1 | CF$_3$ | OC$_3$H$_7$ | CF$_3$ |
| 550 | 1 | CF$_3$ | CH=NOCH$_3$ | CF$_3$ |
| 551 | 1 | CF$_3$ | CH=NOC$_2$H$_5$ | CF$_3$ |
| 552 | 1 | CF$_3$ | OC(=O)NHCH(CH$_3$)$_2$ | CF$_3$ |
| 553 | 0 | OCF$_3$ | pyrid-2-yloxy | OCF$_3$ |
| 554 | 0 | OCF$_3$ | pyrimidin-2-yloxy | OCF$_3$ |
| 555 | 0 | OCF$_3$ | 6-chloro-pyridazin-3yloxy | OCF$_3$ |
| 556 | 0 | OCF$_3$ | 2-ethyl-2H-tetrazol-5-yl | OCF$_3$ |
| 557 | 0 | OCF$_3$ | OC$_3$H$_7$ | OCF$_3$ |
| 558 | 0 | OCF$_3$ | CH=NOCH$_3$ | OCF$_3$ |
| 559 | 0 | OCF$_3$ | CH=NOC$_2$H$_5$ | OCF$_3$ |
| 560 | 0 | OCF$_3$ | pyrid-2-yloxy | OCF$_3$ |
| 561 | 0 | OCF$_3$ | pyrimidin-2-yloxy | OCF$_3$ |
| 562 | 0 | OCF$_3$ | 6-chloro-pyridazin-3yloxy | OCF$_3$ |
| 563 | 0 | OCF$_3$ | 2-ethyl-2H-tetrazol-5-yl | OCF$_3$ |
| 564 | 0 | OCF$_3$ | OC$_3$H$_7$ | OCF$_3$ |
| 565 | 0 | OCF$_3$ | CH=NOCH$_3$ | OCF$_3$ |
| 566 | 0 | OCF$_3$ | CH=NOC$_2$H$_5$ | OCF$_3$ |
| 567 | 0 | OCF$_3$ | OC(=O)NHCH(CH$_3$)$_2$ | OCF$_3$ |
| 568 | 1 | OCF$_3$ | pyrid-2-yloxy | OCF$_3$ |
| 569 | 1 | OCF$_3$ | pyrimidin-2-yloxy | OCF$_3$ |
| 570 | 1 | OCF$_3$ | 6-chloro-pyridazin-3yloxy | OCF$_3$ |
| 571 | 1 | OCF$_3$ | 2-ethyl-2H-tetrazol-5-yl | OCF$_3$ |
| 572 | 1 | OCF$_3$ | OC$_3$H$_7$ | OCF$_3$ |
| 573 | 1 | OCF$_3$ | CH=NOCH$_3$ | OCF$_3$ |
| 574 | 1 | OCF$_3$ | CH=NOC$_2$H$_5$ | OCF$_3$ |
| 575 | 1 | OCF$_3$ | pyrid-2-yloxy | OCF$_3$ |
| 576 | 1 | OCF$_3$ | pyrimidin-2-yloxy | OCF$_3$ |
| 577 | 1 | OCF$_3$ | 6-chloro-pyridazin-3yloxy | OCF$_3$ |
| 578 | 1 | OCF$_3$ | 2-ethyl-2H-tetrazol-5-yl | OCF$_3$ |
| 579 | 1 | OCF$_3$ | OC$_3$H$_7$ | OCF$_3$ |
| 580 | 1 | OCF$_3$ | CH=NOCH$_3$ | OCF$_3$ |
| 581 | 1 | OCF$_3$ | CH=NOC$_2$H$_5$ | OCF$_3$ |
| 582 | 1 | OCF$_3$ | OC(=O)NHCH(CH$_3$)$_2$ | OCF$_3$ | where
m, p, q and r are 0; t and u are 1; R is phenyl substituted
with R$^{14}$, R$^{15}$, R$^{16}$, R$^{17}$, R$^{18}$;
X is OH; A is —CH$_2$—; R$^3$ and R$^{16}$ are OCF$_3$; and R$^1$, R$^2$, R$^4$, R$^5$, R$^{10}$, R$^{11}$, R$^{14}$, R$^{15}$, R$^{17}$, R$^{18}$ and Y are H:

I-U

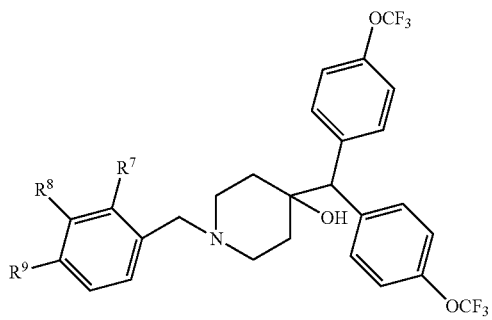

| Compd No. | R$^7$ | R$^8$ | R$^9$ |
|---|---|---|---|
| 583 | H | H | OCH$_2$CH$_2$OCH$_2$CH$_2$OCH$_3$ |
| 584 | H | H | OCH$_2$CH$_2$CH$_2$OCH$_3$ |
| 585 | H | H | 6-methoxy-pyrid-2-yloxy |
| 586 | H | methoxy | OCH$_2$CH$_2$OCH$_3$ |

TABLE 1-continued

| | | | |
|---|---|---|---|
| 587 | H | Cl | OCH₂CH₂OCH₃ |
| 588 | Cl | H | OCH₂CH₂OCH₃ | where
m, p, and q are 0; t and u are 1; r is 1, forming an N-oxide; R is phenyl substituted with $R^{14}$, $R^{15}$, $R^{16}$, $R^{17}$, $R^{18}$;
X is OH; A is —CH₂—; $R^3$ and $R^{16}$ are OCF₃; and $R^1$, $R^2$, $R^4$, $R^5$, $R^{10}$, $R^{11}$, $R^{14}$, $R^{15}$, $R^{17}$, $R^{18}$ and Y are H:

I-V

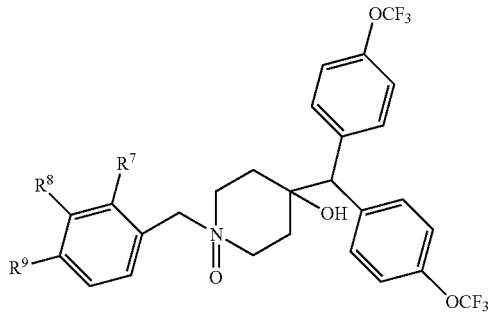

| Compd No. | $R^7$ | $R^8$ | $R^9$ |
|---|---|---|---|
| 589 | H | H | OCH₂CH₂OCH₂CH₂OCH₃ |
| 590 | H | H | OCH₂CH₂CH₂OCH3 |
| 591 | H | H | 6-methoxy-pyrid-2-yloxy |
| 592 | H | methoxy | OCH₂CH₂OCH₃ |
| 593 | H | Cl | OCH₂CH₂OCH₃ |
| 594 | H | Cl | OCH₂CH₂OCH₃ |

The following table sets forth physical characterizing data for compounds of formula I:

TABLE 2

| Cmpd No. | Emperical Formula | Physical State/Melting Point (° C.) |
|---|---|---|
| 1 | C₂₉H₂₇Cl₂N₃O₂ | Solid Foam |
| 2 | C₃₁H₂₇F₆N₃O₃ | Solid |
| 3 | C₃₀H₂₆Cl₂F₃N₃O₂ | — |
| 4 | C₂₉H₂₅Cl₂F₂N₃O₂ | Solid Foam |
| 5 | C₃₂H₃₂F₃N₃O₄ | Solid |
| 6 | C₂₉H₂₅Cl₄N₃O₂ | Solid Foam |
| 7 | C₃₀H₂₇ClF₃N₃O₂ | Solid |
| 8 | C₂₉H₂₇F₂N₃O₂ | — |
| 9 | C₃₀H₂₆Cl₂F₃N₃O₂ | — |
| 10 | C₂₉H₂₅F₄N₃O₂ | — |
| 11 | C₃₀H₂₆F₅N₃O₂ | — |
| 12 | C₃₀H₂₇F₄N₃O₂ | Solid |
| 13 | C₃₀H₂₆Cl₂F₃N₃O₂ | Solid |
| 14 | C₃₀H₂₇ClF₃N₃O₂ | Solid |
| 15 | C₃₀H₂₆Cl₂F₃N₃O₂ | — |
| 16 | C₃₁H₂₇F₆N₃O₂ | — |
| 17 | C₃₀H₂₆F₅N₃O₂ | Oil |
| 18 | C₃₀H₂₇ClF₃N₃O₂ | Solid |
| 19 | C₃₁H₂₇F₆N₃O₄ | Solid, 68-79 |
| 20 | C₃₁H₂₇F₆N₃O₃ | Solid, 59-65 |
| 21 | C₃₂H₂₈F₆N₂O₄ | — |
| 22 | C₃₂H₂₈F₆N₂O₂ | Solid |
| 23 | C₂₈H₂₉Cl₂N₅O | — |
| 24 | C₂₈H29Cl₂N5O | Solid |
| 25 | C₃₀H₂₉F₆N₅O₃ | Solid/Solid Foam |
| 26 | C₂₈H₂₇Cl₄N₅O | Solid Foam |
| 27 | C₃₀H₂₉F₆N₅O | Solid Foam |
| 28 | C₃₀H₃₀F₆N₂O₄ | Liquid |
| 29 | C₃₁H₃₂F₆N₂O₅ | Solid, 82-85 |
| 30 | C₃₃H₂₇F₉N₂O₄ | — |
| 91 | C₃₀H₃₁F₆NO₅ | Solid, 52-57 |
| 92 | C₃₀H₃₁F₆NO₃ | Solid, 65-70 |
| 93 | C₂₉H₂₇F₆N₅O₄ | Solid |
| 111 | C₃₂H₂₈F₆N₂O₃ | Solid |
| 112 | C₃₁H₂₇F₆N₃O₅ | Solid, 198-202 |
| 113 | C₃₀H₂₉F₆N₅O₂ | — |
| 114 | C₃₀H₂₉F₆N₅O₄ | Solid |
| 115 | C₂₉H₂₅Cl₂F₂N₃O₃ | Solid Foam |
| 116 | C₃₁H₂₇F₆N₃O₄ | Solid, 213-215 |
| 117 | C₃₂H₂₈F₆N₂O₅ | Solid |
| 118 | C₃₀H₃₀F₆N₂O₅ | Solid, 82-184 |
| 119 | C₃₁H₃₂F₆N₂O₆ | Solid, 149-162 |
| 120 | C₃₁H₂₇F₆N₃O₃ | Solid |
| 121 | C₃₀H₃₁F₆NO₄ | Solid, 151-154 |
| 122 | C₂₉H₂₇F₆N₅O₅ | Solid, 208-211 |
| 123 | C₃₀H₃₁F₆NO₆ | Solid, 219-221 |
| 192 | C₃₁H₂₆F₇N₃O₃ | Solid |
| 193 | C₃₂H₂₇F₇N₂O | Solid |
| 194 | C₃₁H₂₆F₇N₃O | Solid |
| 195 | C₃₅H₃₁ClF₆N₂O₃ | Solid |
| 255 | C₃₂H₂₉F₆N₃O₄ | Solid |
| 256 | C₃₂H₂₉F₃N₂O₄ | Solid Foam, 54-57 |
| 257 | C₃₅H₃₇F₃N₂O₃ | Solid Foam, 71-75 |
| 258 | C₃₃H₃₆F₆N₂O₆ | Liquid |
| 259 | C₃₁H₃₂F₆N₂O₅ | Liquid |
| 260 | C₃₂H₃₁F₃N₂O₄ | Solid Foam, 54-56 |
| 261 | C₃₁H₂₈BrF₃N₂O₃ | Solid Foam, 52-54 |
| 262 | C₃₂H₃₁F₃N₂O₃ | Semi-Solid, 54-57 |
| 263 | C₃₀H₂₉F₆NO₅ | Oil/Solid, 55-65 |
| 264 | C₃₀H₂₉F₆NO₃ | Yellow Amorphous Solid |
| 265 | C₃₂H₂₈F₆N₂O₃ | Solid Foam, 55-58 |
| 266 | C₃₁H₃₂F₆N₂O₅ | Liquid |
| 267 | C₃₀H₂₈Cl₂N₂O₂ | Solid Foam 68-71 |
| 268 | C₃₁H₂₈F₄N₂O₃ | Solid Foam, 60-63 |
| 269 | C₃₂H₂₉F₅N₂O₄ | Solid Foam, 54-56 |
| 270 | C₂₈H₂₆F₆N₂O₂ | Solid |
| 271 | C₃₃H₃₀F₆N₂O₄ | Solid |

TABLE 2-continued

Physical Characteristics

| Cmpd No. | Emperical Formula | Physical State/Melting Point (° C.) |
|---|---|---|
| 272 | $C_{33}H_{30}F_6N_2O_4$ | Solid |
| 273 | $C_{32}H_{35}F_6NO_5$ | Oil |
| 274 | $C_{32}H_{29}F_6N_3O_5$ | Solid |
| 275 | $C_{30}H_{27}F_6N_3O_4$ | Solid |
| 276 | $C_{33}H_{30}F_6N_2O_4$ | Solid |
| 277 | $C_{29}H_{27}ClF_6N_2O_4$ | Liquid |
| 278 | $C_{34}H_{30}ClF_6NO_4$ | Solid Foam, 67-70 |
| 279 | $C_{31}H_{31}F_6NO_6$ | Solid |
| 280 | $C_{33}H_{35}F_6NO_5$ | Solid, 63-68 |
| 281 | $C_{33}H_{27}F_6N_3O_4$ | Solid |
| 282 | $C_{33}H_{30}F_6N_2O_4$ | Solid Foam, 53-56 |
| 283 | $C_{33}H_{27}F_6N_3O_4$ | Solid |
| 284 | $C_{42}H_{46}F_3N_3O_4$ | Oil |
| 285 | $C_{29}H_{28}F_6N_2O_5$ | Solid, 83-92 |
| 286 | $C_{33}H_{28}ClF_6NO_4$ | Syrup |
| 287 | $C_{33}H_{33}F_3N_2O_4$ | Solid Foam, 50-53 |
| 288 | $C_{31}H_{29}F_3N_2O_3$ | Solid Foam, 49-53 |
| 289 | $C_{36}H_{32}ClF_6NO_5$ | Solid Foam, 58-64 |
| 290 | $C_{33}H_{28}ClF_6NO_4$ | Syrup |
| 291 | $C_{31}H_{31}F_6NO_4$ | Solid |
| 292 | $C_{31}H_{31}F_6NO_5$ | Solid, 68-75 |
| 293 | $C_{30}H_{27}Cl_2F_6NO_4$ | Oil |
| 294 | $C_{35}H_{34}F_6N_2O_6$ | Glass |
| 295 | $C_{34}H_{33}F_3N_2O_5$ | Solid Foam, 52-56 |
| 296 | $C_{30}H_{27}F_6N_3O_4$ | Liquid |
| 297 | $C_{33}H_{28}ClF_6NO_4$ | Solid, 45-47 |
| 298 | $C_{31}H_{30}F_6N_2O_5$ | Semi Solid |
| 299 | $C_{31}H_{31}F_6NO_2$ | Solid |
| 300 | $C_{31}H_{32}F_6N_2O_5$ | |
| 301 | $C_{30}H_{27}F_9N_2O_4$ | Oil |
| 302 | $C_{27}H_{25}F_6NO_2$ | Solid |
| 303 | $C_{30}H_{31}F_6NO_2$ | Solid |
| 304 | $C_{34}H_{31}F_6NO_4$ | Solid |
| 305 | $C_{38}H_{42}F_6N_2O_4$ | Syrup |
| 306 | $C_{35}H_{29}F_{12}N_3O_4$ | Solid |
| 307 | $C_{31}H_{26}ClF_6N_3O_2$ | Solid |
| 308 | $C_{30}H_{31}F_6NO_5$ | Glass |
| 309 | $C_{32}H_{28}F_6N_2O_3$ | Solid |
| 310 | $C_{31}H_{32}F_6N_2O_5$ | Oil |
| 311 | $C_{32}H_{34}F_6N_2O_5$ | |
| 312 | $C_{30}H_{29}F_7N_2O_4$ | Oil |
| 313 | $C_{31}H_{32}F_6N_2O_3$ | Solid |
| 314 | $C_{31}H_{28}ClF_3N_2O_3$ | Solid, 61-85/Solid Foam, 65-95 |
| 315 | $C_{31}H_{31}F_6NO_4$ | Solid |
| 316 | $C_{34}H_{31}F_6NO_2$ | Solid |
| 317 | $C_{32}H_{32}F_6N_2O_7$ | |
| 318 | $C_{30}H_{30}F_6N_2O_3$ | Solid |
| 319 | $C_{32}H_{32}F_6N_2O_3$ | Oil |
| 320 | $C_{33}H_{34}F_6N_2O_5$ | |
| 321 | $C_{33}H_{30}F_6N_2O_4$ | Solid |
| 322 | $C_{32}H_{27}ClF_6N_2O_4$ | Solid |
| 323 | $C_{35}H_{30}Cl_2F_6N_2O_5$ | |
| 324 | $C_{34}H_{29}ClF_6N_2O_5$ | |
| 325 | $C_{30}H_{27}ClF_3N_3O_3$ | Solid, 75-81 |
| 326 | $C_{32}H_{34}F_6N_2O_5$ | |
| 327 | $C_{32}H_{32}F_6N_2O_5$ | Solid |
| 328 | $C_{29}H_{30}ClF_3N_2O_3$ | Solid Foam, 54-57 |
| 329 | $C_{34}H_{36}F_6N_2O_5$ | |
| 330 | $C_{31}H_{31}F_6NO_3$ | Solid |
| 331 | $C_{27}H_{25}F_6NO_4$ | Solid |
| 335 | $C_{35}H_{37}F_3N_2O_4$ | Solid, 108-112 |
| 336 | $C_{33}H_{36}F_6N_2O_7$ | Solid, 137-142 |
| 337 | $C_{31}H_{32}F_6N_2O_6$ | Solid, 173-176 |
| 338 | $C_{32}H_{31}F_3N_2O_5$ | Solid, 98-104 |
| 339 | $C_{31}H_{28}BrF_3N_2O_4$ | Solid, 103-107 |
| 340 | $C_{32}H_{31}F_3N_2O_4$ | Solid, 85-90 |
| 341 | $C_{30}H_{29}F_6NO_6$ | Solid, 164-185 |
| 342 | $C_{30}H_{29}F_6NO_4$ | Yellow Solid |
| 343 | $C_{32}H_{28}F_6N_2O_4$ | Solid, 118-121 |
| 344 | $C_{31}H_{32}F_6N_2O_6$ | Solid, 165-174 |
| 345 | $C_{30}H_{28}Cl_2N_2O_3$ | Solid, 95-101 |
| 346 | $C_{31}H_{28}F_4N_2O_4$ | Solid, 94-96 |
| 347 | $C_{32}H_{29}F_5N_2O_5$ | Solid, 98-118 |
| 349 | $C_{33}H_{30}F_6N_2O_5$ | Solid |
| 350 | $C_{33}H_{30}F_6N_2O_5$ | Solid |
| 351 | $C_{32}H_{35}F_6NO_6$ | Solid |
| 353 | $C_{30}H_{27}F_6N_3O_5$ | Solid, 136-140 |
| 354 | $C_{33}H_{30}F_6N_2O_5$ | Solid |
| 355 | $C_{29}H_{27}ClF_6N_2O_5$ | Solid, 181-184 |
| 357 | $C_{31}H_{31}F_6NO_7$ | Solid |
| 358 | $C_{33}H_{35}F_6NO_6$ | Solid, 210-212 |
| 359 | $C_{33}H_{27}F_6N_3O_5$ | Solid |
| 370 | $C_{31}H_{31}F_6NO_6$ | Solid, 212-214 |
| 371 | $C_{30}H_{27}Cl_2F_6NO_5$ | Oil |
| 372 | $C_{35}H_{34}F_6N_2O_7$ | Solid |
| 375 | $C_{33}H_{28}ClF_6NO_5$ | Solid Foam, 70-74 |
| 378 | $C_{30}H_{27}F_9N_2O_5$ | Solid, 192-194 |
| 380 | $C_{30}H_{31}F_6NO_3$ | Solid |
| 381 | $C_{34}H_{31}F_6NO_5$ | Solid |
| 383 | $C_{31}H_{31}F_6NO_3$ | Solid |
| 384 | $C_{31}H_{26}ClF_6N_3O_3$ | Solid |
| 385 | $C_{30}H_{31}F_6NO_6$ | Solid |
| 387 | $C_{31}H_{32}F_6N_2O_6$ | Oil |
| 389 | $C_{30}H_{29}F_7N_2O_5$ | Solid, 193-195 |
| 390 | $C_{31}H_{32}F_6N_2O_4$ | Solid |
| 391 | $C_{31}H_{28}ClF_3N_2O_4$ | Solid, 62-66 |
| 392 | $C_{31}H_{31}F_6NO_5$ | Solid |
| 393 | $C_{34}H_{31}F_6NO_3$ | Solid |
| 395 | $C_{30}H_{30}F_6N_2O_4$ | Solid |
| 396 | $C_{32}H_{32}F_6N_2O_4$ | Solid |
| 399 | $C_{32}H_{27}ClF_6N_2O_5$ | Solid, 200-203 |
| 402 | $C_{30}H_{27}ClF_3N_3O_4$ | Solid, 84-88 |
| 404 | $C_{32}H_{32}F_6N_2O_6$ | Solid |
| 405 | $C_{29}H_{30}ClF_3N_2O_4$ | Solid, 77-82 |
| 407 | $C_{31}H_{31}F_6NO_4$ | Solid |
| 409 | $C_{35}H_{29}F_{12}N_3O_5$ | Solid |
| 410 | $C_{30}H_{29}F_6N_3O_6$ | Solid, 210-213 |
| 411 | $C_{32}H_{27}ClF_6N_2O_4$ | Solid, 204-207 |
| 412 | $C_{31}H_{26}ClF_6N_3O_5$ | Solid, 210-212 |
| 413 | $C_{32}H_{29}F_6N_3O_5$ | Solid |
| 416 | $C_{30}H_{29}F_6N_5O_4$ | Solid |
| 417 | $C_{30}H_{30}F_6N_2O_5$ | Solid |
| 418 | $C_{28}H_{25}F_6NO_5$ | Solid |
| 419 | $C_{31}H_{32}F_6N_2O_6$ | Solid |
| 421 | $C_{32}H_{28}F_6N_2O_6$ | Solid |
| 422 | $C_{31}H_{27}F_6N_3O_6$ | Solid |
| 423 | $C_{31}H_{32}F_6N_2O_7$ | Solid |
| 424 | $C_{30}H_{30}F_6N_2O_6$ | Solid |
| 425 | $C_{31}H_{26}ClF_6N_3O_6$ | Solid |
| 426 | $C_{30}H_{29}F_6N_5O_5$ | Solid |
| 430 | $C_{32}H_{27}F_7N_2O_5$ | Solid |
| 431 | $C_{32}H_{26}F_6N_2O_5$ | Solid |
| 432 | $C_{31}H_{25}F_6N_3O_3$ | Solid |
| 433 | $C_{31}H_{27}Cl_2F_3N_2O_3$ | Solid Foam, 69-71 |
| 434 | $C_{29}H_{27}F_2N_3O_2$ | Solid Foam |
| 435 | $C_{32}H_{30}ClF_3N_2O_3$ | Solid Foam, 60-64 |
| 436 | $C_{32}H_{30}ClF_3N_2O_3$ | Solid Foam, 59-62 |
| 437 | $C_{31}H_{28}ClF_3N_2O_3$ | Solid Foam, 59-62 |
| 438 | $C_{31}H_{27}Cl_2F_3N_2O_3$ | Solid Foam, 59-63 |
| 439 | $C_{31}H_{28}ClF_3N_2O_3$ | Solid Foam, 55-58 |
| 440 | $C_{34}H_{34}F_3N_3O_4$ | Solid Foam, 53-56 |
| 441 | $C_{31}H_{27}Cl_2F_3N_2O_3$ | Solid Foam, 60-64 |
| 442 | $C_{31}H_{27}Cl_2F_3N_2O_3$ | Solid Foam, 58-62 |
| 443 | $C_{31}H_{27}Cl_2F_3N_2O_3$ | Solid Foam, 55-59 |
| 444 | $C_{29}H_{29}Cl_2F_3N_2O_3$ | Solid Foam, 55-59 |
| 445 | $C_{31}H_{27}ClF_4N_2O_3$ | Solid Foam, 60-63 |
| 446 | $C_{32}H_{26}F_4N_2O_6$ | Oil/Solid Foam, 60-64 |
| 447 | $C_{33}H_{30}F_6N_2O_5$ | Solid |
| 448 | $C_{32}H_{29}F_6N_3O_2$ | Solid |
| 449 | $C_{32}H_{34}F_6N_4O$ | Solid |
| 450 | $C_{32}H_{34}F_6N_2O$ | Solid |
| 451 | $C_{34}H_{32}F_6N_4O_2$ | Solid |
| 452 | $C_{34}H_{31}F_6N_3O_3$ | Solid |
| 453 | $C_{29}H_{29}Cl_2F_3N_2O_4$ | Solid, 83-86 |

TABLE 2-continued

Physical Characteristics

| Cmpd No. | Emperical Formula | Physical State/Melting Point (° C.) |
|---|---|---|
| 454 | $C_{31}H_{27}Cl_2F_3N_2O_4$ | Solid, 101-105 |
| 455 | $C_{31}H_{27}Cl_2F_3N_2O_4$ | Solid, 100-104 |
| 456 | $C_{31}H_{27}Cl_2F_3N_2O_4$ | Solid, 79-82 |
| 457 | $C_{31}H_{27}Cl_2F_3N_2O_4$ | Solid, 98-102 |
| 458 | $C_{31}H_{28}ClF_3N_2O_4$ | Solid, 85-89 |
| 459 | $C_{31}H_{28}ClF_3N_2O_4$ | Solid, 98-102 |
| 460 | $C_{31}H_{27}Cl_2F_3N_2O_4$ | Solid Foam, 76-80 |
| 461 | $C_{32}H_{30}ClF_3N_2O_4$ | Solid, 145-149 |
| 462 | $C_{32}H_{30}ClF_3N_2O_4$ | Solid, 89-92 |
| 463 | $C_{31}H_{27}ClF_4N_2O_4$ | Solid, 84-87 |
| 464 | $C_{32}H_{26}F_4N_2O_7$ | Solid Foam, 72-77 |
| 465 | $C_{33}H_{30}F_6N_2O_6$ | Solid |
| 466 | $C_{34}H_{32}F_6N_4O_3$ | Solid |
| 467 | $C_{32}H_{32}F_6N_4O_2$ | Solid |
| 468 | $C_{34}H_{31}F_6N_3O_4$ | Solid |
| 470 | $C_{29}H_{28}ClF_6NO_5$ | Solid Foam, 42-45 |
| 471 | $C_{29}H_{28}ClF_6NO_5$ | Solid Foam, 42-44 |
| 472 | $C_{29}H_{28}ClF_6NO_5$ | Solid Foam, 43-45 |
| 473 | $C_{29}H_{28}ClF_6NO_4$ | Syrup |
| 474 | $C_{28}H_{26}ClF_6NO_3$ | Syrup |
| 475 | $C_{28}H_{26}ClF_6NO_4$ | Syrup |
| 476 | $C_{30}H_{30}ClF_6NO_4$ | Oil |
| 477 | $C_{28}H_{26}BrF_6NO_4$ | Syrup |
| 478 | $C_{28}H_{26}ClF_6NO_5$ | Solid, 54-58 |
| 479 | $C_{28}H_{26}ClF_6NO_4$ | Solid, 55-60 |
| 480 | $C_{30}H_{30}ClF_6NO_5$ | Semi-Solid |
| 481 | $C_{29}H_{28}ClF_6NO_5$ | Solid, 57-61 |
| 482 | $C_{28}H_{26}BrF_6NO_5$ | Solid, 60-65 |
| 483 | $C_{30}H_{31}F_6N_2O_5 \cdot C_3H_7O_4S$ | Solid, 120-128 |
| 484 | $C_{30}H_{31}F_6N_2O_5 \cdot C_5H_9O_3$ | Solid, 74-80 |
| 485 | $C_{31}H_{27}ClF_6N_3O_5 \cdot C_8H_{15}O_2$ | Solid, 190-194 |
| 486 | $C_{30}H_{31}F_6N_2O_5 \cdot C_8H_{15}O_2$ | Solid, 53-65 |
| 487 | $C_{30}H_{31}F_6N_2O_5 \cdot C_4F_9O_3S$ | Solid, 85-94 |
| 488 | $C_{31}H_{27}ClF_6N_3O_3 \cdot C_6H_7O_7$ | Solid, 132-142 |
| 489 | $C_{30}H_{30}F_6N_3O_6 \cdot C_6H_7O_7$ | Solid, 113-123 |
| 490 | $C_{30}H_{31}F_6N_2O_5 \cdot C_{10}H_{15}O_4S$ | Solid, 123-131 |
| 491 | $C_{30}H_{31}F_6N_2O_5 \cdot C_2H_5O_3S$ | Solid, 188-192 |
| 492 | $C_{31}H_{27}ClF_6N_3O_5 \cdot C_6H_7O_7$ | Solid, 135-144 |
| 493 | $C_{30}H_{31}F_6N_2O_5 \cdot C_7H_{11}O_2$ | Solid, 78-88 |
| 494 | $C_{30}H_{31}F_6N_2O_5 \cdot C_6H_7O_7$ | Solid, 114-119 |
| 495 | $C_{30}H_{31}F_6N_2O_5 \cdot C_8F_{17}O_3S$ | Solid, 74-84 |
| 496 | $C_{32}H_{29}F_6N_2O_5 \cdot C_8F_{17}O_3S$ | Solid, 96-101 |
| 497 | $C_{32}H_{29}F_6N_2O_5 \cdot Cl$ | Solid, 140-143 |
| 498 | $C_{32}H_{29}F_6N_2O_5 \cdot C_{10}H_{15}O_4S$ | Solid, 122-136 |
| 499 | $C_{32}H_{29}F_6N_2O_5 \cdot C_8H_{15}O_2$ | Solid, 55-65 |
| 500 | $C_{32}H_{29}F_6N_2O_5 \cdot C_3H_7O_4S$ | Solid, 111-128 |
| 501 | $C_{29}H_{29}ClF_6N_2O_5 \cdot C_6H_7O_7$ | Solid, 96-101 |
| 502 | $C_{32}H_{29}F_6N_2O_5 \cdot C_7H_{11}O_2$ | Solid, 80-85 |
| 503 | $C_{32}H_{29}F_6N_2O_5 \cdot C_5H_9O_3$ | Solid, 75-81 |
| 504 | $C_{32}H_{29}F_6N_2O_5 \cdot C_6H_7O_7$ | Solid, 195-197 |
| 505 | $C_{32}H_{29}F_6N_2O_5 \cdot C_{10}H_{15}O_4S$ | Solid, 121-132 |
| 506 | $C_{32}H_{29}F_6N_2O_5 \cdot C_2H_5O_3S$ | Solid, 168-184 |
| 507 | $C_{30}H_{31}F_6N_2O_5 \cdot C_{10}H_{15}O_4S$ | Solid, 118-119 |
| 508 | $C_{32}H_{29}F_6N_2O_5 \cdot C_4F_9O_3S$ | Solid, 94-104 |
| 509 | $C_{32}H_{29}F_6N_2O_5 \cdot C_{10}H_{17}O_2$ | Solid, 43-58 |
| 510 | $C_{32}H_{29}F_6N_2O_5 \cdot C_2H_3O_3$ | Solid, 87-103 |
| 511 | $C_{32}H_{29}F_6N_2O_5 \cdot C_{11}H_{15}O_2$ | Solid, 100-125 |
| 512 | $C_{32}H_{29}F_6N_2O_5 \cdot C_5H_7O_4$ | Solid, 80-85 |
| 513 | $C_{32}H_{29}F_6N_2O_5 \cdot C_{18}H_{33}O_2$ | Liquid |
| 514 | $C_{32}H_{29}F_6N_2O_5 \cdot C_7H_{11}O_4$ | Solid, 78-88 |
| 515 | $C_{32}H_{29}F_6N_2O_5 \cdot C_{18}H_{29}O_3S$ | Solid, 85-97 |
| 516 | $C_{32}H_{29}F_6N_2O_5 \cdot C_6H_9O_4$ | Solid, 78-90 |
| 517 | $C_{32}H_{29}F_6N_2O_5 \cdot C_8H_{15}O_2$ | Solid, 44-65 |
| 518 | $C_{31}H_{27}ClF_6N_3O_3 \cdot C_2H_5O_3S$ | Solid |
| 519 | $C_{31}H_{27}ClF_6N_3O_3 \cdot C_9H_9ClF_3O_2$ | Solid, 112-117 |
| 520 | $C_{31}H_{27}ClF_6N_3O_3 \cdot C_8F_{17}O_3S$ | Solid |
| 521 | $C_{42}H_{46}F_6N_3O_8 \cdot Cl$ | Solid, |
| 522 | $C_{32}H_{29}F_6N_2O_4 \cdot ClH$ | Solid, 78-82 |

Candidate insecticides were evaluated for activity against the tobacco budworm (*Heliothis virescens* [Fabricius]) in a surface-treated diet test.

In this test one mL of molten (65-70° C.) wheat germ-based artificial diet was pipetted into each well of a four by six (24 well) multi-well plate (ID# 430345-15.5 mm dia.×17.6 mm deep; Corning Costar Corp., One Alewife Center, Cambridge, Mass. 02140). The diet was allowed to cool to ambient temperature before treatment with candidate insecticide.

For a determination of insecticidal activity, solutions of the candidate insecticides were prepared for testing using a Packard 204DT Multiprobe® Robotic System (Packard Instrument Company, 800 Research Parkway, Meriden, Conn. 06450), in which the robot first diluted a standard 50 millimolar DMSO solution of candidate insecticide with a 1:1 water/acetone solution (V/V) in a ratio of 1:7 stock solution to water/acetone. The robot subsequently pipetted 40 microliters of the so-prepared solution onto the surface of the diet in each of three wells in the 24 multi-well plate. The process was repeated with solutions of seven other candidate insecticides. Once treated, the contents of the multi-well plate were allowed to dry, leaving 0.25 millimoles of candidate insecticide on the surface of the diet, or a concentration of 0.25 millimolar. Appropriate untreated controls containing only DMSO on the diet surface were also included in this test.

For evaluations of the insecticidal activity of a candidate insecticide at varying rates of application, the test was established as described above using sub-multiples of the standard 50 millimolar DMSO solution of candidate insecticide. For example, the standard 50 millimolar solution was diluted by the robot with DMSO to give 5, 0.5, 0.05, 0.005, 0.0005 millimolar, or more dilute solutions of the candidate insecticide. In these evaluations there were six replicates of each rate of application placed on the surface of the diet in the 24 multi-well plate, for a total of four rates of application of candidate insecticide in each plate.

In each well of the test plate was placed one second instar tobacco budworm larvea, each weighing approximately five milligrams. After the larvae were placed in each well, the plate was sealed with clear polyfilm adhesive tape. The tape over each well was perforated to ensure an adequate air supply. The plates were then held in a growth chamber at 25° C. and 60% relative humidity for five days (light 14 hours/day).

After the five-day exposure period insecticidal activity for each rate of application of candidate insecticide was assessed as percent inhibition of insect weight relative to the weight of insects from untreated controls, and percent mortality when compared to the total number of insects infested.

Insecticidal activity data at selected rates of application from this test are provided in Table 3. The test compounds of formula I are identified by numbers that correspond to those in Table 1.

TABLE 3

Insecticidal Activity of Test Compounds Applied to the Surface of the Diet of Tobacco Budworm

| | Cmpd. No | | | | | | | | | |
|---|---|---|---|---|---|---|---|---|---|---|
| | 1 | 2 | 3 | 4 | 5 | 6 | 7 | 8 | 9 | 10 |
| Percent Mortality | 0 | 100 | 100 | 100 | 0 | 83 | 100 | 0 | 100 | 0 |
| Percent Growth Inhibition | 57 | 100 | 100 | 100 | 97 | 100 | 100 | 41 | 100 | 50 |

| | Cmpd. No | | | | | | | | | |
|---|---|---|---|---|---|---|---|---|---|---|
| | 11 | 12 | 13 | 14 | 15 | 16 | 17 | 18 | 19 | 20 |
| Percent Mortality | 33 | 0 | 100 | 100 | 100 | 100 | 83 | 100 | 100 | 100 |
| Percent Growth Inhibition | 100 | 100 | 100 | 100 | 100 | 100 | 100 | 100 | 100 | 100 |

| | Cmpd. No | | | | | | | | | |
|---|---|---|---|---|---|---|---|---|---|---|
| | 21 | 22 | 23 | 24 | 25 | 26 | 27 | 28 | 29 | 30 |
| Percent Mortality | 100 | 100 | 100 | 0 | 100 | 100 | 100 | 100 | 100 | 100 |
| Percent Growth Inhibition | 100 | 100 | 100 | 98 | 100 | 100 | 100 | 100 | 100 | 100 |

| | Cmpd. No | | | | | | | | | |
|---|---|---|---|---|---|---|---|---|---|---|
| | 91 | 92 | 93 | 111 | 112 | 113 | 114 | 115 | 116 | 117 |
| Percent Mortality | 100 | 100 | 100 | 100 | 100 | 100 | 100 | 50 | 100 | 100 |
| Percent Growth Inhibition | 100 | 100 | 100 | 100 | 100 | 100 | 100 | 100 | 100 | 100 |

| | Cmpd. No | | | | | | | | | |
|---|---|---|---|---|---|---|---|---|---|---|
| | 118 | 119 | 120 | 121 | 122 | 123 | 192 | 193 | 194 | 195 |
| Percent Mortality | 100 | 100 | 100 | 100 | 100 | 100 | 100 | 100 | 100 | 100 |
| Percent Growth Inhibition | 100 | 100 | 100 | 100 | 100 | 100 | 100 | 100 | 100 | 100 |

| | Cmpd. No | | | | | | | | | |
|---|---|---|---|---|---|---|---|---|---|---|
| | 255 | 256 | 257 | 258 | 259 | 260 | 261 | 262 | 263 | 264 |
| Percent Mortality | 100 | 17 | 100 | 100 | 100 | 100 | 100 | 100 | 100 | 33 |
| Percent Growth Inhibition | 100 | 100 | 100 | 100 | 100 | 100 | 100 | 100 | 100 | 100 |

| | Cmpd. No | | | | | | | | | |
|---|---|---|---|---|---|---|---|---|---|---|
| | 265 | 266 | 267 | 268 | 269 | 270 | 271 | 272 | 273 | 274 |
| Percent Mortality | 100 | 100 | 100 | 100 | 100 | 100 | 100 | 100 | 100 | 100 |
| Percent Growth Inhibition | 100 | 100 | 100 | 100 | 100 | 100 | 100 | 100 | 100 | 100 |

| | Cmpd. No | | | | | | | | | |
|---|---|---|---|---|---|---|---|---|---|---|
| | 275 | 276 | 277 | 278 | 279 | 280 | 281 | 282 | 283 | 284 |
| Percent Mortality | 100 | 100 | 100 | 100 | 83 | 100 | 100 | 100 | 100 | 17 |
| Percent Growth Inhibition | 100 | 100 | 100 | 100 | 100 | 100 | 100 | 100 | 100 | 100 |

| | Cmpd. No | | | | | | | | | |
|---|---|---|---|---|---|---|---|---|---|---|
| | 285 | 286 | 287 | 288 | 289 | 290 | 291 | 292 | 293 | 294 |
| Percent Mortality | 100 | 100 | 100 | 100 | 100 | 100 | 17 | 100 | 100 | 100 |
| Percent Growth Inhibition | 100 | 100 | 100 | 100 | 100 | 100 | 100 | 100 | 100 | 100 |

TABLE 3-continued

Insecticidal Activity of Test Compounds Applied to the Surface of the Diet of Tobacco Budworm

| | Cmpd. No | | | | | | | | |
|---|---|---|---|---|---|---|---|---|---|
| | 295 | 297 | 298 | 299 | 300 | 301 | 302 | 303 | 304 |
| Percent Mortality | 100 | 100 | 100 | 100 | 100 | 100 | 17 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 305 | 306 | 307 | 308 | 309 | 310 | 311 | 312 | 313 | 314 |
| Percent Mortality | 0 | 100 | 100 | 100 | 100 | 100 | 100 | 100 | 100 | 100 |
| Percent Growth Inhibition | 31 | 100 | 100 | 100 | 100 | 100 | 100 | 100 | 100 | 100 |

| | Cmpd. No | | | | | | | | |
|---|---|---|---|---|---|---|---|---|---|
| | 315 | 316 | 317 | 319 | 320 | 321 | 322 | 323 | 324 |
| Percent Mortality | 100 | 67 | 100 | 100 | 100 | 100 | 100 | 33 | 33 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 325 | 3256 | 327 | 328 | 329 | 330 | 331 | 335 | 336 | 337 |
| Percent Mortality | 100 | 100 | 100 | 100 | 67 | 100 | 50 | 100 | 100 | 100 |
| Percent Growth Inhibition | 100 | 100 | 100 | 100 | 100 | 100 | 100 | 100 | 100 | 100 |

| | Cmpd. No | | | | | | | | |
|---|---|---|---|---|---|---|---|---|---|
| | 338 | 339 | 340 | 341 | 342 | 343 | 344 | 345 | 346 | 347 |
| Percent Mortality | 100 | 100 | 100 | 100 | 100 | 100 | 100 | 100 | 100 | 100 |
| Percent Growth Inhibition | 100 | 100 | 100 | 100 | 100 | 100 | 100 | 100 | 100 | 100 |

| | Cmpd. No | | | | | | | | |
|---|---|---|---|---|---|---|---|---|---|
| | 349 | 350 | 351 | 353 | 354 | 355 | 357 | 358 | 359 | 370 |
| Percent Mortality | 100 | 100 | 100 | 100 | 100 | 100 | 0 | 100 | 100 | 100 |
| Percent Growth Inhibition | 100 | 100 | 100 | 100 | 100 | 100 | 100 | 100 | 100 | 100 |

| | Cmpd. No | | | | | | | | |
|---|---|---|---|---|---|---|---|---|---|
| | 371 | 372 | 375 | 378 | 380 | 381 | 383 | 384 | 385 | 387 |
| Percent Mortality | 100 | 100 | 100 | 100 | 100 | 100 | 100 | 100 | 100 | 100 |
| Percent Growth Inhibition | 100 | 100 | 100 | 100 | 100 | 100 | 100 | 100 | 100 | 100 |

| | Cmpd. No | | | | | | | |
|---|---|---|---|---|---|---|---|---|
| | 389 | 390 | 391 | 392 | 393 | 396 | 399 | 402 | 404 |
| Percent Mortality | 100 | 100 | 100 | 100 | 100 | 67 | 100 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 405 | 407 | 409 | 410 | 411 | 412 | 413 | 416 | 417 | 418 |
| Percent Mortality | 100 | 100 | 100 | 100 | 100 | 100 | 100 | 100 | 100 | 0 |
| Percent Growth Inhibition | 100 | 100 | 100 | 100 | 100 | 100 | 100 | 100 | 100 | 83 |

TABLE 3-continued

Insecticidal Activity of Test Compounds Applied to the Surface of the Diet of Tobacco Budworm

| | Cmpd. No | | | | | | | | |
|---|---|---|---|---|---|---|---|---|---|
| | 419 | 421 | 422 | 423 | 424 | 425 | 426 | 430 | 431 |
| Percent Mortality | 100 | 100 | 100 | 100 | 100 | 100 | 100 | 100 | 100 |
| Percent Growth Inhibition | 100 | 100 | 100 | 100 | 100 | 100 | 100 | 100 | 100 |

| | Cmpd. No | | | | | | | | |
|---|---|---|---|---|---|---|---|---|---|
| | 432 | 433 | 434 | 435 | 436 | 437 | 438 | 439 | 440 | 441 |
| Percent Mortality | 100 | 100 | 0 | 100 | 100 | 100 | 100 | 100 | 100 | 100 |
| Percent Growth Inhibition | 100 | 100 | 56 | 100 | 100 | 100 | 100 | 100 | 100 | 100 |

| | Cmpd. No | | | | | | | | |
|---|---|---|---|---|---|---|---|---|---|
| | 442 | 443 | 444 | 445 | 446 | 447 | 448 | 449 | 450 | 451 |
| Percent Mortality | 100 | 100 | 100 | 100 | 100 | 100 | 0 | 0 | 50 | 0 |
| Percent Growth Inhibition | 100 | 100 | 100 | 100 | 100 | 100 | 96 | 78 | 100 | 100 |

| | Cmpd. No | | | | | | | | |
|---|---|---|---|---|---|---|---|---|---|
| | 452 | 453 | 454 | 455 | 456 | 457 | 458 | 459 | 460 | 461 |
| Percent Mortality | 0 | 100 | 100 | 100 | 100 | 100 | 100 | 100 | 100 | 100 |
| Percent Growth Inhibition | 100 | 100 | 100 | 100 | 100 | 100 | 100 | 100 | 100 | 100 |

| | Cmpd. No | | | | | | | | |
|---|---|---|---|---|---|---|---|---|---|
| | 462 | 463 | 464 | 465 | 466 | 467 | 468 | 470 | 471 |
| Percent Mortality | 100 | 100 | 100 | 100 | 17 | 50 | 17 | 17 | 0 |
| Percent Growth Inhibition | 100 | 100 | 100 | 100 | 100 | 100 | 100 | 89 | 82 |

| | Cmpd. No | | | | | | | | |
|---|---|---|---|---|---|---|---|---|---|
| | 472 | 473 | 474 | 475 | 476 | 477 | 478 | 479 | 480 | 481 |
| Percent Mortality | 17 | 100 | 83 | 100 | 67 | 100 | 100 | 100 | 100 | 100 |
| Percent Growth Inhibition | 93 | 100 | 100 | 100 | 100 | 100 | 100 | 100 | 100 | 100 |

| | Cmpd. No | | | | | | | | |
|---|---|---|---|---|---|---|---|---|---|
| | 482 | 483 | 484 | 485 | 486 | 487 | 488 | 489 | 490 | 491 |
| Percent Mortality | 100 | 100 | 100 | 100 | 100 | 100 | 100 | 100 | 100 | 100 |
| Percent Growth Inhibition | 100 | 100 | 100 | 100 | 100 | 100 | 100 | 100 | 100 | 100 |

| | Cmpd. No | | | | | | | | |
|---|---|---|---|---|---|---|---|---|---|
| | 492 | 493 | 494 | 495 | 496 | 497 | 498 | 499 | 500 | 501 |
| Percent Mortality | 100 | 100 | 100 | 100 | 100 | 100 | 100 | 100 | 100 | 100 |
| Percent Growth Inhibition | 100 | 100 | 100 | 100 | 100 | 100 | 100 | 100 | 100 | 100 |

| | Cmpd. No | | | | | | | | |
|---|---|---|---|---|---|---|---|---|---|
| | 502 | 503 | 504 | 505 | 506 | 507 | 508 | 509 | 510 | 511 |
| Percent Mortality | 100 | 100 | 100 | 100 | 100 | 100 | 100 | 100 | 100 | 100 |
| Percent Growth Inhibition | 100 | 100 | 100 | 100 | 100 | 100 | 100 | 100 | 100 | 100 |

TABLE 3-continued

Insecticidal Activity of Test Compounds Applied to the
Surface of the Diet of Tobacco Budworm

| | Cmpd. No | | | | | | | | | | |
|---|---|---|---|---|---|---|---|---|---|---|---|
| | 512 | 513 | 514 | 515 | 516 | 517 | 518 | 519 | 520 | 521 | 522 |
| Percent Mortality | 100 | 100 | 100 | 100 | 100 | 100 | 100 | 100 | 100 | 50 | 100 |
| Percent Growth Inhibition | 100 | 100 | 100 | 100 | 100 | 100 | 100 | 100 | 100 | 100 | 100 |

These tests were conducted with 0.25 millimoles of candidate insecticide on the surface of the diet As set forth in the foregoing Table 3, most of the compounds therein provided 100% mortality and 100% growth inhibition of tobacco budworm.

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A compound of formula I:

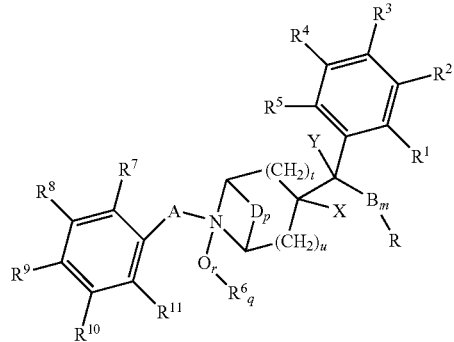

wherein m, q and p are 0; t and u are 1; A is —$CH_2$—; X is selected from halogen, hydroxyl or alkoxycarbonyl; Y is selected from hydrogen, halogen or hydroxyl; $R^1$, $R^2$, $R^3$ and $R^4$ are independently selected from hydrogen, halogen, alkyl, alkoxy, haloalkyl, haloalkoxy, —$CH_2(OH)$ $CH_3$, —CH=$NOC_2H_5$, 1,3-dioxolan-2-yl, or $R^2$ and $R^3$ taken together with —$OCF_2O$—; $R^5$ is hydrogen; $R^7$, $R^{10}$ and $R^{11}$ are hydrogen; $R^8$ is selected from hydrogen, halogen, alkyl or alkoxy; $R^9$ is selected from alkoxy, alkoxyalkoxy, alkoxyalkoxyalkoxy, cyclopropylmethoxy, 2-halophenoxy, 3-halophenoxy, 4-halophenoxy, pyrimidin-2-yl, pyrid-2-yl, 3-halo-pyrid-2-yl, 3-alkyl-pyrid-2-yloxy, 4-alkyl-pyrid-2-yloxy, 5-alkyl-pyrid-2-yloxy, 6-alkyl-pyrid-2-yloxy, 3-halo-pyrid-2-yloxy, 3-trihaloalkyl-pryid-2-yloxy, 3-cyano-pyrid-2-yloxy, 5-cyano-pyrid-2-yloxy, 6-dialkoxyalkyl-pyrid-2-yloxy, pyrid-2-yloxy, $CO_2CH(CH_3)_2$, —CH=$NOCH_3$, —CH=$NOC_2H_5$, —CH=$NOCH_2CF_3$, —CH=$NOCH_2CH$=$CH_2$, —CH=$NOCH_2CN$, —CH=$NOCH(CH_3)_2$, —CH=$NOCH_2C$≡CH, —CH=$NOCH_2CH_2F$, —CH=$NOCH_2CH_2OCH_3$, —CH=$NOCH_2OC_2H_5$, —CH=$NOCH_2CH_2OCH_2CH_2OCH_3$, —$NHCO_2CH_3$, —$NHCO_2C_2H_5$, —$NHCO_2CH(CH_3)_2$, —$NHCO_2$ $CH_2$-c-$C_3H_5$, —CH(OH)$C_6H_5$-p-Cl, —OC(=O) $NHCH_3$, —OC(=O)$NHC_2H_5$, —OC(=O)NHCH $(CH_3)_2$, —NHC($SCH_3$)=NCN, pyrimidin-2-yloxy, 6-halo-pyridazin-3-yloxy, 6-alkoxy-pyridazin-3-yloxy, 6-alkyl-pyridazin-3-yloxy, 2-alkyl-2H-tetrazol-5-yl, 1,3-dioxan-2-yl or 5,5-dialkyl-1,3-dioxan-2-yl; and R is phenyl substituted with $R^{14}$, $R^{15}$, $R^{16}$, $R^{17}$, and $R^{18}$,

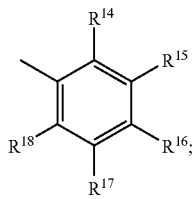

where
$R^{14}$, $R^{15}$, $R^{16}$ and $R^{17}$ are independently selected from halogen, haloalkyl, haloalkoxy or $R^{15}$ and $R^{16}$ taken together with —$OCF_2O$—; and $R^{18}$ is hydrogen and agriculturally-acceptable salts thereof.

2. The compound of claim 1, wherein X is selected from halogen, —$CO_2C_2H_5$ or hydroxyl; and $R^9$ is selected from —$OC_2H_5$, —$OC_3H_7$, —$OCH(CH_3)_2$, —$OCH_2CH_2OCH_3$, —$OCH_2CH_2CH_2OCH_3$, cyclopropylmethoxy, 2-chlorophenoxy, 3-chlorophenoxy, 4-chlorophenoxy, pyrimidin-2-yl, pyrid-2-yl, 3-chloro-pyrid-2-yl, 3-methyl-pyrid-2-yloxy, 4-methyl-pyrid-2-yloxy, 5-methyl-pyrid-2-yloxy, 6-methyl-pyrid-2-yloxy, 3-chloro-pyrid-2-yloxy, 3-trifluoromethyl-pryid-2-yloxy, 3-cyano-pyrid-2-yloxy, 5-cyano-pyrid-2-yloxy, 6-dimethoxymethyl-pyrid-2-yloxy, pyrid-2-yloxy, —$CO_2CH(CH_3)_2$, —CH=$NOCH_3$, —CH=$NOC_2H_5$, —CH=$NOCH_2CF_3$, —CH=$NOCH_2CH$=$CH_2$, —CH=$NOCH_2CN$, —CH=$NOCH(CH_3)_2$, —CH=$NOCH_2C$≡CH, —CH=$NOCH_2CH_2F$, —CH=$NOCH_2CH_2OCH_3$, —CH=$NOCH_2OC_2H_5$, —CH=$NOCH_2CH_2OCH_2CH_2OCH_3$, —$NHCO_2CH_3$, —$NHCO_2C_2H_5$, —$NHCO_2CH(CH_3)_2$, —$NHCO_2CH_2$-c-$C_3H_5$, —CH(OH)$C_6H_5$-p-Cl, —OC(=O)$NHCH_3$, —OC(=O)$NHC_2H_5$, —OC(=O)NHCH($CH_3$)$_2$, —NHC($SCH_3$)=NCN, pyrimidin-2-yloxy, 6-chloro-pyridazin-3-yloxy, 6-methoxy-pyridazin-3-yloxy, 6-methyl-pyridazin-3-yloxy, 2-methyl-2H-tetrazol-5-yl, 2-ethyl-2H-tetrazol-5-yl, 1,3-dioxan-2-yl or 5,5-dimethyl-1,3-dioxan-2-yl.

3. The compound of claim 2, wherein X is selected from fluorine, —$CO_2C_2H_5$ or hydroxyl; Y is selected from hydrogen, fluorine, chlorine or hydroxyl; $R^1$, $R^2$, $R^3$ and $R^4$ are independently selected from hydrogen, halogen, alkyl, tert-butyl, methoxy, trifluoromethyl, difluoromethoxy, trifluoromethoxy, —$OCF_2CHFCF_3$, —$CH_2(OH)CH_3$, —CH=$NOC_2H_5$, 1,3-dioxolan-2-yl or $R^2$ and $R^3$ taken together with —OCF₂O—; R⁵ is hydrogen; R⁹ is selected from —OCH₂CH₂OCH₃, —CH=NOCH₃, —CH=NOC₂H₅, —CH=NOCH₂CN, —CH=NOCH₂CH₂OCH₃, —NHCO₂CH(CH₃)₂, —OC(=O)NHCH(CH₃)₂, pyrimidin-2-yl, pyrid-2-yl, 3-chloro-pyrid-2-yl, 3-methyl-pyrid-2-yloxy, 4-methyl-pyrid-2-yloxy, 5-methyl-pyrid-2-yloxy, 6-methyl-pyrid-2-yloxy, 3-chloro-pyrid-2-yloxy, 3-trifluoromethyl-pryid-2-yloxy, 3-cyano-pyrid-2-yloxy, 5-cyano-pyrid-2-yloxy, 6-dimethoxymethyl-pyrid-2-yloxy, pyrid-2-yloxy, pyrimidin-2-yloxy, 6-chloro-pyridazin-3-yloxy, 6-methoxy-pyridazin-3-yloxy or 6-methyl-pyridazin-3yloxy; and R is phenyl substituted with R¹⁴, R¹⁵, R¹⁶, R¹⁷, and R¹⁸,

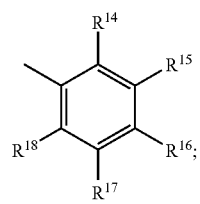

where
R¹⁴, R¹⁵, R¹⁶ and R¹⁷ are independently selected from fluorine, chlorine, trifluoromethyl, difluoromethoxy, trifluoromethoxy, —OCF₂CHFCF₃ or R¹⁵ and R¹⁶ taken together with —OCF₂O—.

4. The compound of claim 3, wherein X is hydroxyl; Y is hydrogen; R³ is haloalkoxy; R⁹ is selected —OCH₂CH₂OCH₃, —CH=NOCH₃, —CH=NOC₂H₅, —CH=NOCH₂CN, —CH=NOCH₂CH₂OCH₃, —NHCO₂CH(CH₃)₂, —OC(=O)NHCH(CH₃)₂, pyrid-2-yloxy, pyrid-2-yl, 3-cyano-pyrid-2-yloxy, 5-methyl-pyrid-2-yloxy, pyrimidin-2-yloxy, pyrimidin-2-yl, 6-chloro-pyridazin-3-yloxy or 6-methoxy-pyridazin-3-yloxy; and R¹⁶ is haloalkoxy.

5. A compound of formula I:

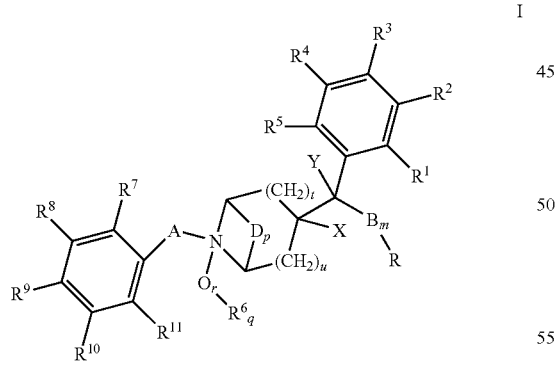

wherein;
r is selected from 0 or 1; m, q and p are 0; t and u are 1;
A is —CH₂—;
X is selected from halogen or hydroxyl;
Y is selected from hydrogen or hydroxyl;
R¹, R², R³ and R⁴ are independently selected from hydrogen, halogen, alkyl, alkoxy, haloalkyl, haloalkoxy or —CH=NOC₂H₅;
R⁵ is hydrogen;
R⁷, R⁸, R¹⁰ and R¹¹ are hydrogen;

R⁹ is selected from —OC₂H₅, —OC₃H₇, —OCH(CH₃)₂, —OCH₂CH₂OCH₃, —OCH₂CH₂CH₂OCH₃, cyclopropylmethoxy, 2-chlorophenoxy, 3-chlorophenoxy, 4-chlorophenoxy, pyrimidin-2-yl, pyrid-2-yl, 3-chloro-pyrid-2-yl, 3-methyl-pyrid-2-yloxy, 4-methyl-pyrid-2-yloxy, 5-methyl-pyrid-2-yloxy, 6-methyl-pyrid-2-yloxy, 3-chloro-pyrid-2-yloxy, 3-trifluoromethyl-pryid-2-yloxy, 3-cyano-pyrid-2-yloxy, 5-cyano-pyrid-2-yloxy, 6-dimethoxymethyl-pyrid-2-yloxy, pyrid-2-yloxy, CO₂CH(CH₃)₂, —CH=NOCH₃, —CH=NOC₂H₅, —CH=NOCH₂CF₃, —CH=NOallyl, —CH=NOCH₂CH=CH₂, —CH=NOCH₂CN, —CH=NOCH(CH₃)₂, —CH=NOCH₂C≡CH, —CH=NOCH₂CH₂F, —CH=NOCH₂CH₂OCH₃, —CH=NOCH₂OC₂H₅, —CH=NOCH₂CH₂OCH₂CH₂OCH₃, —NHCO₂CH₃, —NHCO₂C₂H₅, —NHCO₂CH(CH₃)₂, —NHCO₂CH₂-c-C₃H₅, —CH(OH)C₆H₅-p-Cl, —OC(=O)NHCH₃, —OC(=O)NHC₂H₅, —OC(=O)NHCH(CH₃)₂, —NHC(SCH₃)=NCN, pyrimidin-2-yloxy, 6-chloro-pyridazin-3-yloxy, 6-methoxy-pyridazin-3-yloxy, 6-methyl-pyridazin-3-yloxy, 2-methyl-2H-tetrazol-5-yl, 2-ethyl-2H-tetrazol-5-yl, 1,3-dioxan-2-yl or 5,5-dimethyl-1,3-dioxan-2-yl; and R is phenyl substituted with R¹⁴, R¹⁵, R¹⁶, R¹⁷, and R¹⁸,

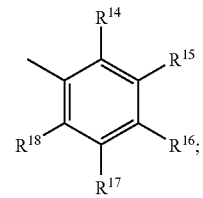

where
R¹⁶ is selected from haloalkyl or haloalkoxy, and R¹⁴, R¹⁵, R¹⁷ and R¹⁸ are hydrogen.

6. A compound of formula I-H:

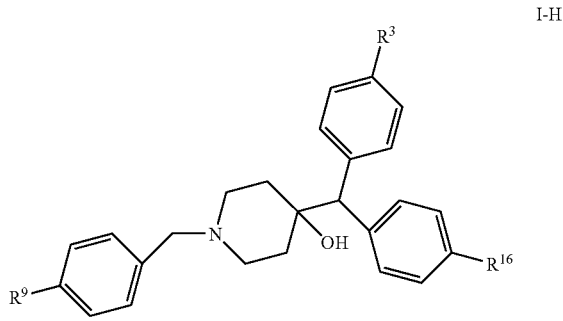

wherein,
R³ is haloalkyl or haloalkoxy;
R⁹ is selected from —OCH₂CH₂OCH₃, pyrid-2-yloxy, pyrid-2-yl, 3-cyano-pyrid-2-yloxy, 5-methyl-pyrid-2-yloxy, pyrimidin-2-yloxy, pyrimidin-2-yl, 6-chloro-pyridazin-3-yloxy or 6-methoxy-pyridazin-3-yloxy; and
R¹⁶ is haloalkyl or haloalkoxy.

7. A compound of formula I-J:

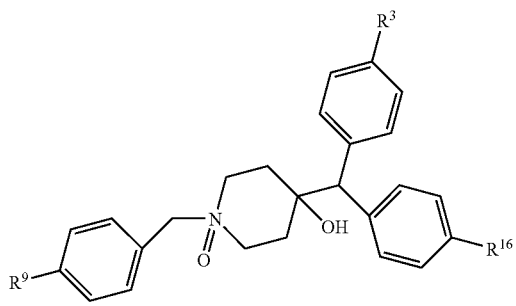

wherein,
R³ is haloalkyl or haloalkoxy;
R⁹ is selected from —OCH₂CH₂OCH₃, pyrid-2-yloxy, pyrid-2-yl, 3-cyano-pyrid-2-yloxy, 5-methyl-pyrid-2-yloxy, pyrimidin-2-yloxy, pyrimidin-2-yl, 6-chloro-pyridazin-3-yloxy or 6-methoxy-pyridazin-3-yloxy; and
R¹⁶ is haloalkyl or haloalkoxy.

8. The compound:

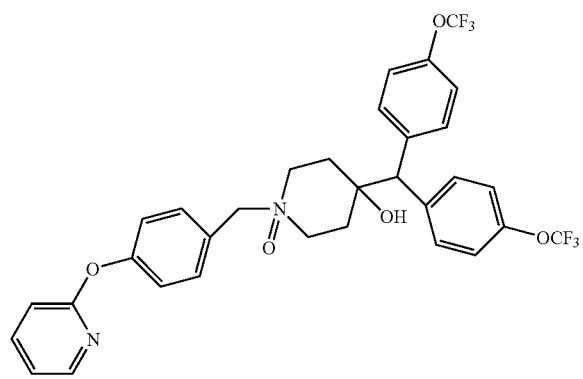

namely, 4-{bis[4-(trifluoromethoxy)phenyl]methyl}-4-hydroxy-1-[(4-(2-pyridyloxy)phenyl)methyl]piperidin-1-oxide, and agriculturally-acceptable salts thereof.

9. A composition containing an insecticidally effective amount of a compound of claim 1 in admixture with at least one agriculturally acceptable extender or adjuvant.

10. A composition containing an insecticidally effective amount of a compound of claim 2 in admixture with at least one agriculturally acceptable extender or adjuvant.

11. A composition containing an insecticidally effective amount of a compound of claim 3 in admixture with at least one agriculturally acceptable extender or adjuvant.

12. A composition containing an insecticidally effective amount of a compound of claim 4 in admixture with at least one agriculturally acceptable extender or adjuvant.

13. A composition containing an insecticidally effective amount of a compound of claim 5 in admixture with at least one agriculturally acceptable extender or adjuvant.

14. A composition containing an insecticidally effective amount of a compound of claim 6 in admixture with at least one agriculturally acceptable extender or adjuvant.

15. A composition containing an insecticidally effective amount of a compound of claim 7 in admixture with at least one agriculturally acceptable extender or adjuvant.

16. A composition containing an insecticidally effective amount of a compound of claim 8 in admixture with at least one agriculturally acceptable extender or adjuvant.

17. A method of controlling insects, comprising applying an insecticidally effective amount of a composition of claim 9 to a locus where insects are present or are expected to be present.

18. A method of controlling insects, comprising applying an insecticidally effective amount of a composition of claim 10 to a locus where insects are present or are expected to be present.

19. A method of controlling insects, comprising applying an insecticidally effective amount of a composition of claim 11 to a locus where insects are present or are expected to be present.

20. A method of controlling insects, comprising applying an insecticidally effective amount of a composition of claim 12 to a locus where insects are present or are expected to be present.

21. A method of controlling insects, comprising applying an insecticidally effective amount of a composition of claim 13 to a locus where insects are present or are expected to be present.

22. A method of controlling insects, comprising applying an insecticidally effective amount of a composition of claim 14 to a locus where insects are present or are expected to be present.

23. A method of controlling insects, comprising applying an insecticidally effective amount of a composition of claim 15 to a locus where insects are present or are expected to be present.

24. A method of controlling insects, comprising applying an insecticidally effective amount of a composition of claim 16 to a locus where insects are present or are expected to be present.

* * * * *